(12) United States Patent
Lin

(10) Patent No.: US 9,974,254 B2
(45) Date of Patent: May 22, 2018

(54) METHOD OF PLANT GENOME DESIGN, METHOD OF CREATING NEW CULTIVAR AND NEW CULTIVAR

(71) Applicant: HONDA MOTOR CO., LTD., Minato-ku, Tokyo (JP)

(72) Inventor: Shaoyang Lin, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 1085 days.

(21) Appl. No.: 13/656,367

(22) Filed: Oct. 19, 2012

(65) Prior Publication Data
US 2013/0133112 A1 May 23, 2013

Related U.S. Application Data

(62) Division of application No. 13/001,290, filed as application No. PCT/JP2009/062392 on Jul. 7, 2009, now Pat. No. 8,889,948.

(30) Foreign Application Priority Data

Jul. 7, 2008 (JP) .................................. 2008-176934

(51) Int. Cl.
| | |
|---|---|
| A01H 1/02 | (2006.01) |
| A01H 5/10 | (2018.01) |
| A01H 1/04 | (2006.01) |
| A01H 1/00 | (2006.01) |
| C12Q 1/68 | (2018.01) |

(52) U.S. Cl.
CPC ................. *A01H 1/02* (2013.01); *A01H 1/00* (2013.01); *A01H 1/04* (2013.01); *A01H 5/10* (2013.01); *C12Q 1/6827* (2013.01)

(58) Field of Classification Search
None
See application file for complete search history.

(56) References Cited

U.S. PATENT DOCUMENTS

| | | | | |
|---|---|---|---|---|
| 9,029,669 | B2 * | 5/2015 | Lin ........................... | A01H 5/10 800/320.2 |
| 2006/0123507 | A1 | 6/2006 | Ashikari et al. | |

FOREIGN PATENT DOCUMENTS

| | | |
|---|---|---|
| EP | 1 229 119 A1 | 8/2002 |
| JP | 3660967 B2 | 6/2005 |
| JP | 2007-049994 A | 3/2007 |
| WO | WO 03/070934 A1 | 8/2003 |

OTHER PUBLICATIONS

Takeuchi et al et al (Breeding Science (2006) 56: 405-413).*
Ashikari et al (Science vol. 309, (2005): Issue 5735, pp. 741-745).*
Ashikari et al (Science vol. 309, (2005): Issue 5735, pp. 741-745). (Year: 2005).*
Koshihikari Eichi 2go, Published Application Data Base Food Crop No date available.
Koshihikari Eichi 3go, Published Application Data Base Food Crop No date available.
Koshihikari Eichi 4go, Published Application Data Base Food Crop No date available.
Eiji Yamamoto et al., "Interaction of Two Recessive Genes, *hbd2* and *hbd3*, induces Hybrid Breakdown in Rice", Theor. Appl. Genet., 2007, pp. 187-194, vol. 115, No. 2.
Yoshinobu Takeuchi et al., "Development of Isogenic Lines of Rice Cultivar Koshihikari with Early and Late Heading by Marker-Assisted Selection", Breeding Science, 2006, pp. 405-413, vol. 56, No. 4.
Motoyuki Ashikari et al., "Cytokinin Oxidase Regulates Rice Grain Production", Science, Jul. 29, 2005, pp. 741-745, vol. 309.
Hiroaki Tabuchi et al., "Genetic Analysis of Semidwarfism of the *japonica* Rice Cultivar Kinuhikari", Breeding Science, 2000, pp. 1-7, vol. 50, No. 1.
Hiroko Miura et al., "Analysis of QTLs for Lodging Resistance of Rice Using Habataki Chromosome Segment Substitution Lines in Koshihikari Background", Jpn. J. Crop. Sci., 2008, pp. 206-207 with English translation, vol. 77 (Annex 1).
Y. Takahashi et al., "Linkage Map and YAC Contig of the Chromomal Region Containing a Rice Photoperiod Sensitivity Gene, Hd-6", Breeding Science, 1998, p. 69 with English translation, vol. 48, Supplement No. 1.
S. Kojima et al., "Fine-Scale Genetic Linkage Map and Physical Mapping of a Rice Photoperiod Sensitivity Gene, Hd-3", Breeding Science, 1998, p. 96 with English translation, vol. 48, Supplement No. 2.
T. Shimizu et al., "Detection of QTLs Controlling Heading Date of Rice Using Back Cross Progenies", 1997, p. 45 with English translation, vol. 47, Supplement No. 1.
Koshihikari Kazusa 4-go, Published Application Data Base Food Crop, Jun. 22, 2009.

(Continued)

*Primary Examiner* — Lee A Visone
(74) *Attorney, Agent, or Firm* — Carrier Blackman & Associates, P.C.; Joseph P. Carrier; Fulchand P. Shende

(57) ABSTRACT

Plant genome design method defines DNA markers M1 to M5, for target region, DNA marker M2 is defined at an end on an upstream side of a target region, or upstream thereof, DNA marker M1 is defined upstream of the DNA marker M2, DNA marker M4 is defined at an end on a downstream side of the target region, or downstream thereof, DNA marker M5 is defined downstream of the DNA marker M4, and DNA marker M3 is defined in the target region; and designs a genome so that a substitution region, containing the target region, in a chromosome of the original cultivar to be substituted with a chromosome fragment derived from the foreign cultivar has an end on an upstream side between DNA marker M1 and DNA marker M2, and an end on a downstream side of the substitution region between DNA marker M4 and DNA marker M5.

2 Claims, 22 Drawing Sheets

(56) References Cited

OTHER PUBLICATIONS

"Report on Research and Development in Agriculture and Fisheries No. 21 Use of Genome Information for Improvement of Cultivar-DNA Marker Breeding", Ministry of Agriculture, Forestry and Fisheries of Japan, Jul. 31, 2007, pp. 3-4 with English translation.
Takeuchi et al. 2006. Breeding Science 56:405-413.
Office Action issued on Japanese Patent Application No. 2008-176934 dated Oct. 21, 2008.
Decision of Rejection issued on Japanese Patent Application No. 2008-176934 dated Mar. 17, 2009.
Notice of Allowance issued on Japanese Patent Application No. 2009-120405 dated Jun. 30, 2009.
Office Action issued on Japanese Patent Application No. 2008-176934 dated Aug. 11, 2009.
International Search Report issued on the related PCT (PCT/JP2009/062392).
Chinese Office Action / Search Report issued in corresponding CN Patent Application 201310220211.1 dated Jun. 20, 2014, and the English translation of Search Report.
Wu Haibin et al., "Recent Progress of QTL Cloning in Rice", Proceedings of the Workshop on Research & Development of Biotechnology in Hainan, Aug. 1, 2006, pp. 61-64.
Eiji Yamamoto et al., "Interaction of Two Recessive Genes, *hbd2* and *hbd3*, induces Hybrid Breakdown in Rice", Theor. Appl. Genet., 2007, pp. 187-194, vol. 115.
Yoshinobu Takeuchi et al., "Development of Isogenic Lines of Rice Cultivar Koshihikari with Early and Late Heading by Marker-Assisted Selection", Breeding Science, 2006, pp. 405-413, vol. 56.
Hiroaki Tabuchi et al., "Genetic Analysis of Sermidwarfism of the *japonica* Rice Cultivar Kinuhikari", Breeding Science, 2000, pp. 1-7, vol. 50.
Hiroko Miura et al., "Analysis of QTL's for Lodging Resistance of Rice Using Habataki Chromosome Segment Substitution Lines in Koshihikari Background", Jpn. J. Crop. Sci., 2008,:1 pp. 206-207 with English translation, vol. 77 (Annex 1).
S. Kojima et al., "Fine-Scale Genetic Linkage Map and Physical Mapping of Rice Photoperiod Sensitivity Gene, Hd-3", Breeding Science, 1998, p. 96 with English translation, vol. 48, Supplement No. 2.
T. Shimizu et al., "Detection of QTL's Controlling Heading Date of Rice Using Back Cross Progenies", 1997, p. 45 with English translation, vol. 47, Supplement No. 1.
"Report on Research and Development in Agriculture and Fisheries No. 21 Use of Genome Information for Improvement of Cultivar-DNA Marker Breeding", Ministry of Agriculture, Forestry and Fisheries of Japan, Jul. 31, 2007, pp. 34 with English translation.

* cited by examiner

SEQUENCE LISTING

<160> NUMBER OF SEQ ID NOS: 43

<210> SEQ ID NO 1
<211> LENGTH: 20
<212> TYPE: DNA
<213> ORGANISM: Oryza sativa

<400> SEQUENCE: 1
ccgttcatgt gcctgtatgg                                                   20

<210> SEQ ID NO 2
<211> LENGTH: 20
<212> TYPE: DNA
<213> ORGANISM: Oryza sativa

<400> SEQUENCE: 2
tgttgcagga aggtgacaca                                                   20

<210> SEQ ID NO 3
<211> LENGTH: 21
<212> TYPE: DNA
<213> ORGANISM: Oryza sativa

<400> SEQUENCE: 3
ttggaaggaa catctagcag g                                                 21

<210> SEQ ID NO 4
<211> LENGTH: 18
<212> TYPE: DNA
<213> ORGANISM: Oryza sativa

<400> SEQUENCE: 4
cacagcgctc acttctca                                                     18

<210> SEQ ID NO 5
<211> LENGTH: 20
<212> TYPE: DNA
<213> ORGANISM: Oryza sativa

<400> SEQUENCE: 5
tgcaatgtcg tccaccatcg                                                   20

<210> SEQ ID NO 6
<211> LENGTH: 18
<212> TYPE: DNA
<213> ORGANISM: Oryza sativa

<400> SEQUENCE: 6
cacagcgctc acttctca                                                     18

<210> SEQ ID NO 7
<211> LENGTH: 19
<212> TYPE: DNA
<213> ORGANISM: Oryza sativa

<400> SEQUENCE: 7
atgatcgtca gcgacagct                                                    19

<210> SEQ ID NO 8
<211> LENGTH: 18
<212> TYPE: DNA
<213> ORGANISM: Oryza sativa

<400> SEQUENCE: 8

```
aactccagcg tgctaagc                                                  18

<210> SEQ ID NO 9
<211> LENGTH: 18
<212> TYPE: DNA
<213> ORGANISM: Oryza sativa

<400> SEQUENCE: 9
gcattgcatg caggatcg                                                  18

<210> SEQ ID NO 10
<211> LENGTH: 19
<212> TYPE: DNA
<213> ORGANISM: Oryza sativa

<400> SEQUENCE: 10
agagcccttc actttcagc                                                 19

<210> SEQ ID NO 11
<211> LENGTH: 18
<212> TYPE: DNA
<213> ORGANISM: Oryza sativa

<400> SEQUENCE: 11
aaggctgatg agcactgc                                                  18

<210> SEQ ID NO 12
<211> LENGTH: 19
<212> TYPE: DNA
<213> ORGANISM: Oryza sativa

<400> SEQUENCE: 12
ggcattgtgg aagctcttc                                                 19

<210> SEQ ID NO 13
<211> LENGTH: 17
<212> TYPE: DNA
<213> ORGANISM: Oryza sativa

<400> SEQUENCE: 13
tctcctttcg gagtccc                                                   17

<210> SEQ ID NO 14
<211> LENGTH: 21
<212> TYPE: DNA
<213> ORGANISM: Oryza sativa

<400> SEQUENCE: 14
cattgagtcc atttcctctg c                                              21

<210> SEQ ID NO 15
<211> LENGTH: 20
<212> TYPE: DNA
<213> ORGANISM: Oryza sativa

<400> SEQUENCE: 15
gcagctccaa gaatgactac                                                20

<210> SEQ ID NO 16
<211> LENGTH: 20
<212> TYPE: DNA
<213> ORGANISM: Oryza sativa
```

<400> SEQUENCE: 16
attggtgcta gagcaactac                                               20

<210> SEQ ID NO 17
<211> LENGTH: 20
<212> TYPE: DNA
<213> ORGANISM: Oryza sativa

<400> SEQUENCE: 17
gtgagacata gactatccac                                               20

<210> SEQ ID NO 18
<211> LENGTH: 19
<212> TYPE: DNA
<213> ORGANISM: Oryza sativa

<400> SEQUENCE: 18
acgcgtacgc cacatagac                                                19

<210> SEQ ID NO 19
<211> LENGTH: 19
<212> TYPE: DNA
<213> ORGANISM: Oryza sativa

<400> SEQUENCE: 19
agggtgagga atgtccggt                                                19

<210> SEQ ID NO 20
<211> LENGTH: 20
<212> TYPE: DNA
<213> ORGANISM: Oryza sativa

<400> SEQUENCE: 20
gcagtacctg ccttactacg                                               20

<210> SEQ ID NO 21
<211> LENGTH: 20
<212> TYPE: DNA
<213> ORGANISM: Oryza sativa

<400> SEQUENCE: 21
catttcatgc gagtggtgac                                               20

<210> SEQ ID NO 22
<211> LENGTH: 20
<212> TYPE: DNA
<213> ORGANISM: Oryza sativa

<400> SEQUENCE: 22
tgcacgaatc ttggccagag                                               20

<210> SEQ ID NO 23
<211> LENGTH: 24
<212> TYPE: DNA
<213> ORGANISM: Oryza sativa

<400> SEQUENCE: 23
cttaaactca acttgcacaa gtag                                          24

<210> SEQ ID NO 24
<211> LENGTH: 20
<212> TYPE: DNA
<213> ORGANISM: Oryza sativa

```
<400> SEQUENCE: 24
actgccgaca tgttactgtc                                          20

<210> SEQ ID NO 25
<211> LENGTH: 21
<212> TYPE: DNA
<213> ORGANISM: Oryza sativa

<400> SEQUENCE: 25
gtcccacctg aaacatatcc a                                        21

<210> SEQ ID NO 26
<211> LENGTH: 22
<212> TYPE: DNA
<213> ORGANISM: Oryza sativa

<400> SEQUENCE: 26
tctttgattc tttggtcgat cg                                       22

<210> SEQ ID NO 27
<211> LENGTH: 20
<212> TYPE: DNA
<213> ORGANISM: Oryza sativa

<400> SEQUENCE: 27
gcgtacgaga gctatagagc                                          20

<210> SEQ ID NO 28
<211> LENGTH: 20
<212> TYPE: DNA
<213> ORGANISM: Oryza sativa

<400> SEQUENCE: 28
atggatccgt ggatcgatcg                                          20

<210> SEQ ID NO 29
<211> LENGTH: 22
<212> TYPE: DNA
<213> ORGANISM: Oryza sativa

<400> SEQUENCE: 29
gcgaaaagat gaggatgtac ac                                       22

<210> SEQ ID NO 30
<211> LENGTH: 20
<212> TYPE: DNA
<213> ORGANISM: Oryza sativa

<400> SEQUENCE: 30
ccgtaggcct ttgtcaagtg                                          20

<210> SEQ ID NO 31
<211> LENGTH: 20
<212> TYPE: DNA
<213> ORGANISM: Oryza sativa

<400> SEQUENCE: 31
ctttaatggt ggcttatgtc                                          20

<210> SEQ ID NO 32
<211> LENGTH: 22
<212> TYPE: DNA
```

<213> ORGANISM: Oryza sativa

<400> SEQUENCE: 32
gctaggacaa gcttatttca gc    22

<210> SEQ ID NO 33
<211> LENGTH: 18
<212> TYPE: DNA
<213> ORGANISM: Oryza sativa

<400> SEQUENCE: 33
tcacgccgat caagaacg    18

<210> SEQ ID NO 34
<211> LENGTH: 24
<212> TYPE: DNA
<213> ORGANISM: Oryza sativa

<400> SEQUENCE: 34
cataatttat cgccattttc gcat    24

<210> SEQ ID NO 35
<211> LENGTH: 18
<212> TYPE: DNA
<213> ORGANISM: Oryza sativa

<400> SEQUENCE: 35
aggcccttgt actggtac    18

<210> SEQ ID NO 36
<211> LENGTH: 21
<212> TYPE: DNA
<213> ORGANISM: Oryza sativa

<400> SEQUENCE: 36
gtacacaata gttggtgcac c    21

<210> SEQ ID NO 37
<211> LENGTH: 19
<212> TYPE: DNA
<213> ORGANISM: Oryza sativa

<400> SEQUENCE: 37
catgataagg tactcctgg    19

<210> SEQ ID NO 38
<211> LENGTH: 22
<212> TYPE: DNA
<213> ORGANISM: Oryza sativa

<400> SEQUENCE: 38
cctagtccct aaagatctca tg    22

<210> SEQ ID NO 39
<211> LENGTH: 21
<212> TYPE: DNA
<213> ORGANISM: Oryza sativa

<400> SEQUENCE: 39
gatagacatg acggagaagt g    21

<210> SEQ ID NO 40
<211> LENGTH: 19

```
<212> TYPE: DNA
<213> ORGANISM: Oryza sativa

<400> SEQUENCE: 40
gggtggtgtt atctctagt                                              19

<210> SEQ ID NO 41
<211> LENGTH: 20
<212> TYPE: DNA
<213> ORGANISM: Oryza sativa

<400> SEQUENCE: 41
gcgcaaattc cttcagtcac                                             20

<210> SEQ ID NO 42
<211> LENGTH: 19
<212> TYPE: DNA
<213> ORGANISM: Oryza sativa

<400> SEQUENCE: 42
cagtttcagg tggaagacc                                              19

<210> SEQ ID NO 43
<211> LENGTH: 22
<212> TYPE: DNA
<213> ORGANISM: Oryza sativa

<400> SEQUENCE: 43
caagtttctt cctctcattt tc                                          22
```

METHOD OF PLANT GENOME DESIGN, METHOD OF CREATING NEW CULTIVAR AND NEW CULTIVAR

CROSS-REFERENCED TO RELATED APPLICATIONS

This is a Divisional Application of U.S. patent application Ser. No. 13/001,290 filed Dec. 23, 2010, which is a National Stage entry of International Application No. PCT/JP2009/062392, filed Jul. 7, 2009, which claims priority to Japanese Patent Application No. P2008-176934, filed Jul. 7, 2008, the disclosure of the prior applications are incorporated in their entirety by reference.

SEQUENCE LISTING

The instant application contains a Sequence Listing which has been submitted in ASCII format via EFS-Web and is hereby incorporated by reference in its entirety. Said ASCII copy, created on Jan. 15, 2013, is named 17439300.txt and is 6,537 bytes in size.

TECHNICAL FIELD

The present invention relates to a method of designing a plant genome by a non-gene recombinant method, which is suitable for improving a cultivar, a method of creating a new cultivar using this genome design method, a plant individual and a new cultivar created by this method, and a method of discriminating a plant cultivar.

The present application claims priority on Japanese Patent Application No. 2008-176934 filed on Jul. 7, 2008, the disclosure of which is incorporated by reference herein.

BACKGROUND ART

A population which belongs to the same organism species, but has a different character from that of other population in a certain character due to different genetic construction is called variety (cultivar). That is, even the same kind of plant is different in difficulty of culturing, pest resistance, yield, quality or the like, depending on a cultivar. For this reason, in agricultural crops, particularly, main crops such as rice and wheat, cultivar improvement for obtaining a more excellent cultivar has been conducted from old times. In recent years, this cultivar improvement has been positively conducted in not only seed and plant suppliers but also public organizations such as country and prefecture. In addition, in order to response to variety of taste of consumers in recent years, in horticultural crops such as grasses and flowers in addition to edible crops, a new cultivar having a variety of colors and morphologies is vigorously being developed.

Further, in recent years, an attention is paid to a plant source as a raw material such as biomass ethanol and the like, and development of a new cultivar having high source efficiency is expected.

With advance of nucleic acid analysis technique or the like in recent years, genes of a variety of plants such as *Arabidopsis*, rice, wheat and the like have been analyzed, and genetic information obtained by this analysis has been disclosed. Utilizing the disclosed genetic information, cultivar improvement of introducing a foreign species gene into an original cultivar by a gene recombinant method is performed frequency. For example, a Hd1 gene encoding a protein derived from a plant having the function of increasing photosensitivity of a plant, and a method of creating a transformed plant with this Hd1 gene introduced therein, and the like are disclosed (see, for example, Patent document 1). However, although cultivar improvement by a gene recombinant method has an advantage that a character possessed by a distant species which cannot be usually mated can be introduced, there is a problem that study of safety thereof is not necessarily sufficient.

On the other hand, as a method of improving a plant cultivar by a non-gene recombinant method, there are a breeding method by mating and a mutation method. As a breeding method by normal mating, there is a pedigree breeding method, a population breeding method, a backcross breeding method and the like. Alternatively, by combining the backcross breeding method and MAS (Marker Assisted Selection) method, cultivar improvement of introducing a target gene into an original cultivar is also widely performed. Herein, the MAS method is a method of selecting an individual having an objective character from a population of a cross progeny obtained by natural mating which has been conducted from old times or artificial mating using a DNA marker linked to a gene encoding an objective character. By performing individual selection using this DNA marker, an individual having an objective character can be selected at an early stage such as a seedling stage and the like, and it can save labor and improve efficiency. As a method of selecting an individual having a particular character using such the DNA marker, for example, a method of determining a genotype of a plant using a DNA marker present in a region surrounding a sd-1 gene which is a rice semidwarf gene, and a method of testing semidwarf character of a plant using this method are disclosed (see, for example, Patent document 2).

RELATED DOCUMENTS

Patent Document

[Patent document 1] Japanese Patent No. 3,660,967
[Patent document 2] International Publication No. WO 2003/070934

DISCLOSURE OF INVENTION

Problem to be Solved by the Invention

However, in the cultivar improvement method using the MAS method, there is a problem that a progeny individual selected using the DNA marker is not necessarily an individual having an objective character, and a role of the DNA marker becomes only assistant selection. This is presumed that the DNA marker is usually not on a character gene to be introduced, and a distance whose length and direction are unknown is present between this character gene and the DNA marker. For this reason, in the MAS method, a size of a population of a progeny individual to be character-assessed can be reduced, but it is still necessary to further assess a character of a progeny individual selected using the DNA marker.

In addition, in the cultivar improvement method using the MAS method, there is also a problem that a character of a target is improved, but other character is deteriorated. This is presumed, as described above, that since a distance whose length and direction are unknown is present between an introduced character gene and the DNA marker, a region of a chromosome fragment to be introduced cannot be controlled, and many other genes other than an objective character gene are introduced into the plant.

One of objects of the present invention is to provide a method of plant genome design and a method of creating new cultivar for controlling a substitution region with a chromosome fragment derived from a foreign cultivar to be introduced, and creating a new cultivar having a target character without changing a preferable character possessed by an original cultivar, in the case where improvement in a cultivar is performed by a non-gene recombinant method.

Means for Solving the Problems

The present inventors have intensively studied in order to solve the above problems and found that, when a new cultivar in which a target region in a chromosome of an original cultivar is substituted with a homo-chromosome fragment derived from a foreign cultivar is created using a chromosome fragment-substituted line, by satisfying the following conditions (I) and (II), a chromosome region of an original cultivar substituted with this homo-chromosome fragment can be controlled, resulting in completion of the present invention.

(I) A DNA marker M2 is defined at an end on an upstream side of a target region, or upstream thereof, a DNA marker M1 is defined upstream of the DNA marker M2, a DNA marker M4 is defined at an end on a downstream side of the target region, or downstream thereof, a DNA marker M5 is defined downstream of the DNA marker M4, and a DNA marker M3 is defined in the target region.

(II) A progeny individual in which an end on an upstream side of a chromosome region of an original cultivar to be substituted with a chromosome fragment derived from a foreign cultivar to be introduced is between DNA markers M1 and M2, and an end on a downstream side of this region is between DNA markers M4 and M5, is selected.

(1) A plant genome design method of the present invention is a method of designing a plant genome in which a target region in a chromosome of an original cultivar is substituted with a chromosome fragment derived from the foreign cultivar using a chromosome fragment-substituted line in which only a part of a chromosome of an original cultivar is substituted with a chromosome fragment derived from a foreign cultivar, the method comprising: designing NA markers M1 to M5 so that, for every one target region, a DNA marker M2 is defined at an end on an upstream side of the target region, or upstream thereof, a DNA marker M1 is defined upstream of the DNA marker M2, a DNA marker M4 is defined at an end on a downstream side of the target region, or downstream thereof, a DNA marker M5 is defined downstream of the DNA marker M4, and a DNA marker M2 is defined in the target region; and designing a genome so that a substitution region, containing the target region, in a chromosome of the original cultivar to be substituted with a chromosome fragment derived from the foreign cultivar is such that an end on an upstream side of it is between the DNA marker M1 and the DNA marker M2, and an end on a downstream side of the substitution region is between the DNA marker M4 and the DNA marker M5.

(2) A method of creating a new cultivar of the present invention is a method of creating a new cultivar using a chromosome fragment-substituted line in which only a part of a chromosome of an original cultivar is substituted with a chromosome fragment derived from a foreign cultivar, comprises: (1-1) a step of defining a DNA marker M2 at an end on an upstream side of a target region of a chromosome of the original cultivar, or upstream thereof, a step of defining a DNA marker M1 upstream of the DNA marker M2, a step of defining a DNA marker M4 at an end on a downstream side of the target region, or downstream thereof, a step of defining a DNA marker M5 downstream of the DNA marker M4, a step of defining a DNA marker M3 in the target region; (1-2) a step of mating the chromosome fragment-substituted line and the original cultivar to obtain a progeny individual in which the DNA marker M3 is a hetero-chromosome region of an allele derived from the original cultivar and an allele derived from a foreign cultivar; (1-3) a step of self-mating the progeny individual obtained in the step (1-2) to obtain a progeny individual; (1-4) a step of selecting a progeny individual in which the DNA marker M1 is a homo-chromosome region of an allele derived from the original cultivar, and the DNA marker M2 and the DNA marker M3 is a hetero-chromosome region of an allele derived from the original cultivar and an allele derived from the foreign cultivar, from a progeny individual obtained by backcrossing the progeny individual obtained in the step (1-3), or the progeny individual obtained in the step (1-3); (1-5) a step of self-mating the progeny individual selected in the step (1-4) to obtain a progeny individual; (1-6) a step of selecting a progeny individual in which the DNA marker M1 and the DNA marker M5 is a homo-chromosome region of an allele derived from the original cultivar, and the DNA marker M2, the DNA marker M3, and the DNA marker M4 are a homo-chromosome region of an allele derived from the foreign cultivar, from the progeny individual obtained in the step (1-5), or a progeny individual obtained by the self-mating the progeny individual obtained in the step (1-5), wherein the steps (1-1) to (1-6) are performed for the every one target region, on one or a plurality of the target regions in the chromosome of the original cultivar.

(3) A method of creating a new cultivar of the present invention is a method of creating a new cultivar using a chromosome fragment-substituted line in which only a part of a chromosome of an original cultivar is substituted with a chromosome fragment derived from a foreign cultivar, the method comprising: (2-1) a step of defining a DNA marker M2 at an end on an upstream side of a target region of a chromosome of the original cultivar, a step of defining a DNA marker M1 upstream of the DNA marker M2, a step of defining a DNA marker M4 at an end on a downstream side of the target region, or downstream thereof, a step of defining a DNA marker M5 downstream of the DNA marker M4, a step of defining a DNA marker M3 in the target region; (2-2) a step of mating the chromosome fragment-substituted line and the original cultivar to obtain a progeny individual in which the DNA marker M3 is a hetero-chromosome region of an allele derived from the original cultivar and an allele derived from the foreign cultivar; (2-3) a step of self-mating the progeny individual obtained in the step (2-2) to obtain a progeny individual; (2-4) a step of selecting a progeny individual in which the DNA marker M5 is a homo-chromosome region of an allele derived from the original cultivar, and the DNA marker M3 and the DNA marker M4 are a hetero-chromosome region of an allele derived from the original cultivar and an allele derived from the foreign cultivar, from the progeny individual obtained in the step (2-3), or a progeny individual obtained by backcrossing the progeny individual obtained in the step (2-3); (2-5) a step of self-mating the progeny individual selected in the step (2-4) to obtain a progeny individual; (2-6) a step of selecting a progeny individual in which the DNA marker M1 and the DNA marker M5 are a homo-chromosome region of an allele derived from the original cultivar, and the DNA marker M2, the DNA marker M3, and the DNA marker M4 are a homo-chromosome region of an allele derived from the foreign cultivar, from the progeny individual obtained in the step (2-5), or a progeny individual obtained by the self-mating the progeny individual obtained in the step (2-5), wherein the steps (2-1) to (2-6) are performed for the every one target region on one or a plurality of the target regions in the chromosome of the original cultivar.

(4) A method of creating a new cultivar of the present invention is a method of creating a new cultivar using a chromosome fragment-substituted line in which only a part of a chromosome of an original cultivar is substituted with a chromosome fragment derived from a foreign cultivar, the method comprising (3-1) a step of defining a DNA marker M2 at an end on an upstream side of a target region of a chromosome of the original cultivar, a step of defining a DNA marker M1 upstream of the DNA marker M2, a step of defining at an end on a downstream side of the target region, or downstream thereof, a step of defining a DNA marker M5 downstream of the DNA marker M4, a step of defining a DNA marker M3 in the target region; (3-2) a step of mating the chromosome fragment-substituted line, and the original cultivar to obtain a progeny individual in which the DNA marker M3 is a hetero-chromosome region of an allele derived from the original cultivar and an allele derived from the foreign cultivar; (3-3) a step of self-mating the progeny individual obtained in the step (3-2) to obtain a progeny individual; (3-4) a step of selecting a progeny individual in which any one of the DNA marker M1 and the DNA marker M5 is a homo-chromosome region of an allele derived from the original cultivar, and the other is a hetero-chromosome region of an allele derived from the original cultivar and an allele derived from the foreign cultivar, from the progeny individual obtained in the step (3-3), or a progeny individual obtained by backcrossing the progeny individual obtained in the step (3-3); (3-5) a step of self-mating the progeny individual selected in the step (3-4) to obtain a progeny individual; (3-6) a step of selecting a progeny individual in which the DNA marker M1 and the DNA marker M5 are a homo-chromosome region of an allele derived from the original cultivar, and the DNA marker M2, the DNA marker M3, and the DNA marker M4 are a homo-chromosome region of an allele derived from the foreign cultivar, from the progeny individual obtained in the step (3-5), or a progeny individual obtained by self-mating the progeny individual obtained in the step (3-5), wherein the steps (3-1) to (3-6) are performed for the every one target region on one or a plurality of the target regions in the chromosome of the original cultivar.

(5) The method of creating a new cultivar according to (4) may be such that, after the step (3-4) and before the step (3-5), (3-7-1) a step of obtaining a progeny individual by self-mating the progeny individual obtained in the step (3-4), and (3-7-2) a step of selecting (ii-1) a progeny individual in which the DNA marker M1 is a homo-chromosome region of an allele derived from the original cultivar, and the DNA marker M2 and the DNA marker M3 are a hetero-chromosome region of an allele derived from the original cultivar and an allele derived from the foreign cultivar, or (ii-2) a progeny individual in which the DNA marker M5 is a homo-chromosome region of an allele derived from the original cultivar, and the DNA marker M3 and the DNA marker M4 are a hetero-chromosome region of an allele derived from the original cultivar and an allele derived from the foreign cultivar, from the progeny individual obtained in the step (3-7-1), a progeny individual obtained by backcrossing the progeny individual obtained in the step (3-7-1), or a progeny individual obtained by backcrossing a progeny individual obtained by self-mating the progeny individual obtained in the step (3-7-1) are performed; the step (3-5) is (3-5') a step of obtaining a progeny individual by self-mating the progeny individual selected in the step (3-7-2); the step (3-6) is (3-6') a step of selecting a progeny individual in which the DNA marker M1 and the DNA marker M5 are a homo-chromosome region of an allele derived from the original cultivar, and the DNA marker M2, the DNA marker M3, and the DNA marker M4 are a homo-chromosome region of an allele derived from the foreign cultivar, from the progeny individual obtained in the step (3-5), or a progeny individual obtained by self-mating the progeny individual obtained in the step (3-5').

(6) The method of creating a new cultivar according to any one of (2) to (4) may be such that the DNA marker M2 is defined at an end on an upstream side of the target region, or in vicinity thereof; the DNA marker M1 is defined in vicinity of the DNA marker M2; the DNA marker M4 is defined at an end on a downstream side of the target region, or in vicinity thereof; the DNA marker M5 is defined in vicinity of the DNA marker M4.

(7) The method of creating a new cultivar according to any one of (2) to (4) may be such that the target region is one gene region.

(8) The method of creating a new cultivar according to any one of (2) to (4) may be such that the target region is 2 or more gene regions.

(9) The method of creating a new cultivar according to any one of (2) to (4) may be such that the original cultivar is an autogamous plant or a self-fertilizing plant.

(10) The method of creating a new cultivar according to any one of (2) to (4) may be such that the original cultivar is a cultivar of a Poaceae plant.

(11) The method of creating a new cultivar according to any one of (2) to (4) may be such that the original cultivar is a rice cultivar.

(12) The method of creating a new cultivar of according to (11) may be such that the rice cultivar is Koshihikari.

(13) A cultivar of the present invention is a cultivar created using the method of creating a new cultivar according to any one of (2) to (4), and a target region in a chromosome of the original cultivar is substituted with a homo-chromosome fragment derived from the foreign cultivar.

(14) A progeny individual of the present invention is obtained by mating two individuals selected from the group consisting of an individual of a cultivar according to (13) and a progeny individual of the individual of a cultivar according to (13).

(15) The progeny individual according to (14) may be such that a plurality of the target regions in a chromosome of the original cultivar are substituted with a homo-chromosome fragment derived from the foreign cultivar.

(16) The progeny individual according to (14) may be such that respective target regions of the two individuals are different.

(17) A progeny individual of the present invention is obtained by using, as a seed parent or a pollen parent, an individual selected from the group consisting of the individual of a cultivar according to (13) and a progeny individual of the individual of a cultivar according to (13), and mating the seed parent or the pollen parent.

(18) A method of creating a new cultivar of the present invention has (4-1) a step of using the cultivar according to (13) or the progeny individual according to (15) as a seed parent, and the cultivar according to (13) or the progeny individual according to (15) in which the target region is different from that of the seed parent as a pollen parent, and mating the seed parent and the pollen parent to obtain a progeny individual; (4-2) a step of obtaining a progeny individual by self-mating the progeny individual obtained in the step (4-1); (4-3) a step of selecting a progeny individual in which, in a chromosome of the original cultivar, both of the target region possessed by the seed parent and the target region possessed by the pollen parent are substituted with a homo-chromosome fragment derived from the foreign cultivar, from the progeny individual obtained in the step (4-2).

(19) The method of creating a new cultivar according to (18) may further have, after the step (4-3), (4-4) a step of selecting two individuals in which the target regions are different as a seed parent and a pollen parent, from the group consisting of the cultivar according to (13) or a progeny individual according to (15), and the individual selected in the step (4-3), and mating them to obtain a progeny individual; (4-5) a step of obtaining a progeny individual by self-mating the progeny individual obtained in the step (4-4); (4-6) a step of selecting a progeny individual in which, in a chromosome of the original cultivar, both of the target region possessed by the seed parent and the target region possessed by the pollen parent are substituted with a homo-chromosome fragment derived from the foreign cultivar, from the progeny individual obtained in the step (4-5); (4-7) a step of repeating the steps (4-4) to (4-6) once or more.

(20) A method of discriminating a plant cultivar of the present invention is a method of discriminating whether or not a plant individual is a particular cultivar created using the method of creating a new cultivar according to any one of (2) to (4), the method comprising: typing one or more of the DNA markers selected from the group consisting of the DNA markers M1 to M5 by genome analysis of the plant individual; and discriminating that the plant individual is the particular cultivar when the resulting typing result is consistent with the result of the particular cultivar.

(21) A new cultivar of the present invention is a progeny cultivar of a chromosome fragment-substituted line in which a part of a chromosome is substituted with a chromosome fragment derived from the foreign cultivar; one or a plurality of target regions of a chromosome regions are substituted with a chromosome fragment derived from the foreign cultivar; a length of the chromosome fragment is controlled by a DNA marker defined upstream of the target region, and a DNA marker defined downstream of a target region.

(22) Koshihikari of the present invention is *Oryza sativa* L. cultivar Koshihikari kazusa 4go, which has an accession number of international depositary of FERM BP-11140.

(23) A progeny individual of the present invention is obtained by mating two individuals selected from the group consisting of the individual of a cultivar according to (22) and a progeny individual according to (17).

(24) A method of discriminating a cultivar of the present invention is a method of discriminating whether or not a plant individual is a particular cultivar, the method comprising: letting SP-4009 to be a DNA marker M1, letting G2003 to be a DNA marker M2, letting G2002 to be a DNA marker M3, letting SP-462 to be a DNA marker M4, and letting SP-1259 to be a DNA marker M5; typing one or more of the DNA markers selected from the group consisting of the DNA markers M1 to M5 by genome analysis of the plant individual; and discriminating that the plant individual is *Oryza sativa* L. cultivar Koshihikari eichi 4go or *Oryza sativa* L. cultivar Koshihikari kazusa 4go when the resulting typing result is consistent with the result of *Oryza sativa* L. cultivar Koshihikari eichi 4go or *Oryza sativa* L. cultivar Koshihikari kazusa 4go.

(25) A method of discriminating a cultivar of the present invention is a method of discriminating whether or not a plant individual is a particular cultivar, the method comprising: letting SP-2032 to be a DNA marker M1, letting SP-170 to be a DNA marker M2, letting SP-4028 to be a DNA marker M3, letting SP4038 to be a DNA marker M4, and letting SP-4030 to be a DNA marker M5; typing one or more of the DNA markers selected from the group consisting of the DNA markers M1 to M5 by genome analysis of the plant individual; and discriminating that the plant individual is *Oryza sativa* L. cultivar Koshihikari eichi 2go or *Oryza sativa* L. cultivar Koshihikari kazusa 4go when the resulting typing result is consistent with the result of *Oryza sativa* L. cultivar Koshihikari eichi 2go or *Oryza sativa* L. cultivar Koshihikari kazusa 4go.

(26) A method of discriminating a cultivar of the present invention is the method of discriminating whether or not a plant individual is a particular cultivar, the method comprising: letting P-2513 to be a DNA marker M1, letting SP-586 to be a DNA marker M2, letting SP-2254 to be a DNA marker M3, letting SP-1603 to be a DNA marker M4, and letting SP-604 to be a DNA marker M5; typing one or more of the DNA markers selected from the group consisting of the DNA markers M1 to M5 by genome analysis of the plant individual; and discriminating that the plant individual is *Oryza sativa* L. cultivar Koshihikari eichi 3go or *Oryza sativa* L. cultivar Koshihikari kazusa 4go when the resulting typing result is consistent with the result of *Oryza sativa* L. cultivar Koshihikari eichi 3go or *Oryza sativa* L. cultivar Koshihikari kazusa 4go.

Effects of the Invention

By using the method of plant genome design of the present invention, and the method of creating a new cultivar of the present invention using this genome design method, a region of a chromosome of an original cultivar to be substituted with a homo-chromosome fragment derived from a foreign cultivar can be controlled. For this reason, an objective character can be introduced into an original cultivar while a possibility that many other genes having the unknown function other than an objective character gene are introduced into a chromosome of an original cultivar, and a possibility that a preferable character possessed by an original cultivar is damaged are kept to a minimum.

In addition, by using a new cultivar created by the method of creating a new cultivar of the present invention or a progeny individual thereof as a parent individual and thereby creating a new cultivar, it can be obtained a progeny individual in which all homo-chromosome fragments derived from foreign cultivars possessed by a seed parent and a pollen parent, respectively, are accumulated. As a result, plural kinds of characters of an original cultivar can be simply and safely improved, while a possibility that a preferable character possessed by an original cultivar is damaged is kept to a minimum.

CARRYING OUT THE INVENTION

Figure 1:
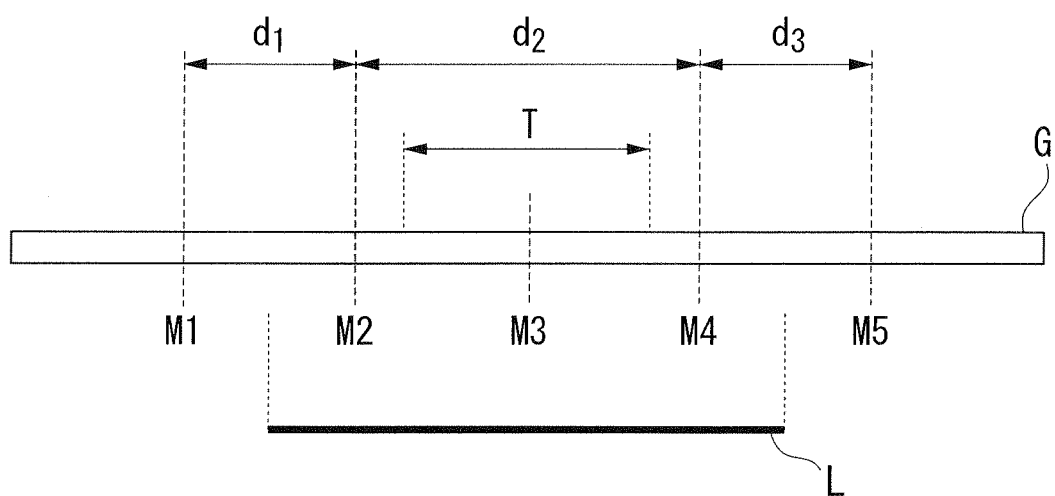
FIG. 1 is a view showing a target region T on a chromosome G of an original cultivar, a chromosome fragment G derived from a foreign cultivar to be introduced into this chromosome G, and DNA markers M1 to M5.

In the present invention, the chromosome fragment-substituted line means a line in which only a part of a chromosome of an original cultivar is substituted with a chromosome fragment derived from a foreign cultivar.

The foreign cultivar is not particularly limited as far as it is a cultivar other than an original cultivar, and may be a cultivar of a plant which is the same species as that of an original cultivar, may be a cultivar of a plant which is a different species from that of an original cultivar, and may be a cultivar other than a plant such as an animal and the like.

In the present invention, the cultivar means a population which is the same species of a plant, but can be clearly discriminated from other species in the same species in a certain character, due to different genetic construction.

In the present invention, the target region means a region in a chromosome of an original cultivar, which is aimed at being substituted with a chromosome fragment derived from a foreign cultivar. For example, in a cultivar of a plant for which genetic information has been sufficiently elucidated, such as rice, wheat, and *Arabidopsis*, a new cultivar improved in a character of an original cultivar can be created by substituting a particular chromosome region containing an objective character gene with a chromosome fragment derived from a foreign cultivar. Herein, the target region of an original cultivar is not particularly limited as far as it is a region corresponding to a region of a part substituted with a chromosome fragment derived from a foreign cultivar among a chromosome of a chromosome fragment-substituted line used as a parent individual, and the target region of the original cultivar may be one gene region, or may be a region containing two or more genes. For example, when a foreign cultivar is different species from that of an original cultivar, it is preferable that a region is one gene region. In addition, when a foreign cultivar is a related species of an original cultivar, such as when a foreign cultivar is other cultivar which is the same species of an original cultivar, the target region may be one gene region, or may be a region containing two or more genes.

This gene region may be only a translation region, or may be a region containing a non-translation region such as intron, a control region such as a promoter region and a terminator region in addition to the translation region.

The DNA markers in the present invention are not particularly limited as far as it can discriminate a chromosome derived from an original cultivar and a chromosome derived from a foreign cultivar, that is, it can detect a difference in a DNA sequence on a chromosome between the original cultivar and the foreign cultivar, and a DNA marker which is normally used in the gene analysis field can be used. These DNA markers may be, for example, a RFLP (Restriction Fragment Length Polymorphism) marker or a marker which can detect gene polymorphism such as SNP (Single Nucleotide Polymorphism), and can detect a difference in the repetition number of SSR (Simple Sequence Repeats).

Discrimination of an allele derived from the original cultivar and an allele derived from the foreign cultivar using these DNA markers can be performed by a conventional method. For example, PCR is performed as follows: employing a DNA extracted from each individual as a template; and using primers which can specifically hybridize with particular SNP and SSR. Then, by detecting the presence or the absence of the PCR product using an electrophoresis method or the like, each polymorphism of SNP and SSR can be discriminated between the original cultivar and the foreign cultivar. Alternatively, by detecting a pattern of a DNA fragment using an electrophoresis method or the like after a DNA extracted from each individual is treated with a restriction enzyme, each polymorphism can be discriminated similarly. Primers which can hybridize specifically with particular SNP and SSR can be designed by a conventional method using a primer design tool which is generally used, depending on a nucleotide sequence of SNP and SSR. In addition, designed primers can be synthesized using any of methods which are well-known in the present technical field.

As these DNA markers, the known DNA markers can be appropriately used. Alternatively, newly prepared DNA markers may be used. For example, when the known DNA markers regarding rice are used, SNP markers disclosed in Patent document 2, and DNA markers published in Rice Genome Research Program can be used. When the known DNA markers regarding barley are used, DNA markers published in GrainGenes: A Database for Triticeae and Avena, CR-EST:The IPK Crop EST Database can be used. When the known DNA markers regarding sorghum are used, DNA markers published in GRAMENE can be used. When the known DNA markers regarding wheat are used, DNA markers published in GrainGenes: A Database for Triticeae and Avena, WHEAT CAP can be used. When the known DNA markers regarding corn are used, DNA markers published in MaizeGDB can be used. In addition, DNA markers of other serials are disclosed in GRAMENE, and these can be also used.

First, the method of plant genome design of the present invention is explained.

The method of plant genome design of the present invention is a method of designing a genome of a plant in which one or plural target regions in a chromosome of an original cultivar is substituted with a chromosome fragment derived from a foreign cultivar, using a chromosome fragment-substituted line in which only a part of a chromosome of the original cultivar is substituted with a chromosome fragment derived from the foreign cultivar. In this method, DNA markers M1 to M5 satisfying the following requirement (i) are defined for every one target region. That is, in a substitution region in a chromosome of the original cultivar which contains this target region and is to be substituted with a chromosome fragment derived from the foreign cultivar, a genome is designed so that an end on an upstream side thereof is between DNA markers M1 and M2, and an end on a downstream side thereof is between DNA markers M4 and M5.

(i) The DNA marker M2 is defined at an end on an upstream of the target region, or upstream thereof. The DNA marker M1 is defined upstream of the DNA marker M2. The DNA marker M4 is defined at an end on a downstream side of the target region, or downstream thereof. The DNA marker M5 is defined downstream of the DNA marker M4. The DNA marker M3 is defined in the target region.

In the present invention, the upstream side means a short arm side of a chromosome, and the downstream means a long arm side of a chromosome.

By defining respective DNA markers M1 to M5 so as to satisfy the requirement (i), a length of a chromosome fragment derived from a foreign cultivar to be introduced into a chromosome of the original cultivar, that is, a substitution region in a chromosome of the original cultivar to be substituted with this chromosome fragment can be controlled. For this reason, by using the method of plant genome design of the present invention, a genome can be designed so that a gene derived from the foreign cultivar of a target is introduced into a chromosome of the original cultivar, while a probability that many other genes other than an objective gene are introduced into a chromosome of the original cultivar and a possibility that a gene other than an objective gene present in vicinity of a target region is substituted with a chromosome of the original cultivar derived from the foreign cultivar are kept to a minimum.

Respective DNA markers M1 to M5 can be designed based on the known genetic information of a plant species to which each cultivar belongs. Genetic information of each cultivar is available, for example, in NCBI (National center for Biotechnology Information) and DDBJ (DNA Data Bank of Japan) which are international nucleotide sequence database. Particularly, genetic information of each cultivar of rice is available in KOME (Knowledge-based Oryza Molecular biological Encyclopedia).

FIG. 1 is a view showing a target region T on a chromosome G of an original cultivar, a foreign cultivar-derived chromosome fragment L to be substituted, and DNA markers M1 to M5. An end on an upstream side of the foreign cultivar-derived chromosome fragment L, that is, an end on an upstream side of a substituent region in a chromosome of an original cultivar, which is substituted with the foreign cultivar-derived chromosome fragment L, is between the DNA markers M1 and M2. On the other hand, an end on a downstream side of the foreign cultivar-derived chromosome fragment L, that is, an end on a downstream side of a substitution region in a chromosome of an original cultivar, which is substituted with the foreign cultivar-derived chromosome fragment L, is between the DNA markers M4 and M5. For this reason, letting a distance between the DNA markers M1 and M2 to be d1, letting distance between the DNA markers M2 and M4 to be d2, and letting a distance between the DNA markers M4 and M5 to be d3, a length of the foreign cultivar-derived chromosome fragment L (length of substitution region) is expressed by following equation (1).

$$d2 \leq \text{length of foreign cultivar-derived chromosome fragment } L \leq d1 + d2 + d3 \quad \text{Equation (1):}$$

By setting the DNA marker M2 on an upstream side (a direction away from the target region T) of the chromosome G of the original cultivar, a length of the foreign cultivar-derived chromosome fragment L becomes long. On the other hand, by setting the DNA marker M2 on a downstream side (a direction approaching a target region T) of the chromosome G of the original cultivar, a length of the foreign cultivar-derived chromosome fragment L becomes short. Similarly, by setting the DNA marker M4 on a downstream side of the chromosome G of the original cultivar, a length of the foreign cultivar-derived chromosome fragment L becomes long and, by setting on an upstream side of the chromosome G of the original cultivar, a length of the foreign cultivar-derived chromosome fragment L becomes short.

In addition, when a distance d1 between the DNA markers M1 and M2 is long, a range in which an end on an upstream side of the foreign cultivar-derived chromosome fragment L can exist is widened. For this reason, it becomes difficult to define a length of the foreign cultivar-derived chromosome fragment L to be introduced. On the other hand, when this distance d1 is short, a range in which an end on an upstream side of the foreign cultivar-derived chromosome fragment L can exist is narrowed. For this reason, it becomes easy to define a length of the foreign cultivar-derived chromosome fragment L to be introduced.

Similarly, when a distance d3 between the DNA markers M4 and M5 is long, a range in which an end on a downstream side of the foreign cultivar-derived chromosome fragment L can exist is widened, and it becomes difficult to define the length of the foreign cultivar-derived chromosome fragment L to be introduced. When this distance d3 is short, a range in which an end on a downstream side of the foreign cultivar-derived chromosome fragment L can exist is narrowed, it become easy to define a length of the foreign cultivar-derived chromosome fragment L to be introduced.

As a length of a foreign cultivar-derived chromosome fragment L becomes longer, a possibility that genes presented on both sides of the target region of T are introduced into the original cultivar together with an objective gene presented in the target region T becomes higher. Introduction of a gene other than an objective gene into a chromosome of the original cultivar results in that a gene other than an objective gene presented in the original cultivar is substituted with the foreign cultivar-derived chromosome fragment L. As a result, there is a possibility that an excellent character possessed by the original cultivar is carelessly damaged. As a gene other than an objective gene to be introduced into a chromosome of the original cultivar is fewer, that is, as a length of the foreign cultivar-derived chromosome fragment L is closer to a length of the target region of T, a possibility that an excellent character of the original cultivar is substituted can be suppressed. Therefore, it is preferable that a length of the foreign cultivar-derived chromosome fragment L is closer to a length of the target region of T.

As the DNA markers M2 and M1 are closer to an end of an upper stream side of the target region T, and as the DNA markers M4 and M5 are closer to an end on a downstream side of the target region T, a length of foreign cultivar-derived chromosome fragment L becomes shorter. As a result, a chromosome region other than the target region T of the foreign cultivar-derived chromosome fragment L to be introduced into a chromosome of the original cultivar can be shorter. Then, it is preferable that the DNA marker M2 is defined in vicinity of an end of an upstream side of the target region T, and it is more preferable that the DNA marker M2 is on the same site as that of an end on an upstream side of the target region T. In addition, it is preferable that the DNA marker M1 is defined in vicinity on an upstream side of the DNA marker M2. On the other hand, it is preferable that the DNA marker M4 is defined in vicinity of an end on a downstream side of the target region of the T, and it is more preferable that the DNA marker M4 is on the same site as that of an end on a downstream side of the target region T. In addition, it is preferable that the DNA marker M5 is defined in vicinity on a downstream side of the DNA marker M4.

However, when a distance d1 between the DNA markers M1 and M2, a distance d2 between the DNA markers M2 and M4, and a distance d3 between the DNA markers M4 and M5 become too short, respectively, a recombination frequency of a chromosome becomes small. For this reason, as far as a size of a population from which a progeny individual is selected is not increased, it becomes difficult to obtain an objective progeny individual (a progeny individual in which recombination of a chromosome has occurred).

When a foreign cultivar is a related species of the original cultivar, DNA sequences of chromosomes of both cultivars have high homology. For this reason, even when a length of the foreign cultivar-derived chromosome fragment L is long and thereby a gene in vicinity of an objective gene (target regions T) is substituted with the foreign cultivar derived gene together with the objective gene, there is a possibility that an excellent character of the original cultivar is not damaged.

From the foregoing, it is preferable that defining of these DNA markers M1, M2, M4, and M5 is appropriately determined in view of a length of the target region T, whether the original cultivar and the foreign cultivar are related species or a distant species, and a size of a population to be selected.

Currently, although sequence information of a gene has been revealed, many genes whose function is unknown are present. In addition, even in a gene whose function is thought to be known, there are still many cases that the unknown new function is found by analysis thereafter. In principle, it is possible to elucidate the function of such the gene by introducing a chromosome fragment encoding the gene, whose function is unknown, into a chromosome of the original cultivar which has not inherently this gene and then comparing and studying a biological character such as physiological activity possessed by the resulting cultivar with that of the original cultivar. However, in a cultivar improvement method using the previous procedure such as the MAS method and the like, it is difficult to strictly control a chromosome fragment derived from the foreign cultivar to be introduced into the original cultivar. Therefore, information such as what a gene is encoded in addition to an objective gene in the introduced chromosome fragment, or what a gene was encoded in a chromosome region of the original cultivar lost by substitution with this chromosome fragment is unknown in many cases. For this reason, in the case of a cultivar having a genome designed so as to introduce a foreign cultivar-derived chromosome fragment by the previous method, it is very difficult to precisely assess whether a biological character different from that of the original cultivar is the function expressed by an introduced objective gene or not. In addition, even in the case where an objective character could be introduced, when other character has been also varied, it is difficult to determine that whether this variation is due to the unknown function of the introduced objective gene, or due to a gene different from this gene.

To the contrary, in a genome designed by the method of plant genome design of the present invention, a length of the foreign cultivar-derived chromosome fragment L, and a substitution region of the chromosome G of the original cultivar to be substituted with this foreign cultivar-derived chromosome fragment L can be more strictly defined than previously. For this reason, in the case of a cultivar having a genome designed so as to introduce the foreign cultivar-derived chromosome fragment L using the method of plant genome design of the present invention, it becomes possible to assess a character introduced into the original cultivar by this foreign cultivar-derived chromosome fragment L at a higher precision than previously. Therefore, the method of plant genome design of the present invention can be suitably used also in analysis of the gene function.

Then, the method of creating a new cultivar of a present invention will be explained. The method of creating a new cultivar of the present invention utilizes the method of plant genome design of the present invention. Specifically, there are following four kinds (first to fourth) of production methods.

In the method of creating a new cultivar of the present invention, the original cultivar is not particularly limited as far as it is a plant cultivar, but it is preferable that the original cultivar is such as Poaceae, Fabaceae, Brassicaceae, Rutaceae, Malvaceae, Asteraceae, Amaranthaceae, Euphorbiaceae, Convolvuaceae, or Liliaceae. As a plant of Poaceae, for example, rice, corn, sorghum bicolor, wheat, barley, rye, Japanese barnyard millet, and sorghum are preferable. In addition, as a plant of Fabaceae, for example, peanut, chick-pea, soybean max, common bean, bird's-foot trefoil, and medicago are preferable. As a plant of Brassicacae, for example, thale-cross, oilseed rape, shepherd's-purse, radish, cabbage, and wasabi are preferable. As a plant of Rutaceae, for example, orange is preferable. As a plant of Malvaceae, for example, cotton is preferable. As a plant of Asteraceae, for example, helianthus, lettuce, Zinnia-elegans, tomato, potato, chili pepper, and tobacco are preferable. As a plant of Amaranthaceae, for example, sugar beet is preferable and, as a plant of Euphorbiaceae, for example, Euphorbia esula, and cassaya are preferable. As a plant of Convolvuaceae, for example, Japanese morning glory is preferable and, as a plant of Liliaceae, for example, onion is preferable.

In the method of creating a new cultivar of the present invention, it is preferable that the chromosome fragment-substituted line is, particularly, a line of an autogamous plant or a self-fertile plant because an uncertain element in genome design can be reduced. Herein, self-propagation means mating using a self as a mate. Specifically, in the case of a hermaphrodite plant, self-propagation is that an ovule is fertilized by autogamy to produce a seed, that is, selfmating.

Particularly, the method of creating a new cultivar of the present invention can create a new cultivar relatively safely and stably without using a gene recombinant method. For this reason, the chromosome fragment-substituted line used in the present invention is preferably such that an edible plant is the original cultivar, more preferably such that rice, wheat, corn, or soybean is the original cultivar, and further preferably such that rice is the original cultivar. A rice cultivar is preferably Koshihikari, Habataki, or IR64, particularly preferably Koshihikari.

The chromosome fragment-substituted line used in the present invention may be created by the conventional method, or may be available from an organization such as National Institute of Agrobiological Sciences Rice Genome Resource Center.

In the first method of creating a new cultivar of the present invention, the following steps (1-1) to (1-6) are performed for every one target region on one or plural target regions in a chromosome of an original cultivar, using a chromosome fragment-substituted line in which only a part of a chromosome of an original cultivar is substituted with a chromosome fragment derived from a foreign cultivar.

(1-1) A step of defining a DNA marker M2 at an end on an upstream side of a target region, or upstream thereof; a step of defining a DNA marker M1 upstream of the DNA marker M2; a step of defining a DNA marker M4 at an end on a downstream side of the target region, or downstream thereof; a step of defining a DNA marker M5 downstream of the DNA marker M4; a step of defining a DNA marker M3 in the target region.

(1-2) A step of mating a chromosome fragment-substituted line and an original cultivar to obtain a progeny individual in which the DNA marker M3 is a hetero-chromosome region of an allele derived from the original cultivar and an allele derived from a foreign cultivar.

(1-3) A step of self-mating the progeny individual obtained in the step (1-2) to obtain a progeny individual.

(1-4) A step of selecting a progeny individual in which the DNA marker M1 is a homo-chromosome region of an allele derived from the original cultivar, and the DNA markers M2 and M3 are a hetero-chromosome region of an allele derived from the original cultivar and an allele derived from the foreign cultivar, from the progeny individual obtained in the step (1-3); or a progeny individual obtained by backcrossing the progeny individual obtained in the step (1-3).

(1-5) A step of self-mating the progeny individual selected in the step (1-4) to obtain a progeny individual.

(1-6) A step of selecting a progeny individual in which the DNA markers M1 and M5 are a homo-chromosome region of an allele derived from the original cultivar, and the DNA markers M2, M3 and M4 are a homo-chromosome region of an allele derived from the foreign cultivar from the progeny individual obtained in the step (1-5); or a progeny individual obtained by self-mating the progeny individual obtained in the step (1-5).

Each step will be explained below.

First, as the step (1-1), a DNA marker M2 is defined at an end on an upstream side of a target region in a chromosome of an original cultivar, or upstream thereof, and a DNA marker M1 is defined upstream of the DNA marker M2. On the other hand, a DNA marker M4 is defined at an end on a downstream side of this target region, or downstream thereof, and a DNA marker M5 is defined downstream of the DNA marker M4. And, in this target region, a DNA marker M3 is defined. That is, respective DNA markers M1, M2, M4, M5 are defined so that an end on an upstream side of a chromosome fragment derived from a foreign cultivar to be introduced into a chromosome region (region containing a target region) of the original cultivar by substitution is between DNA markers M1 and M2, and an end on a downstream side thereof is between the DNA markers M4 and M5.

Specifically, defining of respective DNA markers M1 to M5 is the same as that of the method of plant genome design of the present invention.

By defining the DNA markers M1 to M5 like this, in creating a new cultivar, a length of a chromosome fragment derived from the foreign cultivar to be introduced into a chromosome of the original cultivar can be controlled. As a result, a gene other than an objective gene can be effectively suppressed from being introduced into a chromosome of the original cultivar. Further, it becomes possible to effectively suppress a gene other than an objective gene present in vicinity of the target region from being substituted with a chromosome of the original cultivar derived from the foreign cultivar.

Then, as the step (1-2), a chromosome fragment-substituted line and the original cultivar are mated to obtain a progeny individual in which the DNA marker M3 is a hetero-chromosome region of an allele derived from the original cultivar and an allele derived from the foreign cultivar. The chromosome fragment-substituted line as a seed parent, and the original cultivar as a pollen parent may be mated, or the original cultivar as a seed parent and the chromosome fragment-substituted line as a pollen parent may be mated.

Usually, in mating, genes possessed by a parent individual are randomly arranged in a gamete. For this reason, although a progeny individual selected by the DNA marker has a gene encoding an objective character, how other gene regions are changed from the parent individual is unknown. For this reason, it is difficult to determine that a phenotypic character of the resulting progeny individual is due to a chromosome region linked with the DNA marker, or influence of a gene present in other chromosome region.

In the present invention, the chromosome fragment-substituted line and the original cultivar of this chromosome fragment-substituted line are used as the parent individual. In this chromosome fragment-substituted line, other chromosome regions other than a chromosome fragment derived from a foreign cultivar all have the same genes as those of the original cultivar. Therefore, a chromosome region of the resulting progeny individual is such that chromosome regions other than a chromosome fragment derived from the foreign cultivar all become to have the same genes as those of the original cultivar. For this reason, in this progeny individual, it becomes possible to easily determine the influence by the chromosome fragment derived from the foreign cultivar.

In the method of creating a new cultivar of the present invention, mating may be natural mating, but since a seed parent and a pollen parent can be assuredly identified, artificial mating is preferable. Herein, the artificial mating method is not particularly limited as far as it is a method which can make a pistil of a seed parent receive a pollen collected from a pollen parent to fertilize it, but can be performed by the conventional method.

As the step (1-3), the progeny individual obtained in the step (1-2) is self-mated to obtain a progeny individual. Thereafter, as the step (1-4), a progeny individual in which the DNA marker M1 is a homo-chromosome region of an allele derived from the original cultivar, and the DNA markers M2 and M3 are a hetero-chromosome region of an allele of the original cultivar and an allele derived from the foreign cultivar is selected, from the progeny individual obtained in the step (1-3); or a progeny individual obtained by backcrossing the progeny individual obtained in the step (1-3).

Figure 2A:
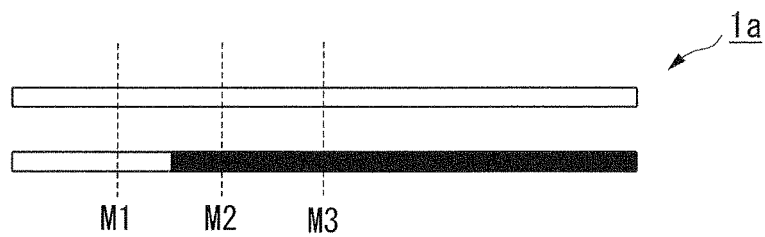
FIG. 2A is a view showing a chromosome region of a progeny individual preferable in a step (1-4), among progeny individuals obtained step (1-3) in a first method of creating a new cultivar of the present invention. In the figure, a non-filled bold line shows an allele derived from an original cultivar, and a filled bold line shows an allele derived from a foreign cultivar, respectively.
Figure 2B:
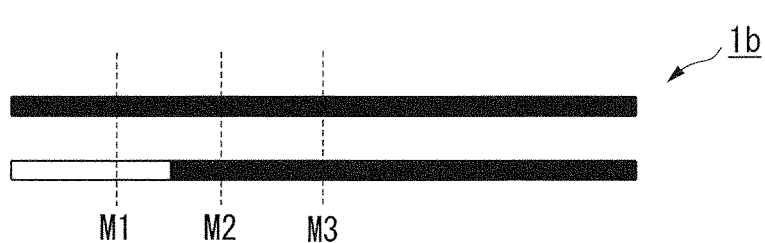
FIG. 2B is a view showing a chromosome region of a progeny individual preferable in a step (1-4), among progeny individuals obtained in a step (1-3) in the same method. In the figure, a non-filled bold line shows an allele derived from an original cultivar, and a filled bold line shows an allele derived from a foreign cultivar, respectively.
Figure 2C:
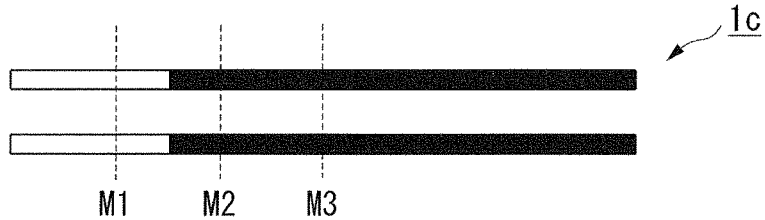
FIG. 2C is a view showing a chromosome region of a progeny individual preferable in a step (1-4), among progeny individuals obtained in a step (1-3) in the same method. In the figure, a non-filled bold line shows an allele derived from an original cultivar, and a filled bold line shows an allele derived from a foreign cultivar, respectively.

FIG. 2A to FIG. 2C are views showing a chromosome region of a progeny individual preferable in the step (1-4) among progeny individuals obtained in the step (1-3). In the figure, a non-filled bold line shows an allele derived from the original cultivar, and a filled bold line shows an allele derived from the foreign cultivar. First, from the progeny individual obtained in the step (1-3), a progeny individual (1a) in which the DNA marker M1 is a homo-chromosome region of an allele derived from the original cultivar, and the DNA markers M2 and M3 are a hetero-chromosome region; a progeny individual (1b) in which the DNA marker M1 is a hetero-chromosome region, and the DNA markers M2 and M3 are a homo-chromosome region of an allele derived from the foreign cultivar; a progeny individual (1c) in which the DNA marker M1 is a homo-chromosome region of an allele derived from the original cultivar, and the DNA markers M2 and M3 are a homo-chromosome region of an allele derived from the foreign cultivar; are selected, respectively. Herein, the progeny individual (1a) is a progeny individual finally selected in the step (1-4). The progeny individual (1b) and the progeny individual (1c) are further backcrossed with an individual of each original cultivar, and then the progeny individual (1a) can be selected from the resulting progeny individual.

Then, as the step (1-5), by self-mating the progeny individual (1a) selected in the step (1-4) like this, a progeny individual is obtained. Thereafter, as the step (1-6), a progeny individual in which the DNA markers M1 and M5 are a homo-chromosome region of an allele derived from the original cultivar, and the DNA markers M2, M3, and M4 are a homo-chromosome region of an allele derived from the foreign cultivar is selected, from the progeny individual obtained in the step (1-5); or a progeny individual obtained by self-mating the progeny individual obtained in the step (1-5).

Figure 2D:
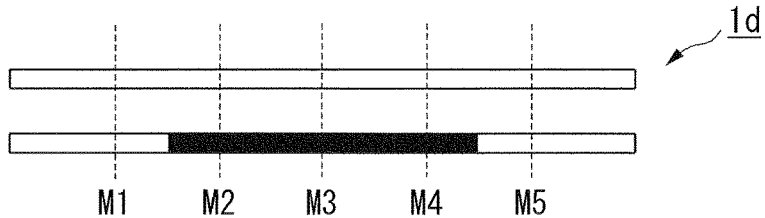
FIG. 2D is a view showing a chromosome region of a progeny individual preferable in a step (1-6), among progeny individuals obtained in a step (1-5) in the same method. In the figure, a non-filled bold line shows an allele derived from an original cultivar, and a filled bold line shows an allele derived from a foreign cultivar, respectively.
Figure 2E:
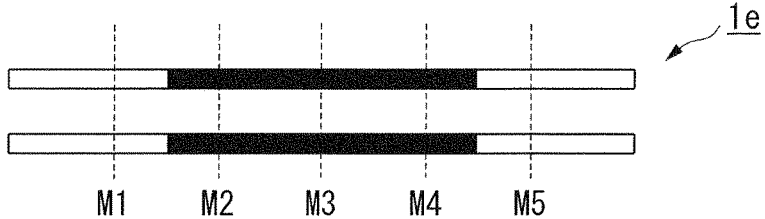
FIG. 2E is a view showing a chromosome region of a progeny individual preferable in a step (1-6), among progeny individuals obtained in a step (1-5) in the same method. In the figure, a non-filled bold line shows an allele derived from an original cultivar, and a filled bold line shows an allele derived from a foreign cultivar, respectively.
Figure 2F:
FIG. 2F is a view showing a chromosome region of a progeny individual preferable in a step (1-6), among progeny individuals obtained in a step (1-5) in the same method. In the figure, a non-filled bold line shows an allele derived from an original cultivar, and a filled bold line shows an allele derived from a foreign cultivar, respectively.

FIG. 2D to FIG. 2F are views showing a chromosome region of a progeny individual preferable in the step (1-6) among progeny individuals obtained in the step (1-5). In the figures, a non-filled bold line shows an allele derived from the original cultivar, and a filled bold line shows an allele derived from the foreign cultivar. First, from the progeny individual obtained in the step (1-5), a progeny individual (1d) in which the DNA markers M1 and M5 are a homo-chromosome region of an allele derived from the original cultivar, and the DNA markers M2, M3 and M4 are a hetero-chromosome region; a progeny individual (1e) in which the DNA markers M1 and M5 are a homo-chromosome region of an allele derived from the original cultivar, and the DNA markers M2, M3 and M4 are a homo-chromosome region of an allele derived from the foreign cultivar; a progeny individual (1f) in which the DNA marker M1 is a homo-chromosome region of an allele derived from the original cultivar, the DNA markers M2, M3 and M4 are a homo-chromosome region of an allele derived from the foreign cultivar, and the DNA marker M5 is a hetero-chromosome region; are selected, respectively. Herein, the progeny individual (1e) is an objective new cultivar created by the first method of creating a new cultivar of the present invention, in which an end on an upstream side of a foreign cultivar-derived chromosome fragment L is between the DNA markers M1 and M2, and an end on a downstream side thereof is between the DNA markers M4 and M5. The progeny individual (1d) and the progeny individual (1f) are a further self-mated, respectively, and the progeny individual (1e) can be selected from the resulting progeny individual.

Alternatively, for determining both ends of the target region, after an end on an upstream side of the foreign cultivar-derived chromosome fragment to be introduced is determined, an end of a downstream side may be determined like the first method of creating a new cultivar of the present invention, or after an end of a downstream side is determined, an end on an upstream side may be determined like a second method of creating a new cultivar of the present invention described later.

In a second method of creating a new cultivar of the present invention, the following steps (2-1) to (2-6) are performed for every one target region on one or plural target regions in a chromosome of an original cultivar, using a chromosome fragment-substituted line in which only a part of a chromosome of the original cultivar is substituted with a chromosome fragment derived from a foreign cultivar.

(2-1) A step of defining a DNA marker M2 at an end on an upstream side of a target region, or upstream thereof; a step of defining a DNA marker M1 upstream of the DNA marker M2; a step of defining a DNA marker M4 at an end on a downstream side of a target region, or a downstream thereof; a step of defining a DNA marker M5 downstream of the DNA marker M4; a step of defining a DNA marker M3 in the target region.

(2-2) A step of mating a chromosome fragment-substituted line and an original cultivar to obtain a progeny individual in which the DNA marker M3 is a hetero-chromosome region of an allele derived from an original cultivar and an allele derived from a foreign cultivar.

(2-3) A step of self-mating the progeny individual obtained in the step (2-2) to obtain a progeny individual.

(2-4) A step of selecting a progeny individual in which the DNA marker M5 is a homo-chromosome region of an allele derived from the original cultivar, and the DNA markers M3 and M4 are a hetero-chromosome region of an allele derived from the original cultivar and an allele derived from the foreign cultivar, from the progeny individual obtained in the step (2-3); or a progeny individual obtained by backcrossing the progeny individual obtained in the step (2-3).

(2-5) A step of self-mating the progeny individual selected in the step (2-4) to obtain a progeny individual.

(2-6) A step of selecting a progeny individual in which the DNA markers M1 and M5 are a homo-chromosome region of an allele derived from the original cultivar, and the DNA markers M2, M3 and M4 are a homo-chromosome region of an allele derived from the foreign cultivar, from the progeny individual obtained in the step (2-5); or a progeny individual obtained by self-mating the progeny individual obtained in the step (2-5).

The steps (2-1) to (2-3) are the same as the steps (1-1) to (1-3) of the first method of creating a new cultivar of the present invention, respectively.

Figure 3A:
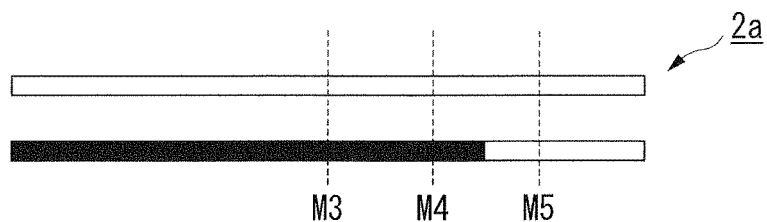
FIG. 3A is a view showing a chromosome region of a progeny individual preferable in a step (2-4), among progeny individuals obtained in a step (2-3) of a second method of creating a new cultivar of present invention. In the figure, a non-filled bold line shows an allele derived from an original cultivar, and a filled bold line shows an allele derived from a foreign cultivar, respectively.
Figure 3B:
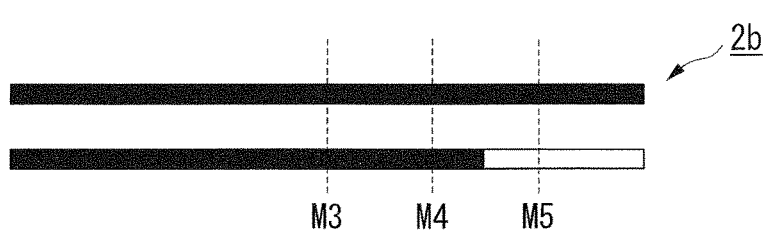
FIG. 3B is a view showing a chromosome region of a progeny individual preferable in a step (2-4), among progeny individuals obtained in a step (2-3) in the same method. In the figure, a non-filled bold line shows an allele derived from an original cultivar, and a filled bold line shows an allele derived from a foreign cultivar, respectively.
Figure 3C:
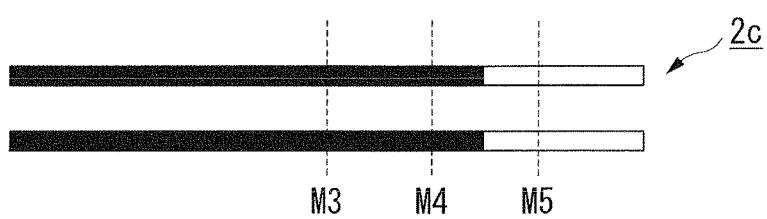
FIG. 3C is a view showing a chromosome region of a progeny individual preferable in a step (2-4), among progeny individuals obtained in a step (2-3) in the same method. In the figure, a non-filled bold line shows an allele derived from an original cultivar, and a filled bold line shows an allele derived from a foreign cultivar, respectively.

FIG. 3A to FIG. 3C are views showing a chromosome region of a progeny individual preferable in the step (2-4) among progeny individuals obtained in the step (2-3). In the figures, a non-filled bold line shows an allele derived from an original cultivar, and a filled bold line shows an allele derived from a foreign cultivar, respectively. First, from the progeny individual obtained in the step (2-3), a progeny individual (2a) in which the DNA marker M5 is a homo-chromosome region of an allele derived from the original cultivar, and the DNA markers M4 and M3 are a hetero-chromosome region; a progeny individual (2b) in which the DNA marker M5 is a hetero-chromosome region, and the DNA markers M4 and M3 are a homo-chromosome region of an allele derived from the foreign cultivar; a progeny individual (2c) in which the DNA marker M5 is a homo-chromosome region of an allele derived from the original cultivar, and the DNA markers M4 and M3 are a homo-chromosome region of an allele derived from the foreign cultivar; are selected, respectively. Herein, the progeny individual (2a) is a progeny individual finally selected in the step (2-4). The progeny individual (2b) and the progeny individual (2c) are further backcrossed with an individual of each original cultivar, and the progeny individual (2a) can be selected from the resulting progeny individual.

Figure 3D:
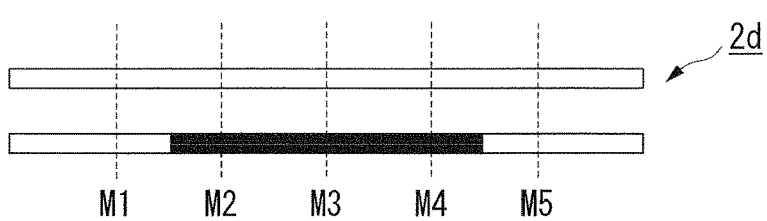
FIG. 3D is a view showing a chromosome region of a progeny individual preferably in a step (2-6), among progeny individuals obtained in a step (2-5) in the same method. In the figure, a non-filled bold line shows an allele derived from an original cultivar, and a filled bold line shows an allele derived from a foreign cultivar, respectively.
Figure 3E:
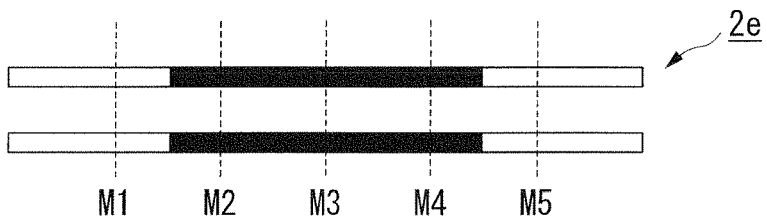
FIG. 3E is a view showing a chromosome region of a progeny individual preferable in a step (2-6), among progeny individuals obtained in a step (2-5) in the same method. In the figure, a non-filled bold line shows an allele derived from an original cultivar, and a filled bold line shows an allele derived from a foreign cultivar, respectively.
Figure 3F:
FIG. 3F is a view showing a chromosome region of a progeny individual preferable in a step (2-6), among progeny individuals obtained in a step (2-5) in the same method. In the figure, a non-filled bold line shows an allele derived from an original cultivar, and a filled bold line shows an allele derived from a foreign cultivar, respectively.
Figure 4A:
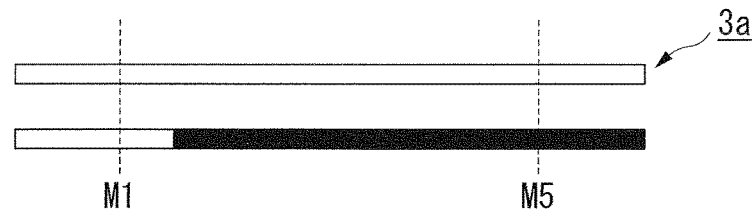
FIG. 4A is a view showing a chromosome region of a progeny individual preferable in a step (3-4), among progeny individuals obtained in a step (3-3) in a third method of creating a new cultivar of the present invention. In the figure, a non-filled bold line shows an allele derived from an original cultivar, and a filled bold line shows an allele derived from a foreign cultivar, respectively.
Figure 4B:
FIG. 4B is a view showing a chromosome region of a progeny individual preferable in a step (3-4), among progeny individuals obtained in a step (3-3) in the same method. In the figure, a non-filled bold line shows an allele derived from an original cultivar, and a filled bold line shows an allele derived from a foreign cultivar, respectively.
Figure 4C:
FIG. 4C is a view showing a chromosome region of a progeny individual preferable in a step (3-4), among progeny individuals obtained in a step (3-3) in the same method. In the figure, a non-filled bold line shows an allele derived from an original cultivar, and a filled bold line shows an allele derived from a foreign cultivar, respectively.
Figure 4D:
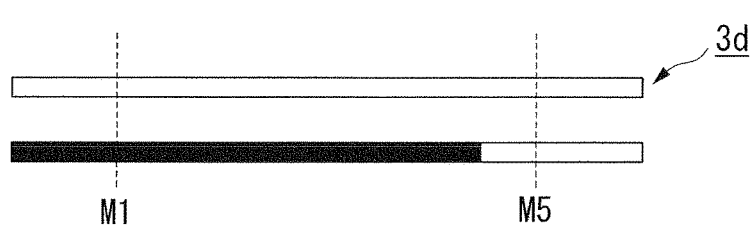
FIG. 4D is a view showing a chromosome region of a progeny individual preferable in a step (3-4), among progeny individuals obtained in a step (3-3) in the same method. In the figure, a non-filled bold line shows an allele derived from an original cultivar, and a filled bold line shows an allele derived from a foreign cultivar, respectively.
Figure 4E:
FIG. 4E is a view showing a chromosome region of a progeny individual preferable in a step (3-4), among progeny individuals obtained in a step (3-3) in the same method. In the figure, a non-filled bold line shows an allele derived from an original cultivar, and a filled bold line shows an allele derived from a foreign cultivar, respectively.
Figure 4F:
FIG. 4F is a view showing a chromosome region of a progeny individual preferable in a step (3-4), among progeny individuals obtained in a step (3-3) in the same method. In the figure, a non-filled bold line shows an allele derived from an original cultivar, and a filled bold line shows an allele derived from a foreign cultivar, respectively.

FIG. 3D to FIG. 3F are views showing a chromosome region of a progeny individual preferable in the step (2-6) among progeny individuals obtained in the step (2-5). In the figures, a non-filled bold line shows an allele derived from the original cultivar, and a filled bold line shows an allele derived from the foreign cultivar. First, from the progeny individual obtained in the step (2-5), a progeny individual (2d) in which the DNA markers M1 and M5 are a homo-chromosome region of an allele derived from the original cultivar, and the DNA markers M2, M3 and M4 are a hetero-chromosome region; a progeny individual (2e) in which the DNA markers M1 and M5 are a homo-chromosome region of an allele derived from the original cultivar, and the DNA markers M2, M3 and M4 are a homo-chromosome region of an allele derived from the foreign cultivar; a progeny individual (2f) in which the DNA marker M5 is a homo-chromosome region of an allele derived from the original cultivar, the DNA markers M2, M3 and M4 are a homo-chromosome region of an allele derived from the foreign cultivar, and the DNA markers M1 is a hetero-chromosome region; are selected, respectively. Herein, the progeny individual (2e) is an objective new cultivar created by the second method of creating a new cultivar of the present invention, in which an end on an upstream side of a foreign cultivar-derived chromosome fragment L is between the DNA markers M1 and M2, and an end on a downstream side thereof is between the DNA markers M4 and M5. The progeny individual (2d) and the progeny individual (2f) are further self-mated, respectively, and then the progeny individual (2e) can be selected from the resulting progeny individual.

Alternatively, for determining both ends of the target region, after a one side end of the foreign cultivar-derived chromosome fragment to be introduced is determined, other end may be determined like the first or second method of creating an new cultivar of the present invention, or ends on both sides may be determined first like a third method of creating a new cultivar of the present invention described later.

In a third method of creating a new cultivar of the present invention, the following steps (3-1) to (3-6) are performed for every one target region on one or plural target regions in a chromosome of an original cultivar, using a chromosome fragment-substituted line in which only a part of a chromosome of the original cultivar is substituted with a foreign cultivar-derived chromosome fragment.

(3-1) A step of defining a DNA marker M2 at an end on an upstream side of a target region, or upstream thereof; a step of defining a DNA marker M1 upstream of the DNA marker M2; a step of defining a DNA marker M4 at ant end on a downstream side of the target region, or the downstream thereof; a step of defining a DNA marker M5 downstream of the DNA maker M4; a step of defining a DNA marker M3 in the target region.

(3-2) A step of mating a chromosome fragment-substituted line and an original cultivar to obtain a progeny individual in which the DNA marker M3 is a hetero-chromosome region of an allele derived from the original cultivar and an allele derived from a foreign cultivar.

(3-3) A step of self-mating the progeny individual obtained in the step (3-2) to obtain a progeny individual.

(3-4) A step of selecting a progeny individual in which any one of the DNA markers M1 and M5 is a homo-chromosome region of an allele derived from the original cultivar, and the other is a hetero-chromosome region of an allele derived from the original cultivar and an allele derived from the foreign cultivar, from the progeny individual obtained in the step (3-3); or a progeny individual obtained by backcrossing the progeny individual obtained in the step (3-3).

(3-5) A step of self-mating the progeny individual selected in the step (3-4) to obtain a progeny individual.

(3-6) A step of selecting a progeny individual in which the DNA markers M1 and M5 are a homo-chromosome region of an allele derived from the original cultivar, and the DNA markers M2, M3 and M4 are a homo-chromosome region of an allele derived from the foreign cultivar, from the progeny individual obtained in the step (3-5); or a progeny individual obtained by self-mating the progeny individual obtained in the step (3-5).

The steps (3-1) to (3-3) are the same as the steps (1-1) to (1-3) of the first method of creating a new cultivar of the present invention.

As the step (3-4), a progeny individual in which any one of the DNA markers M1 and M5 is a homo-chromosome region of an allele derived from the original cultivar, and the other is a hetero-chromosome region of an allele derived from the original cultivar and an allele derived from a foreign cultivar, from the progeny individual obtained in the step (3-3); or a progeny individual obtained by backcrossing the progeny individual obtained in the step (3-3). That is, from among progeny individuals obtained in the step (3-3), an objective progeny individual may be selected, or after a progeny individual in which in at least any one of alleles, a recombination point about the original cultivar-derived allele region and the foreign cultivar-derived allele region is present between the DNA markers M1 and M5 is selected from progeny individuals obtained in the step (3-3), an objective progeny individual may be selected from among progeny individuals obtained by backcrossing this progeny individual.

FIG. 4A to FIG. 4F are views showing a chromosome region of a progeny individual preferable in the step (3-4) among progeny individuals obtained in the step (3-3). In the figures, a non-filled bold line shows an allele derived from the original cultivar, and a filled bold line shows an allele derived from the foreign cultivar, respectively. First, from the progeny individual obtained in the step (3-3), a progeny individual (3a) in which the DNA marker M1 is a homo-chromosome region of an allele derived from the original cultivar, and the DNA marker M5 is a hetero-chromosome region; a progeny individual (3b) in which the DNA marker M1 is a hetero-chromosome region, and the DNA marker M5 is a homo-chromosome region of an allele derived from the foreign cultivar; a progeny individual (3c) in which the DNA marker M1 is a homo-chromosome region of an allele derived from the original cultivar, and the DNA marker M5 is a homo-chromosome region of an allele derived from the foreign cultivar; a progeny individual (3d) in which the DNA marker M1 is a hetero-chromosome region, and the DNA marker M5 is a homo-chromosome region of an allele derived from the original cultivar; a progeny individual (3e) in which the DNA marker M1 is a homo-chromosome region of an allele derived from the foreign cultivar, and the DNA marker M5 is a hetero-chromosome region; a progeny individual (3f) in which the DNA marker M1 is a homo-chromosome region of an allele derived from the foreign cultivar, and the DNA marker M5 is a homo-chromosome region of an allele derived from the original cultivar; are selected, respectively. Herein, the progeny individual (3a) or (3d) is a progeny individual finally selected in the step (3-4). The progeny individual (3b), (3c), (3e) or (3f) is further backcrossed with an individual of each original cultivar, and the progeny individual (3a) or (3d) can be selected from the resulting progeny individual.

Then, as the step (3-5), by self-mating the progeny individual (3a) or (3d) selected in the step (3-4) like this, a progeny individual is obtained. Thereafter, as the step (3-6), a progeny individual in which the DNA markers M1 and M5 are a homo-chromosome region of an allele derived from the original cultivar, and the DNA markers M2, M3 and M4 are a homo-chromosome region of an allele derived from the foreign cultivar is selected, from the progeny individual obtained in the step (3-5); or a progeny individual obtained by self-mating the progeny individual obtained in the step (3-5).

Figure 5A:
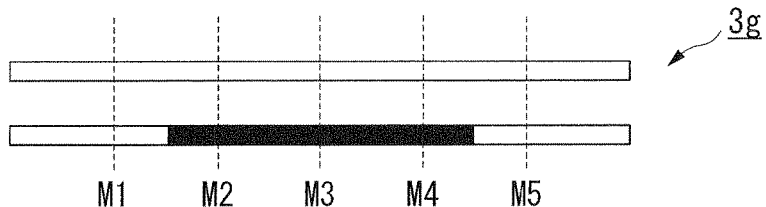
FIG. 5A is a view showing a chromosome region of a progeny individual preferable in a step (3-6), among progeny individuals obtained in a step (3-5) in a third method of creating a new cultivar of the present invention. In the figure, a non-filled bold line shows an allele derived from an original cultivar, and a filled bold line shows an allele derived from a foreign cultivar, respectively.
Figure 5B:
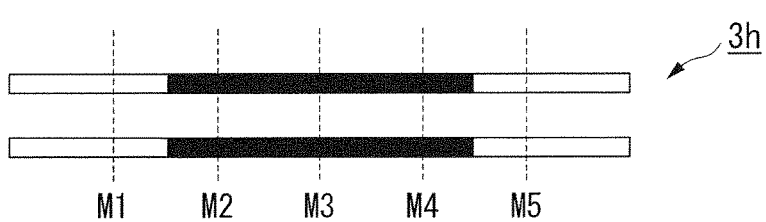
FIG. 5B is a view showing a chromosome region of a progeny individual preferable in a step (3-6), among progeny individuals obtained in a step (3-5) in the same method. In the figure, a non-filled bold line shows an allele derived from an original cultivar, and a filled bold line shows an allele derived from a foreign cultivar, respectively.
Figure 5C:
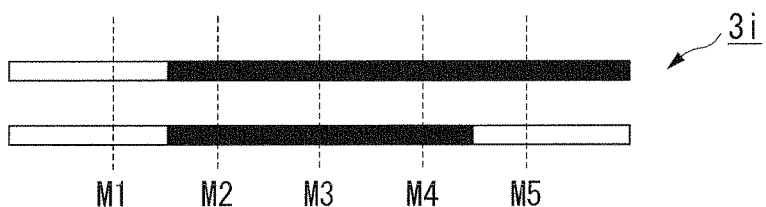
FIG. 5C is a view showing a chromosome region of a progeny individual preferable in a step (3-6), among progeny individuals obtained in a step (3-5) in the same method. In the figure, a non-filled bold line shows an allele derived from an original cultivar, and a filled bold line shows an allele derived from a foreign cultivar, respectively.

FIG. 5A to FIG. 5C are views showing a chromosome region of a progeny individual preferable in the step (3-6), among the case where the progeny individual obtained in the step (3-4) is (3a). In the figures, a non-filled bold line shows an allele derived from the original cultivar, and a filled bold line shows an allele derived from the foreign cultivar. First, from progeny individuals obtained in the step (3-5), a progeny individual (3g) in which the DNA markers M1 and M5 are a homo-chromosome region of an allele derived from the original cultivar, and the DNA markers M2, M3 and M4 are a hetero-chromosome region; a progeny individual (3h) in which the DNA markers M1 and M5 are a homo-chromosome region of an allele derived from the original cultivar, and the DNA markers M2, M3 and M4 are a homo-chromosome region of an allele derived from the foreign cultivar; a progeny individual (3i) in which the DNA marker M1 is a homo-chromosome region of an allele derived from the original cultivar, the DNA markers M2, M3 and M4 are a homo-chromosome region of an allele derived from the foreign cultivar, and the DNA marker M5 is a hetero-chromosome region; are selected, respectively. Herein, the progeny individual (3h) is an objective new cultivar created by the third method of creating a new cultivar of the present invention, an end on an upstream side of a foreign cultivar-derived chromosome fragment L is between the DNA markers M1 and M2, and an end on a downstream side is between the DNA markers M4 and M5. The progeny individual (3g) and the progeny individual (3i) are further self-mated, respectively, and the progeny individual (3h) can be selected from the resulting progeny individual.

Figure 5D:
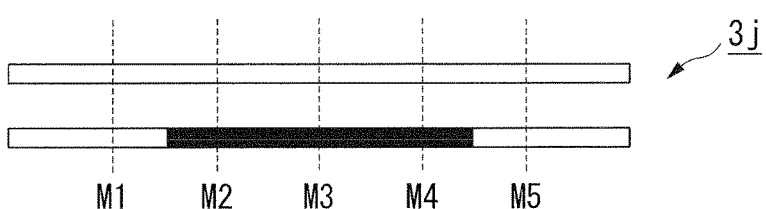
FIG. 5D is a view showing a chromosome region of a progeny individual preferable in a step (3-6), among progeny individuals obtained in a step (3-5) in the same method. In the figure, a non-filled bold line shows an allele derived from an original cultivar, and a filled bold line shows an allele derived from a foreign cultivar, respectively.
Figure 5E:
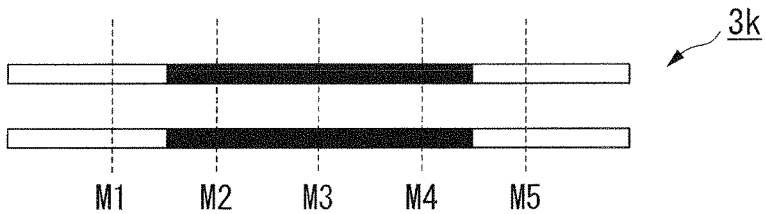
FIG. 5E is a view showing a chromosome region of a progeny individual preferable in a step (3-6), among progeny individuals obtained in a step (3-5) in the same method. In the figure, a non-filled bold line shows an allele derived from an original cultivar, and a filled bold line shows an allele derived from a foreign cultivar, respectively.
Figure 5F:
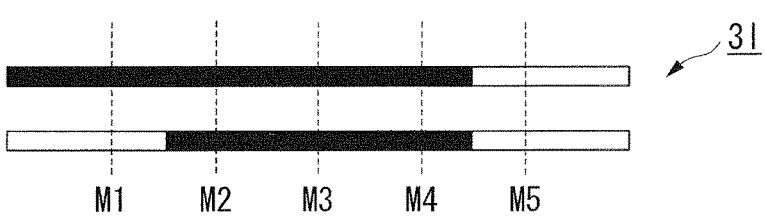
FIG. 5F is a view showing a chromosome region of a progeny individual preferable in a step (3-6), among progeny individuals obtained in a step (3-5) in the same method. In the figure, a non-filled bold line shows an allele derived from an original cultivar, and a filled bold line shows an allele derived from a foreign cultivar, respectively.

FIG. 5D to FIG. 5F are views showing a chromosome region of a chromosome individual preferable in the step (3-6), among the case where the progeny individual obtained in the step (3-4) is (3d). In the figures, a non-filled bold line shows an allele derived from the original cultivar, and a filled bold line shows an allele derived from the foreign cultivar. First, from progeny individuals obtained in the step (3-5), a progeny individual (3j) in which the DNA markers M1 and M5 are a homo-chromosome region of an allele derived from the original cultivar, and the DNA markers M2, M3 and M4 are a hetero-chromosome region; a progeny individual (3k) in which the DNA markers M1 and M5 are a homo-chromosome region of an allele derived from the original cultivar, and the DNA markers M2, M3 and M4 are a homo-chromosome region of an allele derived from the foreign cultivar; a progeny individual (3l) in which the DNA marker M5 is a homo-chromosome region of an allele derived from the original cultivar, the DNA markers M2, M3 and M4 are a homo-chromosome region of an allele derived from the foreign cultivar, and the DNA marker M1 is a hetero-chromosome; are selected, respectively. Herein, the progeny individual (3k) is an objective new cultivar created by the third method of creating a new cultivar of the present invention, an end on an upstream side of a foreign cultivar-derived chromosome fragment L is between the DNA markers M1 and M2, and an end on a downstream side is between the DNA markers M4 and M5. The progeny individual (3j) and (3l) are further self-mated, respectively, and the progeny individual (3k) can be selected from the resulting progeny individual.

In the third method of creating a new cultivar of the present invention, even when all progeny individuals (3a) to (3f) shown in FIG. 4A to FIG. 4F are selected in the step (3-4), by performing the following steps (3-7-1) and (3-7-2) before the step (3-5), an objective progeny individual in which the DNA markers M1 and M5 are a homo-chromosome individual of an allele derived from the original cultivar, and the DNA markers M2, M3 and M4 are a homo-chromosome region of an allele derived from the foreign cultivar can be obtained.

(3-7-1) A step of obtaining a progeny individual by self-mating the progeny individual selected in the step (3-4).
(3-7-2) A step of selecting (ii-1) a progeny individual in which the DNA marker M1 is a homo-chromosome region of an allele derived from the original cultivar, and the DNA markers M2 and M3 are a hetero-chromosome region of an allele derived from the original cultivar and an allele derived from the foreign cultivar; or (ii-2) a progeny individual in which the DNA marker M5 is a homo-chromosome region of an allele derived from the original cultivar, and the DNA markers M3 and M4 are a hetero-chromosome region of an allele derived from the original cultivar and an allele derived from the foreign cultivar, from the progeny individual obtained in the step (3-7-1); a progeny individual obtained by backcrossing the progeny individual obtained in the step (3-7-1); or a progeny individual obtained by further backcrossing a progeny individual obtained by self-mating the progeny individual obtained in the step (3-7-1).

Among individuals selected in the step (3-7-2), (ii-1) the progeny individual in which the DNA marker M1 is a homo-chromosome region of an allele derived from the original cultivar, and the DNA markers M2 and M3 are a hetero-chromosome region of an allele derived from the original cultivar and an allele derived from the foreign cultivar corresponds to the progeny individual (1a) finally selected in the step (1-4) of the first method of creating a new cultivar of the present invention. On the other hand, from individuals selected in the step (3-7-2), (ii-2) the progeny individual in which the DNA marker M5 is a homo-chromosome region of an allele derived from the original cultivar, and the DNA markers M3 and M4 are a hetero-chromosome region of an allele derived from the original cultivar and an allele derived from the foreign cultivar corresponds to the progeny individual (2a) finally selected in the step (2-4) of the second method of creating a new cultivar of the present invention. Therefore, the individual selected on the step (3-7-2) is a progeny individual in which an end on an upstream side of a foreign cultivar-derived chromosome fragment L is between the DNA markers M1 and M2, and an end on a downstream side thereof is between the DNA markers M4 and M5, by performing the step (3-5') and (3-6'), like the steps (1-5) and (1-6) of the first method of creating a new cultivar of the present invention, or the steps (2-5) and (2-6) of the second method of creating a new cultivar of the present invention. That is, by selection in the step (3-7-2), an objective new cultivar created by the third method of creating a new cultivar of the present invention can be obtained.

FIG. 6A to FIG. 9G are views showing a chromosome region of a relatively preferable progeny individual among progeny individuals obtained in the step (3-7-1). In the figures, a non-filled bold line shows an allele derived from the original cultivar, and a filled bold line shows an allele derived from the foreign cultivar. A progeny individual (3a-a) in which the DNA marker M1 is a homo-chromosome region of an allele derived from the original cultivar, and the DNA markers M2 to M5 is a hetero-chromosome region; and a progeny individual (3a-b) in which the DNA markers M1 and M2 are a homo-chromosome region of an allele derived from the original cultivar, and the DNA markers M3 to M5 are a hetero-chromosome region; are a progeny individual obtained by self-mating of the progeny individual (3a) (see FIG. 6A and FIG. 6B).

Figure 6A:
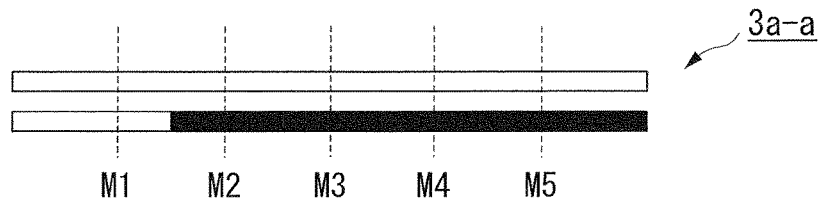
FIG. 6A is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 6B:
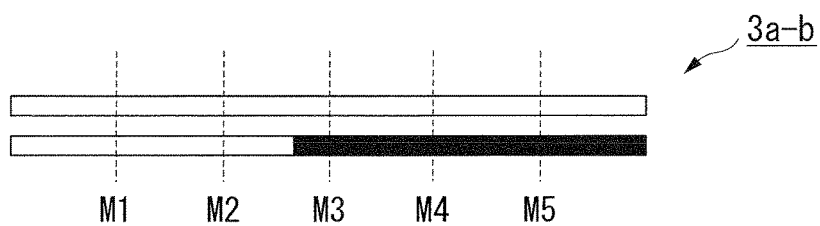
FIG. 6B is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 6C:
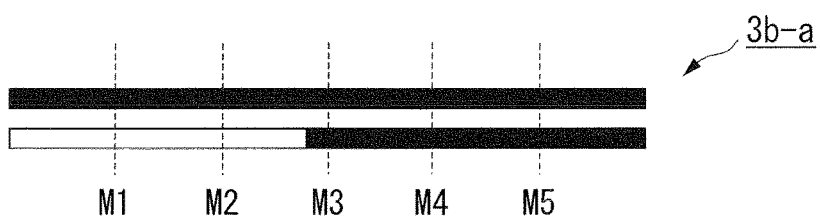
FIG. 6C is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 6D:
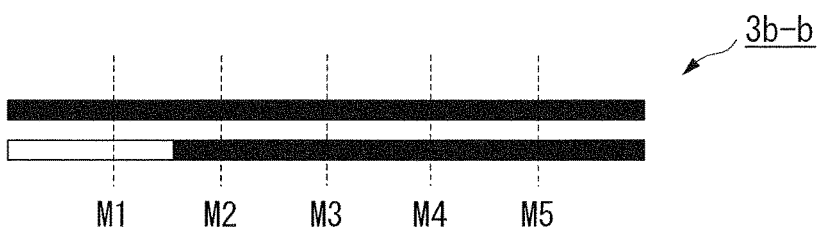
FIG. 6D is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7A:
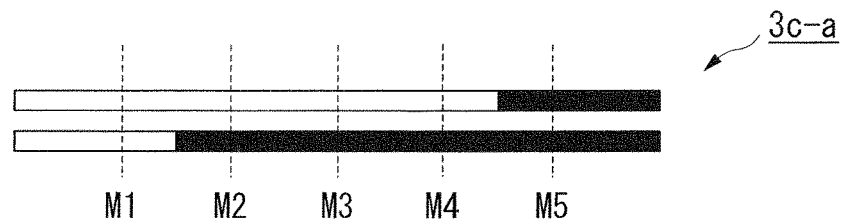
FIG. 7A is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7B:
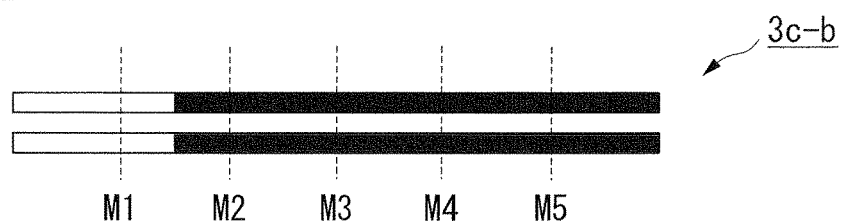
FIG. 7B is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7C:
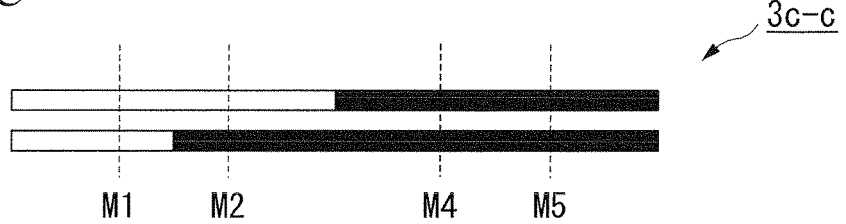
FIG. 7C is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7D:
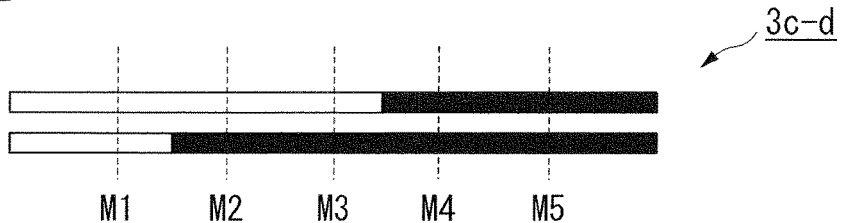
FIG. 7D is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7E:
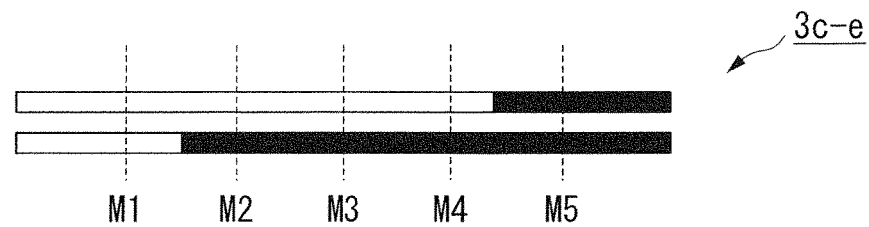
FIG. 7E is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7F:
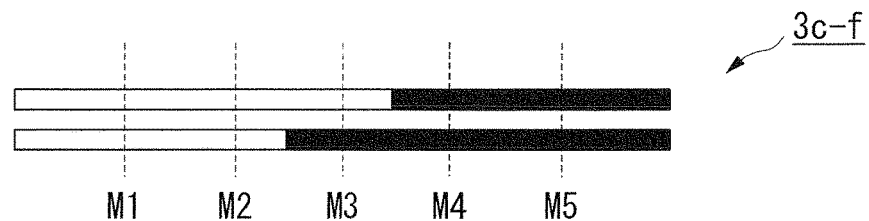
FIG. 7F is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 7G:
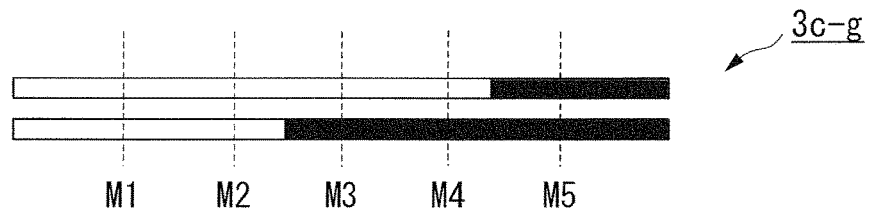
FIG. 7G is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.

A progeny individual (3b-a) in which the DNA markers M1 and M2 are a hetero-chromosome region, and the DNA markers M3 to M5 are a homo-chromosome region of an allele derived from the foreign cultivar; and a progeny individual (3b-b) in which the DNA marker M1 is a hetero-chromosome region, and the DNA markers M2 to M5 are a homo-chromosome region of an allele derived from the foreign cultivar; are a progeny individual obtained by self-mating of the progeny individual (3b) (see FIG. 6C and FIG. 6D).

A progeny individual (3c-a) in which the DNA marker M1 is a homo-chromosome region of an allele derived from the original cultivar, the DNA markers M2 to M4 are a hetero-chromosome region, and the DNA marker M5 is a homo-chromosome region of an allele derived from the foreign cultivar; a progeny individual (3c-b) in which the DNA marker M1 is a homo-chromosome region of an allele derived from the original cultivar, and the DNA markers M2 to M5 are a homo-chromosome region of an allele derived from the foreign cultivar; a progeny individual (3c-c) in which the DNA marker M1 is a homo-chromosome region of an allele derived from the original cultivar, the DNA marker M2 is a hetero-chromosome region, and the DNA markers M4 and M5 are a homo-chromosome region of an allele derived from the foreign cultivar; a progeny individual (3c-d) in which the DNA marker M1 is a homo-chromosome region of an allele derived from the original cultivar, the DNA markers M2 and M3 are a hetero-chromosome region, and the DMA makers M4 and M5 are a homo-chromosome region of an allele derived from the foreign cultivar; a progeny individual (3c-e) in which the DNA marker M1 is a homo-chromosome region of an allele derived from the original cultivar, the DNA markers M2 to M4 are a hetero-chromosome region, and the DNA marker M5 is a homo-chromosome region of an allele derived from the foreign cultivar; a progeny individual (3c-f) in which the DNA markers M1 and M2 are a homo-chromosome region of an allele derived from the original cultivar, the DNA marker M3 is a hetero-chromosome region, and the DNA markers M4 and M5 are a homo-chromosome region of an allele derived from the foreign cultivar; and a progeny individual (3c-g) in which the DNA markers M1 and M2 are a homo-chromosome region of an allele derived from the original cultivar, the DNA markers M3 and M4 are a hetero-chromosome region, and the DNA marker M5 is a homo-chromosome region of an allele derived from the foreign cultivar; are a progeny individual obtained by self-mating of the progeny individual (3c) (see FIG. 7A to FIG. 7G).

Figure 8A:
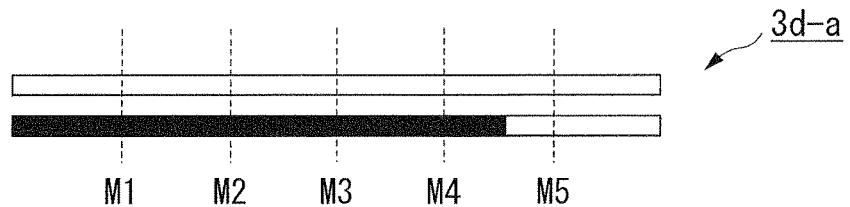
FIG. 8A is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 8B:
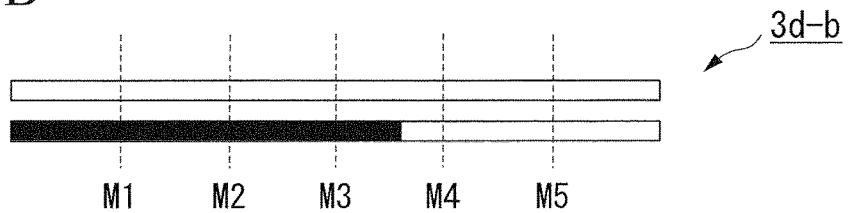
FIG. 8B is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.

In addition, a progeny individual (3d-a) in which the DNA markers M1 to M4 are a hetero-chromosome region, and the DNA marker M5 is a homo-chromosome region of an allele derived from the original cultivar; and a progeny individual (3d-b) in which the DNA markers M1 to M3 are a hetero-chromosome region, and the DNA markers M4 and M5 are a homo-chromosome region of an allele derived from the original cultivar; are a progeny individual obtained by self-mating of the progeny individual (3d) (see FIG. 8A and FIG. 8B).

Figure 8C:
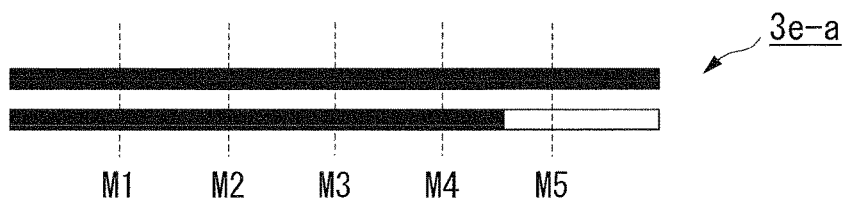
FIG. 8C is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 8D:
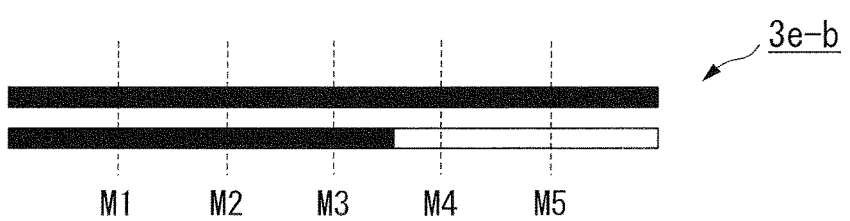
FIG. 8D is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9A:
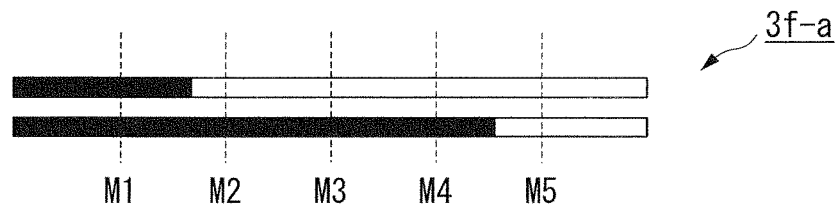
FIG. 9A is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9B:
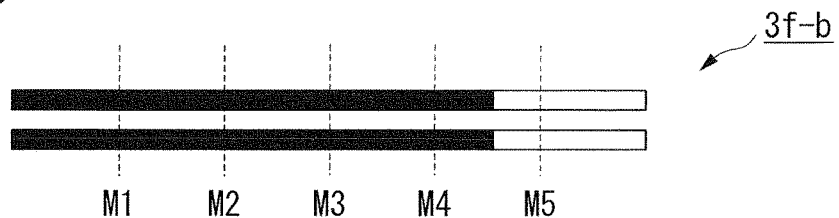
FIG. 9B is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9C:
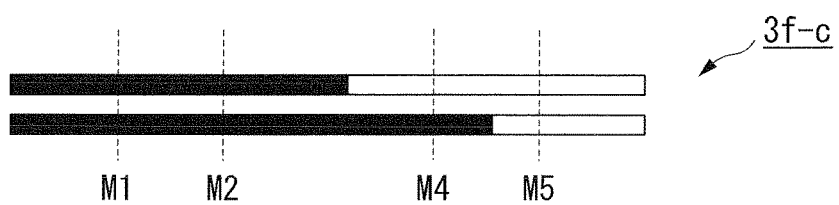
FIG. 9C is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9D:
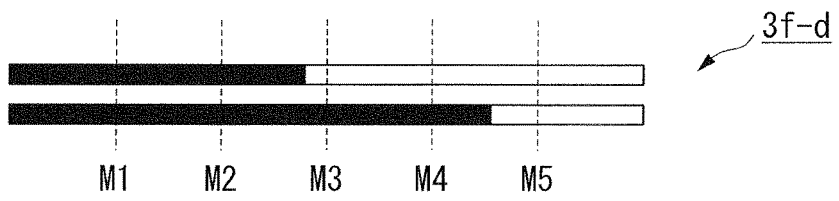
FIG. 9D is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9E:
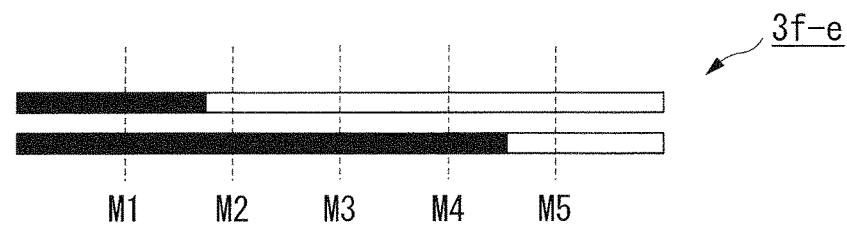
FIG. 9E is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9F:
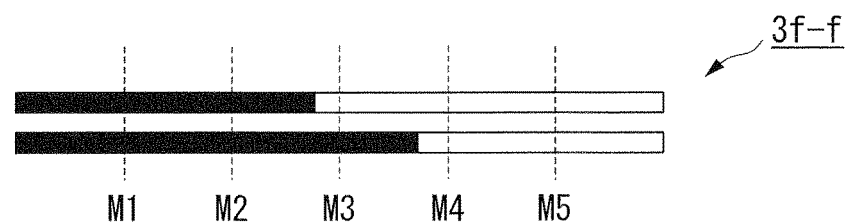
FIG. 9F is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.
Figure 9G:
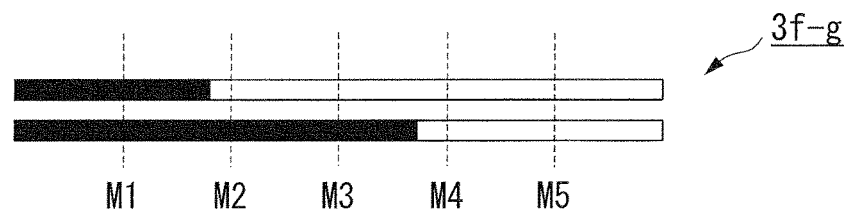
FIG. 9G is a view showing a chromosome region of a progeny individual relatively preferable in a step (3-7-2), among progeny individuals obtained in a step (3-7-1). In the figure, a non-filled bold line shows an allele derived from an original cultivar, and a filled bold line shows an allele derived from a foreign cultivar, respectively.

A progeny individual (3e-a) in which the DNA markers M1 to M4 are a homo-chromosome region of an allele derived from the foreign cultivar, and the DNA marker M5 is a hetero-chromosome region; and a progeny individual (3e-b) in which the DNA markers M1 to M3 are a homo-chromosome region of an allele derived from the foreign cultivar, and the DNA markers M4 and M5 are a hetero-chromosome region; are a progeny individual obtained by self-mating of the progeny individual (3e) (see FIG. 8C and FIG. 8D).

A progeny individual (3f-a) in which the DNA marker M1 is a homo-chromosome region of an allele derived from the original cultivar, the DNA markers M2 to M4 are a hetero-chromosome region, and the DNA marker M5 is a homo-chromosome region of an allele derived from the foreign cultivar; a progeny individual (3f-b) in which the DNA markers M1 to M4 are a homo-chromosome region of an allele derived from the foreign cultivar, and the DNA marker M5 is a homo-chromosome region of an allele derived from the original cultivar; a progeny individual (3f-c) in which the DNA markers M1 and M2 are a homo-chromosome region of an allele derived from the foreign cultivar, the DNA marker M4 is a hetero-chromosome region, and the DNA marker M5 is a homo-chromosome region of an allele derived from the original cultivar; a progeny individual (3f-d) in which the DNA markers M1 and M2 are a homo-chromosome region of an allele derived from the foreign cultivar, the DNA markers M3 and M4 are a hetero-chromosome region, and the DNA marker M5 is a homo-chromosome region of an allele derived from the original cultivar; a progeny individual (3f-e) in which the DNA marker M1 is a homo-chromosome region of an allele derived from the foreign cultivar, the DNA markers M2 to M4 are a hetero-chromosome region, and the DNA marker M5 is a homo-chromosome region of an allele derived from the original cultivar; a progeny individual (3f-f) in which the DNA markers M1 and M2 are a homo-chromosome region of an allele derived from the foreign cultivar, the DNA marker M3 is a hetero-chromosome region, and the DNA markers M4 and M5 are a homo-chromosome region of an allele derived from the original cultivar; and a progeny individual (3f-g) in which the DNA marker M1 is a homo-chromosome region of an allele derived from the foreign cultivar, the DNA markers M2 and M3 are a hetero-chromosome region, and the DNA markers M4 and M5 are a homo-chromosome region of an allele derived from the original cultivar; are a progeny individual obtained by self-mating of the progeny individual (3f) (see FIG. 9A to FIG. 9G).

Among these progeny individuals obtained in the step (3-7-1), the progeny individual (3a-a) corresponds to the progeny individual (1a) shown in FIG. 2A, and the progeny individual (3d-a) corresponds to the progeny individual (2a) shown in FIG. 3A. Therefore, these progeny individuals can be selected to proceed to the next step (3-5').

In addition, when the progeny individuals (3b-b), (3c-a), (3c-b), (3c-c), (3c-d), and (3c-e) are self-mated, respectively, an individual in which a chromosome region corresponds to that of the progeny individual (1a) can be included in progeny individuals obtained by this self-mating. Similarly, when the progeny individuals (3e-a), (3f-a), (3f-b), (3f-c), (3f-d), and (3f-e) are self-mated, respectively, an individual in which a chromosome region corresponds to that of the progeny individual (2a) is included in progeny individual obtained by this self-mating. Then, these progeny individuals can be selected to proceed to a next step (3-5').

On the other hand, when the progeny individual (3b-a) is self-mated, among progeny individuals obtained by this self-mating, an individual in which a chromosome region corresponds to that of the progeny individual (3b-b) can be contained. Similarly, when the progeny individual (3e-b) is self-mated, among progeny individuals obtained by this self-mating, an individual in which a chromosome region corresponds to that of the progeny individual (3e-a) can be contained. Then, these progeny individuals corresponding to the progeny individual (3b-b) or (3e-a) are selected from the self-mated groups, and further self-mated. And then, among progeny individuals obtained by this self-mating, an individual in which a chromosome region corresponds to that of the progeny individual (1a) or the progeny individual (2a) can be selected to proceed to the next step (3-5').

In progeny individuals selected in the step (3-4), a progeny individual in which a position of a recombination point about a region of an allele derived from the original species and a region of an allele derived from the foreign cultivar is unknown, and a target region is not substituted with a chromosome fragment derived from the foreign cultivar; and a progeny individual in which a target region is merely partially substituted with a chromosome fragment derived from the foreign cultivar; are also contained. Then, from progeny individuals selected in the step (3-4), a progeny individual in which the target region is substituted with a chromosome fragment derived from the foreign cultivar is selected, and this selected progeny individual may be used in the step (3-5).

Herein, selection of a progeny individual in which the target region is substituted with a chromosome fragment derived from the foreign cultivar may be a selection using a DNA marker, or may be a selection by the character detection. In the case of selection by using the DNA marker, a progeny individual in which a DNA marker M3 is a heterochromosome region of an allele derive from the original cultivar and an allele derived from the foreign cultivar is selected. In the case of selection by the character detection, a progeny individual having a target character introduced by substitution with a foreign cultivar-derived chromosome fragment is selected. When the number of the progeny individuals obtained in the step (3-3) is small, selection by the character detection may be performed.

It is preferable to confirm whether progeny individuals selected in the step (1-6), (2-6) or (3-6), that is, new cultivars created by the first to third methods of creating a new cultivar of the present invention have an objective character or not. For example, autogamous seeds are collected from individuals of a new cultivar, and the seeds are individually cultivated as a population. By appropriately observing or analyzing the cultivated populations, possession of an objective character and no segregation of the population as a whole are confirmed.

In addition, in the first to third methods of creating a new cultivar of the present invention, the number of the target regions may be one or plural. In the case of plural target regions, a progeny individual in which all target regions are substituted with a homo-chromosome fragment derived from the foreign cultivar can be obtained by repeatedly performing the above steps for every target region.

According to the first to third methods of creating a new cultivar of the present invention, a region of a chromosome fragment derived from the foreign cultivar to be introduced into a chromosome of the original cultivar can be controlled, and other genes other than an objective gene region can be effectively suppressed from being introduced into a chromosome of the original cultivar. Therefore, a new cultivar having a target character can be made without changing a preferable character possessed by the original cultivar. For this reason, in cultivars created by the first to third methods of creating a new cultivar of the present invention, the effect of improving a character of the original cultivar by a chromosome fragment introduced into the chromosome can be determined with very high reliance.

According to the first to third methods of creating a new cultivar of the present invention, via a specified step such as the steps (1-1) to (1-6), a cultivar in which a region encoding an objective gene is a target region, and only such a short region that other genes other than this objective gene are not contained, is substituted with a chromosome fragment derived from the foreign cultivar can be created.

For example, in a rice genome, theoretically, unless the region of chromosome is 12 Mbp or more as an average, crossing of the chromosomes occur simultaneously at 2 points, and a recombinant in which this region is recombined cannot be obtained theoretically, due to a chiasma interference. Therefore, an existing probability of a progeny individual in which only a short specified region is substituted is very small. For this reason, when a DNA marker is merely set for a desired region and the selection is performed by the previous MAS method using this DNA marker as an index, it is necessary that a selected population is large scale. For this reason, the labor and the cost required for the selection become excessive. Further, since an amount of a seed which can be harvested from one rice is limited, there is a high possibility that the desired progeny individual cannot be obtained even when screening is repeated many times.

To the contrary, the first to third methods of creating a new cultivar of the present invention allow for creation of a progeny individual in which only a chromosome fragment region is substituted just as designed as keeping a selection population being a general size.

In addition, in the first to third methods of creating a new cultivar of the present invention, respective DNA markers M1 to M5 defined for the target region are genome information peculiar to cultivars created by these methods. Therefore, the cultivars created by first to third methods of creating a new cultivar of the present invention can be discriminated using these DNA markers.

Specifically, a method of discriminating a plant cultivar of the present invention is a method of discriminating whether a plant individual is a specified cultivar produced using the first to third methods of creating a new cultivar of the present invention, wherein one or more DNA markers selected from the group consisting of DNA markers M1 to M5 are typed by genome analysis of this plant individual and, when the typing result is consistent with the result of the specified cultivar, it is determined that this plant individual is the specified cultivar.

Herein, five of DNA markers M1 to M5 are designed for every one target region, but all of these DNA markers M1 to M5 may be used, and some of these DNA markers may be used, for discriminating a cultivar. For example, only DNA markers M1 and M2 which are a recombination point on an upstream side of the target region may be used, only the DNA markers M4 and M5 which are a recombination point on a downstream side of a target region may be used, or only DNA markers M2 and M4 containing the target region therebetween may be used. Alternatively, when the number of target regions is plural, DNA markers of respective target regions may be appropriately used by combination. By appropriately combining plural DNA markers, it becomes possible to discriminate cultivar more strictly.

Individuals of cultivars created by the first to third methods of creating a new cultivar of the present invention (hereinafter, referred to as present first cultivar in some cases) can be mated to obtain a progeny individual like an individual of the original cultivar used in creation of this individual. Particularly, it is preferable to obtain a progeny individual by mating two individuals selected from the group consisting of an individual of the present first cultivar and a progeny individual of this first cultivar. In the present invention, it is preferable that these two individuals are such that at least one target region is different from each other. In addition, it is preferable that a progeny individual obtained by mating is such that plural target regions in a chromosome of the original cultivar are substituted with a homo-chromosome fragment derived from the foreign cultivar.

Then, a fourth method of creating a new cultivar of the present invention will be explained. In the fourth method of creating a new cultivar of the present invention, among individuals of the present first cultivars created by the first to third methods of creating a new cultivar of the present invention, two individuals in which at least one target region is different from each other are mated as a parent individual. Thereby, a new cultivar having a genome in which regions substituted with a chromosome fragment derived from the foreign cultivar possessed by each parent individual are accumulated, can be created.

That is, the fourth method of creating a new cultivar of the present invention has steps: (4-1) a step of using an individual of the present first cultivar as a seed parent, and an individual of the present first cultivar in which at least one target region is different from this seed parent as a pollen parent, and mating the seed parent and the pollen parent to obtain a progeny individual; (4-2) a step of self-mating the progeny individual obtained in the step (4-1) to obtain a progeny individual; (4-3) a step of selecting a progeny individual in which, in a chromosome of the original cultivar, all of target regions possessed by the seed parent and target regions possessed by the pollen parent are substituted with a homo-chromosome derived from the foreign cultivar, from the progeny individual obtained in the step (4-2).

In addition, the fourth method of creating a new cultivar of present invention may have further steps after the step (4-3): (4-4) a step of selecting two individuals in which at least one target region is different from each other, as a seed parent and a pollen parent, from the group consisting of an individual of the present first cultivar and an individual selected in the step (4-3), and mating them to obtain a progeny individual; (4-5) a step of self-mating the progeny individual obtained by the step (4-4) to obtain a progeny individual; (4-6) a step of selecting a progeny individual in which, in a chromosome of the original cultivar, all of a target region possessed by the seed parent and a target region possessed by the pollen parent are substituted with a homo-chromosome fragment derived from the foreign cultivar, from the progeny individuals obtained by the step (4-5); (4-7) a step of repeating the steps (4-4) to (4-6) once or more.

In addition, in each progeny individual obtained by the fourth method of creating a new cultivar of the present invention, whether each target region is a homozygote fragment derived from the foreign cultivar can be discriminated using DNA markers M1 to M5 used in the method of creating the first cultivar of the present invention.

In the previous cultivar improving method by backcrossing and the MAS method, a length of a chromosome fragment to be introduced in a chromosome of the original cultivar cannot be controlled, as described above. For this reason, many genes having the unknown function in addition to an objective gene are introduced together into a chromosome of the original cultivar. As the number of introduced chromosome fragment is increased, the number of introduced genes having unknown function is increased. Therefore, when one try to improve a plurality of characters by mating, a problem such as deterioration in character other than an objective character to be improved arises. In addition, like this, since there is a high possibility that many unknown genes are introduced, an objective character is not necessarily improved with an intentionally introduced chromosome fragment (chromosome fragment containing target region). For this reason, even in the case of a progeny individual having a chromosome fragment of a target region, many individuals having unimproved objective characters are obtained. Further, DNA markers used in selection are merely linked with a chromosome fragment of the target region in the original cultivar. For this reason, the chromosomes are randomly arranged by plural times mating of plant individuals and, as a result, DNA markers become not to link with a chromosome fragment of the target region. Therefore, when this DNA marker is used, a progeny individual having a chromosome fragment of the target region cannot be selected in many cases.

For example, by the previous mating method, an individual P1 (A) in which a homo-chromosome fragment of a target region A derived from the foreign cultivar is introduced into a chromosome of the original cultivar, and an individual P1 (B) in which a homo-chromosome fragment of a target region B derived from the foreign cultivar is introduced into a chromosome of the original cultivar are mated, and the resulting progeny individual is self-mated. Thereby, an individual P2 (AB) in which both of target regions A and B derived from the foreign cultivar are a homozygote, in a chromosome of the original cultivar, is obtained. Thereupon, when the target regions A and B are independent from each other, and are subject to a Mendel's law, the individual P2 (AB) can be selected from a progeny individual obtained by self-mating theoretically at a probability of 1/16. However, the selected individual P2 (AB) is not necessarily improved in objective two characters and, although objective characters are improved, other characters are deteriorated in many cases. This problem is more serious as the number of introduction target regions becomes larger and, actually, it was very difficult to improve three or more characters.

To the contrary, in individuals of cultivars created by the first to third methods of creating a new cultivar of the present invention, and progeny individuals of them, introduction of a chromosome region into a region other than the target region can be suppressed as much as possible. For this reason, there is a very high possibility that a character different from that of the original cultivar is the effect of the introduced chromosome fragment of the target region derive from the foreign cultivar. Therefore, like the fourth method of creating a new cultivar of the present invention, for example, when an individual P1 (A) in which a homo-chromosome fragment of a target region A derived from the foreign cultivar is introduced into a chromosome of the original cultivar by the first to third methods of creating a new cultivar of the present invention; and an individual P1 (B) in which a homo-chromosome fragment of a target region B derived from the foreign cultivar is similarly introduced; are mated, to thereby an individual P2 (AB) in which both of the target regions A and B derived from the foreign cultivar are a homozygote is obtained. In this individual P2 (AB), it can be sufficiently expected that both characters of the improved character A possessed by the individual P1 (A) and the improved character B possessed by the individual P1 (B) are improved without changing a preferable character possessed by other original cultivars. Like this, by using the fourth method of creating a new cultivar of the present invention, improved characters can be sequentially accumulated by mating, and three or more characters can be improved simply and at a high procession.

In addition, DNA markers M1 to M5 used in selection are DNA markers in a target region or in vicinity of the target region. For this reason, even when mating is repeated plural times like the case using the fourth method of creating a new cultivar of the present invention, a progeny individual having a chromosome fragment of the target region can be sufficiently selected using these DNA markers M1 to M5.

For example, an individual P1 (A) which is an individual of the present first cultivar and in which a homo-chromosome fragment of a target region A derived from the foreign cultivar is introduced into a chromosome of the original cultivar is used as a seed parent, and an individual P1 (B) which is an individual of the present first cultivar and in which a homo-chromosome fragment of a target region B derived from the foreign cultivar is introduced into a chromosome of the original cultivar is used as a pollen parent. And, P1 (A) and P1 (B) are mated, the resulting progeny individual is self-mated to obtain a progeny individual. And then, from the progeny individual obtained by this self-mating, an individual P2 (AB) in which, in a chromosome of the original cultivar, all of the target regions A and B are substituted with a homo-chromosome fragment derived from the foreign cultivar is selected. Thereby, a new cultivar can be created. Herein, when the target regions A and B are independent of each other without linkage, and are subject to a Mendel's law, the individual P2 (AB) can be selected from a progeny individual obtained by self-mating at a probability of 1/16.

In addition, the thus obtained progeny individual P2 (AB), and an individual P1 (C) in which a homo-chromosome fragment of a target region C derived from the foreign cultivar is introduced into a chromosome of the original cultivar are mated to obtain a progeny individual. Thereafter, this obtained progeny individual is self-mated and, from the progeny individual obtained by this self-mating, an individual P3 (ABC) in which, in a chromosome of the original cultivar, all of target regions A, B and C are substituted with a homo-chromosome fragment derived from the foreign cultivar is selected. Thereby, a new cultivar can be created. Herein, when the target regions A, B and C are independent of each other without linkage, and are subject to a Mendel's law, the individual P3 (ABC) can be selected from a progeny individual obtained by self-mating at a probability of 1/64.

The individual P3 (ABC) in which all of the target regions A, B and C are substituted with a homo-chromosome fragment derived from the foreign cultivar can be also created, for example, by the following method. First, P1 (B) and P1 (C) are mated to obtain a progeny individual, and the resulting progeny individual is self-mated. From a progeny individual obtained by this self-mating, an individual P2 (BC) in which, in a chromosome of the original cultivar, target regions B and C are substituted with a homo-chromosome fragment derived from the foreign cultivar is selected. Herein, when the target regions B and C are independent of each other without linkage, and are subject to a Mendel's law, the individual P2 (BC) can be selected from progeny individuals obtained by self-mating at a probability of 1/16. Thereafter, P2 (AB) and P2 (BC) are mated to obtain a progeny individual, and then this progeny individual is self-mated. From the resulting progeny individual, P3 (ABC) is selected, thereby, P3 (ABC) can be created. In both of P2 (AB) and P2 (BC), the target region B is a homozygote derived from the foreign cultivar. Therefore, when the target regions A, B and C are independent respectively without linkage, and are subject to a Mendel's law, the individual P3 (ABC) can be selected from the progeny individual obtained by self-mating at a probability of 1/16.

Figure 10A:
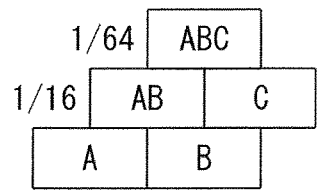
FIG. 10A is a schematic view showing a method of creating a cultivar in which three target regions (target regions A, B, C) in a chromosome of an original cultivar are substituted with a chromosome fragment derived from a foreign cultivar.
Figure 10B:
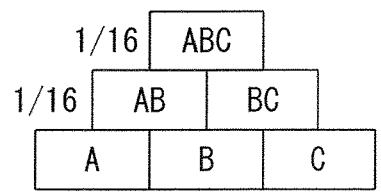
FIG. 10B is a schematic view showing a method of creating a cultivar in which three target regions (target regions A, B, C) in a chromosome of an original cultivar are substituted with a chromosome fragment derived from a foreign cultivar.

FIG. 10A and FIG. 10B are a schematic view showing a method of creating a cultivar in which, in a chromosome of the original cultivar, three target regions (target regions A, B, C) are substituted with a chromosome fragment derived from the foreign cultivar. In the figures, a square indicates each individual, and an alphabet in the square indicates that each target region is substituted with a homo-chromosome fragment derived from the foreign cultivar. In a pyramid in which squares are piled, one square is piled on an upper step of two squares. This means that two squares on a lower step are a parent individual, and one square on an upper step is a progeny individual obtained by mating. In addition, a numerical value on a left side of the pyramid in which squares are piled indicates a probability of obtaining of each progeny individual when respective target regions are independent respectively without linkage, and are subject to a Mendel's law.

FIG. 10A shows a method of creating P3 (ABC) by mating the aforementioned P2 (AB) and P1 (C). FIG. 10B shows a method of creating P3 (ABC) by mating the aforementioned P2 (AB) and P2 (BC). Like this, by sequentially mating individuals in which at least one target region is different from each other among cultivars created by using the first to third methods of creating a new cultivar of the present invention and progeny individuals thereof, plural kinds of target regions substituted with a chromosome fragment derived from the foreign cultivar are being accumulated in a progeny individual. For this reason, a cultivar in which, in a chromosome of the original cultivar, four or more target regions are substituted with a chromosome fragment derived from the foreign cultivar can be also created.

Herein, the case of production of a cultivar P4 (ABCD) in which, in a chromosome of the original cultivar, four target regions (target regions A, B, C, D) are substituted with a chromosome fragment derived from the foreign cultivar will be described. First, for example, an individual P2 (AB) in which target regions A and B are substituted with a homo-chromosome fragment derived from the foreign cultivar, and an individual P2 (CD) in which target regions C and D are substituted with a homo-chromosome fragment derived from the foreign cultivar are mated to obtain a progeny individual. Then, by selecting P4 (ABCD) from progeny individuals obtained by self-mating this progeny individual, P4 (ABCD) can be created. Thereupon, when target regions A, B, C and D are independent respectively without linkage, and are subject to a Mendel's law, an individual P4 (ABCD) can be selected from a progeny individual obtained by the self-mating, at a probability of 1/256. Similarly, in the case of creation of a cultivar P5 (ABCDE) in which five target regions (target regions A, B, C, D, E) are substituted with a chromosome fragment derived from the foreign cultivar, first, for example, an individual P3 (ABC) in which target regions A, B, C are substituted with a homo-chromosome fragment derived from the foreign cultivar, and an individual P2 (BD) in which target regions B and E are substituted with a homo-chromosome fragment derived from the foreign cultivar are mated to obtain a progeny individual and this progeny individual is self-mated. Then, by selecting P5 (ABCDE) from progeny individuals obtained by this self-mating, P5 (ABCDE) can be created. Thereupon, when target regions A, B, C, D and E are independent respectively without linkage, and are subject a Mendel's law, the individual P5 (ABCDE) can be selected from a progeny individual obtained by self-mating, at a probability of 1/1024.

However, usually, when an objective progeny individual is obtained, a size of a selected population (group of progeny individuals obtained by self-mating) is set to be around a few to 10-fold an existing probability of an objective progeny individual. When a size of the selected population is insufficient, there is a high possibility that an objective progeny individual is not obtained. On the other hand, usually, the number of seeds which can be collected from one individual is limited. For example, in rice, only around 1,000 seeds can be ensured from one individual. In addition, a rice plant is weak, and sometimes only a few tens of seeds are obtained from one plant. Further, as a size of the selected population grows larger, the necessary time, labor and cost become excessive. For this reason, it is thought that a production method in which an existing probability of an objective progeny individual is 1/1024 or more is actually very difficult to be implemented.

In the fourth method of creating a new cultivar of the present invention, by sequentially mating the selected progeny individual, a target region substituted with a chromosome fragment derived from the foreign cultivar can be accumulated in that progeny individual. Therefore, a new cultivar can be created so that an existing probability of an objective progeny individual in a once selected population becomes 1/256 to 1/16.

Figure 11A:
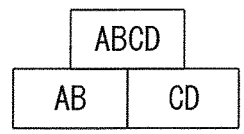
FIG. 11A is a schematic view showing a method of creating a cultivar in which four target regions (target regions A, B, C, D) in a chromosome of an original cultivar are substituted with a chromosome fragment derived from a foreign cultivar.
Figure 11B:
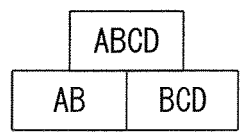
FIG. 11B is a schematic view showing a method of creating a cultivar in which four target regions (target regions A, B, C D) in a chromosome of an original cultivar are substituted with a chromosome fragment derived from a foreign cultivar.

For example, regarding the case where target regions A, B, C and D are independent respectively without linkage, and are subject to a Mendel's law, a method of creating P4 (ABCD) will be described (see FIG. 11A to FIG. 11C). First, P2 (AB) and P2 (CD) are crated according to the same manner as that of the aforementioned method of creating P2 (AB). Thereafter, P2 (AB) and P2 (CD) are mated to obtain a progeny individual, and this progeny individual is self-mated. Then, by selecting P4 (ABCD) from progeny individuals obtained by this self-mating, P4 (ABCD) can be created (see FIG. 11A). In this case, theoretically, P4 (ABCD) can be selected from a selected population at a probability of 1/256.

Alternatively, P2 (AB), and P3 (BCD) created according to the same manner as that of the aforementioned method of creating P3 (ABC) are mated to obtain a progeny individual, and this progeny individual is self-mated. From the progeny individual obtained by this self-mating, P4 (ABCD) may be selected (see FIG. 11B). Both of P2 (AB) and P3 (BCD) are such that the target region B is a homozygote derived from the foreign cultivar. For this reason, theoretically, P4 (ABCD) can be selected from a selected population at a probability of 1/64.

Figure 11C:
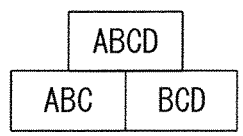
FIG. 11C is a schematic view showing a method of creating a cultivar in which four target regions (target regions A, B, C, D) in a chromosome of an original cultivar are substituted with a chromosome fragment derived from a foreign cultivar.
Figure 12A:
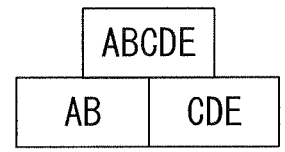
FIG. 12A is a schematic view showing a method of creating a cultivar in which five target regions (target regions A, B, C, D, E) in a chromosome of an original cultivar are substituted with a chromosome fragment derived from a foreign cultivar.
Figure 12B:
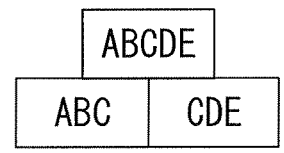
FIG. 12B is a schematic view showing a method of creating a cultivar in which five target regions (target regions A, B, C, D, E) in a chromosome of an original cultivar are substituted with a chromosome fragment derived from a foreign cultivar.
Figure 12C:
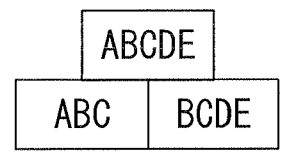
FIG. 12C is a schematic view showing a method of creating a cultivar in which five target regions (target regions A, B, C, D, E) in a chromosome of an original cultivar are substituted with a chromosome fragment derived from a foreign cultivar.
Figure 12D:
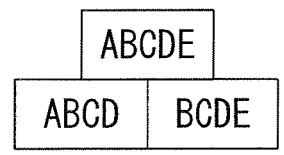
FIG. 12D is a schematic view showing a method of creating a cultivar in which five target regions (target regions A, B, C, D, E) in a chromosome of an original cultivar are substituted with a chromosome fragment derived from a foreign cultivar.
Figure 13A:
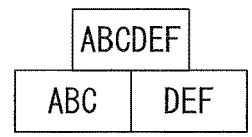
FIG. 13A is a schematic view showing a method of creating a cultivar in which six target regions (target regions A, B, C, D, E, F) in a chromosome of an original cultivar are substituted with a chromosome fragment derived from a foreign cultivar.
Figure 13B:
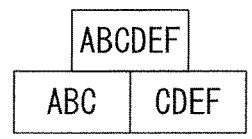
FIG. 13B is a schematic view showing a method of creating a cultivar in which six target regions (target regions A, B, C, D, E, F) in a chromosome of an original cultivar are substituted with a chromosome fragment derived from a foreign cultivar.
Figure 13C:
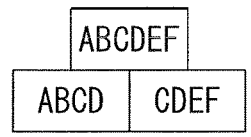
FIG. 13C is a schematic view showing a method of creating a cultivar in which six target regions (target regions A, B, C, D, E, F) in a chromosome of an original cultivar are substituted with a chromosome fragment derived from a foreign cultivar.
Figure 13D:
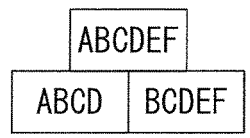
FIG. 13D is a schematic view showing a method of creating a cultivar in which six target regions (target regions A, B, C, D, E, F) of a chromosome in an original cultivar are substituted with a chromosome fragment derived from a foreign cultivar.
Figure 13E:
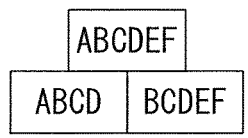
FIG. 13E is a schematic view showing a method of creating a cultivar in which six target regions (target regions A, B, C, D, E, F) in a chromosome of an original cultivar are substituted with a chromosome fragment derived from a foreign cultivar.

Further, after P3 (ABC) and P3 (BCD) created according to the same manner as that of P3 (BCD) are mated to obtain a progeny individual, P4 (ABCD) may be selected from progeny individuals obtained by self-mating this progeny individual (see FIG. 11C). Both of P3 (ABC) and P3 (BCD) are such that target regions B and C are a homozygote derived from the foreign cultivar. For this reason, theoretically, P4 (ABCD) can be selected from a selected population at a probability of 1/16.

That is, according to the method of creating a new cultivar of the present invention, even when the number of target regions is 4, an objective new cultivar can be selected at a higher probability than previous.

In addition, for example, regarding the case where target regions, A, B, C, D and E are independent respectively without linkage, and are subject to a Mendel's law, a method of creating P5 (ABCDE) will be described (see FIG. 12A to FIG. 12D). First, P2 (AB) and P3 (CDE) are mated to obtain a progeny individual and this progeny individual is self-mated. Thereafter, by selecting P5 (ABCDE) from progeny individuals obtained by this self-mating, P5 (ABCDE) can be created (see FIG. 12A). In this case, theoretically, P5 (ABCDE) can be selected from a selected population at a probability of 1/1024.

To the contrary, in the following case, a probability of selection of P5 (ABCDE) is improved.

P3 (ABC) and P3 (CDE) are created according to the same manner as the aforementioned method of creating P3 (ABC), respectively. Thereafter, these P3 (ABC) and P3 (CDE) are mated to obtain a progeny individual and this progeny individual is self-mated. Further, by selecting P5 (ABODE) from progeny individuals obtained by this self-mating, P5 (ABODE) can be created (see FIG. 12B). Both of P3 (ABC) and P3 (ODE) are such that a target region C is a homozygote derived from the foreign cultivar. For this reason, in this case, theoretically, P5 (ABCDE) can be selected from a selected population at a probability of 1/256.

Alternatively, P3 (ABC) is created according to the same manner as the aforementioned method of creating P3 (ABC), and P4 (BODE) is created according to the same manner as the aforementioned method of creating P4 (ABCD). Thereafter, these P3 (ABC) and P4 (BODE) are mated to obtain a progeny individual and this progeny individual is self-mated. From progeny individuals obtained by this self-mating, P5 (ABODE) may be selected (see FIG. 120). Both of P3 (ABC) and P4 (BODE) are such that target regions B and C are a homozygote derived from the foreign cultivar. For this reason, theoretically, P5 (ABODE) can be selected from a selected population at a probability of 1/64.

Besides, according to the same manner as the aforementioned method of creating P4 (ABCD), P4 (ABCD) and P4 (BODE) are created, respectively. Thereafter, these P4 (ABCD) and P4 (BODE) are mated to obtain a progeny individual and this progeny individual is self-mated. Further, from progeny individuals obtained by this self-mating, P5 (ABCDE) may be selected (see FIG. 12D). Both of P4 (ABCD) and P4 (BCDE) are such that target regions B, C and D are a homozygote derived from the foreign cultivar. For this reason, in this case, theoretically, P5 (ABCDE) can be selected from a selected population at a probability of 1/16.

That is, according to the method of creating a new cultivar of the present invention, even when the number of target regions is 5, an objective new cultivar can be selected at a higher probability than previous.

In addition, for example, regarding the case where target regions A, B, C, D, E and F are independent respectively without linkage, and are subject to a Mendel's law, a method of creating P6 (ABCDEF) will be described (see FIG. 13A to FIG. 13E). For example, after P3 (ABC) and P3 (DEF) are mated to obtain a progeny individual, this progeny individual is self-mated. By selecting P6 (ABCDEF) from progeny individuals obtained by this self-mating, P6 (ABCDEF) can be created (see FIG. 13A). In this case, theoretically, a probability that P6 (ABCDEF) can be selected from a selected population is 1/4096.

Alternatively, after P3 (ABC) and P4 (CDEF) are mated to obtain a progeny individual, this progeny individual is self-mated to obtain progeny individuals. By selecting P6 (ABCDEF) from the progeny individuals obtained by the self-mating, P6 (ACBDEF) can be also created (see FIG. 13B). In this case, theoretically, a probability that P6 (ABCDEF) can be selected from a selected population is 1/1024.

To the contrary, in the following case, a probability of selection of P6 (ABCDEF) is improved.

First, P4 (ABCD) and P4 (CDEF) are created according to the same manner as the aforementioned method of creating P4 (ABCD), respectively. Then, these P4 (ABCD) and P4 (CDEF) are mated to obtain a progeny individual and this progeny individual is self-mated. Further, by selecting P6 (ABCDEF) from progeny individuals obtained by this self-mating, P6 (ABCDEF) can be created (see FIG. 13C). Thereupon, theoretically, P6 (ABCDEF) can be selected from a selected population at a probability of 1/256. This is because both of P4 (ABCD) and P4 (CDEF) are such that target regions C and D are a homozygote derived from the foreign cultivar.

Alternatively, P4 (ABCD) is created according to the same manner as the aforementioned method of creating P4 (ABCD), and P5 (BCDEF) is created according to the same manner as the aforementioned method of creating P5 (ABCDE). Thereafter, after these P4 (ABCD) and P5 (BCDEF) are mated to obtain a progeny individual, this progeny individual is self-mated. By selecting P6 (ABCDEF) from progeny individuals obtained by this self-mating, P6 (ABCDEF) can be also created (see FIG. 13D). Both of P4 (ABCD) and P5 (BCDEF) are such that target regions B, C and D are a homozygote derived from the foreign cultivar.

For this reason, in this case, theoretically, P5 (ABCDE) can be selected from a selected population at a probability of 1/64.

Alternatively, P5 (ABCDE) and P5 (BCDEF) are created according to the same manner as the aforementioned method of creating P5 (ABCDE), respectively. Thereafter, after P5 (ABCDE) and P5 (BCDEF) are mated to obtain a progeny individual, this progeny individual is self-mated. By selecting P6 (ABCDEF) from progeny individuals obtained by this self-mating, P6 (ABCDEF) can be also created (see FIG. 13E). Both of P5 (ABCDE) and P5 (BCDEF) are such that target regions B, C, D and E are a homozygote derived from the foreign cultivar. For this reason, in this case, theoretically, P6 (ABCDEF) can be selected from a selected population at a probability of 1/16.

That is, according to the method of creating a new cultivar of the present invention, even when the number of target regions is 6, an objective new cultivar can be selected at a higher probability than previous.

As described above, in the case of a plant in which the number of progeny individuals obtained by one time mating is relatively small, such as rice, it is preferable to create a new cultivar so that an existing probability of an objective progeny individual in a one time selected population becomes 1/64 to 1/16. That is, by sequentially mating individuals of a combination in which a sum of different target regions in a chromosome is 3 or less, it can be stably produced a cultivar in which plural target regions in a chromosome of the original cultivar are substituted with a chromosome fragment derived from the foreign cultivar.

Figure 14A:
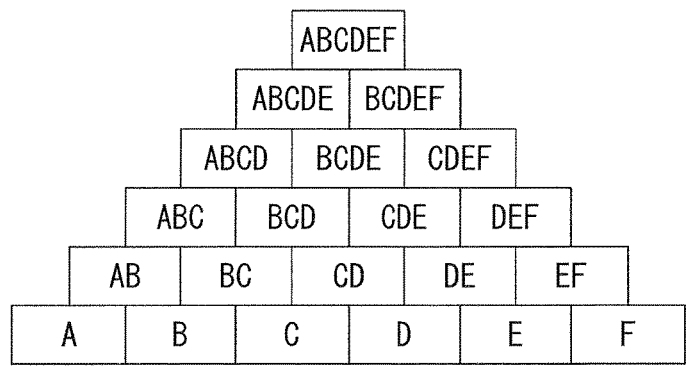
FIG. 14A is a schematic view showing a method of creating a cultivar P6 (ABCDEF), as an existing probability that an objective progeny individual is present in a one time selected population is 1/64 to 1/16.
Figure 14B:
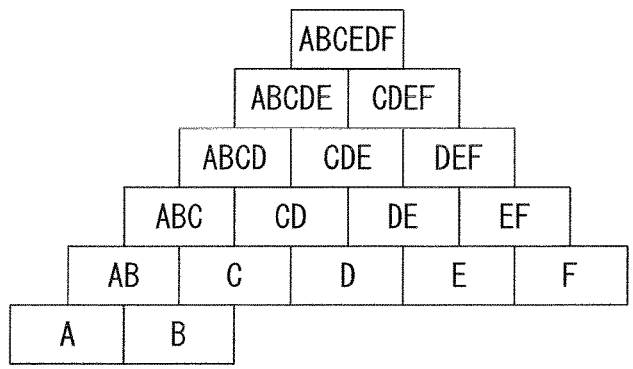
FIG. 14B is a schematic view showing a method of creating a cultivar P6 (ABCDEF), as an existing probability that an objective progeny individual is present in a one time selected population is 1/64 to 1/16.
Figure 14C:
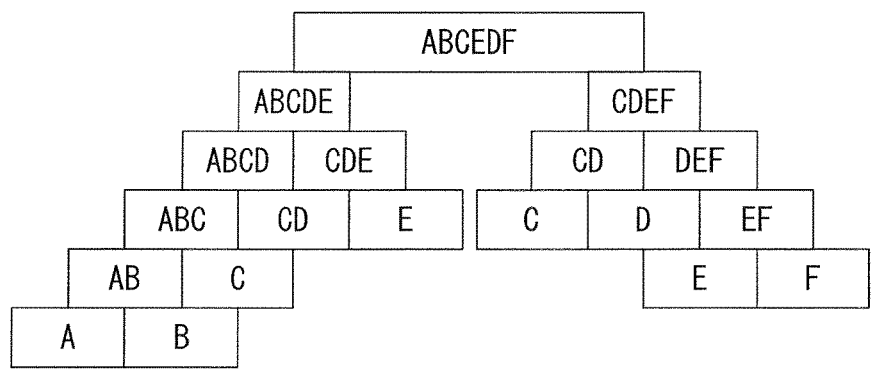
FIG. 14C is a schematic view showing a method of creating a cultivar P6 (ABCDEF), as an existing probability that an objective progeny individual is present in a one time selected population is 1/64 to 1/16.

FIG. 14A to FIG. 14C are schematic views showing a method of creating a cultivar P6 (ABCDEF) as an existing probability of an objective progeny individual in a one time selected population is 1/64 to 1/16. FIG. 14A is a view showing a method when the existing probability in all selected populations is 1/16. FIG. 14B and FIG. 14C are a view showing a method when the existing probability in all selected populations is 1/16 or 1/64. Even when the number of target regions is 7 or more, an individual can be created similarly as the existing probability of an objective progeny individual in a onetime selected population is 1/64 to 1/16.

When respective target regions are independent respectively without linkage, and are subject to a Mendel's law, how an existing probability of an objective progeny individual in an selected population can be appropriately determined in view of the number of progeny individuals obtained by one time mating, and a time until an individual of an objective cultivar is finally obtained. When the number of progeny individuals obtained by mating is sufficient, the existing probability of an objective progeny individual can be set to be low such as 1/64. In this case, a scale of a one time selected population becomes relatively large, and a time, the labor and the cost necessary for one time selection become large, but a cultivar in which the objective number of target regions are substituted with a chromosome fragment derived from the foreign cultivar can be obtained by relatively small selection times. On the other hand, when the number of progeny individuals obtained by one time mating is small, a scale of the one time selected population must be reduced. In this case, a time and the cost necessary for one time selection can be suppressed, but a selection time is increased, and a time until an individual of an objective cultivar is finally obtained is prolonged. For example, as shown in FIG. 11A to FIG. 11C, when P4 (ABCD) is created, in the method of FIG. 11A, first, P4 (ABCD) is created by three times selection: time of mating P1 (A) and P1 (B), and thereafter selecting P2 (AB); time of mating P1 (C) and P1 (D), and thereafter selecting P2 (CD); time of mating P2 (AB) and P2 (CD), and thereafter selecting P4 (ABCD). On the other hand, in the method of FIG. 11C, P4 (ABCD) is created, for example, by at least five times selection of: time of mating P1 (A) and P1 (B), and thereafter selecting P2 (AB); time of P1 (C) and P1 (D), and thereafter selecting P2 (CD); time of mating P2 (AB) and P1 (C), and thereafter selecting P3 (ABC); time of mating P1 (B) and P2 (CD), and thereafter selecting P3 (BCD); time of mating P3 (ABC) and P3 (BCD), and thereafter selecting P4 (ABCD). In the method of FIG. 11A, a target region substituted with a chromosome fragment derived from the foreign cultivar possessed by a parent individual to be mated is different in each parent individual. For this reason, it is necessary to make one time selected population larger than the method of FIG. 11C, but P4 (ABCD) can be created by a smaller selection time.

The new cultivar created by the present invention is, as described above, a progeny cultivar of a chromosome fragment-substituted line in which a part of a chromosome is substituted with a chromosome fragment derived from the foreign cultivar. In this new cultivar, one or plural target regions are substituted with a chromosome fragment derived from the foreign cultivar, and the length of a chromosome fragment is controlled by a DNA marker set upstream of the target region, and a DNA marker set downstream of a target region. In the present invention, by appropriately setting the target region, a useful new cultivar such as a new cultivar described in Examples described later, particularly, rice cultivar, *Oryza sativa* L. cultivar Koshihikari kazusa 4go can be obtained.

Besides, a new cultivar in which at least one region of plural regions substituted with a chromosome fragment derived from foreign cultivar possessed by a parent individual is substituted with a chromosome fragment derived from the original cultivar can be created. First, an individual of a cultivar created using the first to fourth methods of creating a new cultivar of the present invention, in which two or more target regions in a chromosome of the original cultivar are substituted with a chromosome fragment derived from the foreign cultivar, or a progeny individual of this individual, and an individual of the original cultivar are mated. Then, a progeny individual obtained by this mating is self-mated and, from a progeny individual obtained by this self-mating, an individual in which at least one region is substituted with a chromosome fragment derived from the original cultivar is selected.

For example, the case where an individual P3 (ABC) in which, in a chromosome of the original cultivar, all of target regions A, B and C are substituted with a homo-chromosome fragment derived from the original cultivar is created using the first to fourth methods of creating a new cultivar of the present invention will be described. First, this P3 (ABC) and an individual of the original cultivar are mated. Then, by self-mating a progeny individual obtained by this mating, an individual P2 (AB) in which only target regions A and B are substituted with a homo-chromosome fragment derived from the foreign cultivar and a target region C is substituted with a chromosome fragment derived from the original cultivar, or an individual P2 (B) in which only a target region B is substituted with a homo-chromosome fragment derived from the foreign cultivar and target regions A and C are substituted with a chromosome fragment derived from the original cultivar is selected. From the foregoing, an individual of a new cultivar in which at least one region of a plurality of regions substituted with a chromosome fragment derived from the foreign cultivar possessed by a parent individual is substituted with a chromosome fragment derived from the original cultivar can be obtained.

EXAMPLES

The following Examples further illustrate the present invention in more detail, but the present invention is not only limited to the following Examples.

Example 1

Using the present invention, a new cultivar having improved lodging resistance of rice cultivar Koshihikari was created.

First, a rice cultivar Habataki which is short, and a rice cultivar Koshihikari were mated, and QTL (Quantitative Trait Locus) analysis was performed on a segregated population. As a result, it was seen that great QTL is present in a Sd1 region of the first chromosome. It was presumed that when the region of Koshihikari is substituted with a gene region derived from Habataki, a height (rod length) of Koshihikari becomes small, and lodging resistance is strengthened. Then, Habataki was backcrossed with Koshihikari to create a chromosome fragment-substituted line in which the Sd1 region of Koshihikari is substituted with a gene fragment derived from Habataki.

Figure 15:
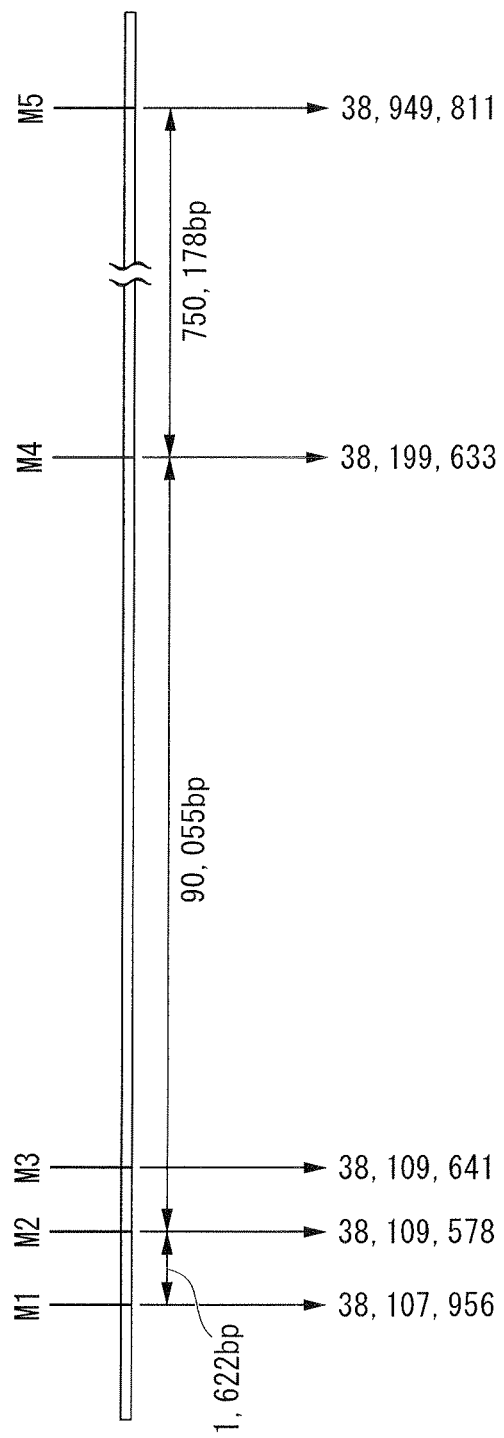
FIG. 15 is a view showing a DNA marker used in creating Koshihikari eichi 4go.

Then, according to the method of plant genome design of the present invention, a length of a chromosome fragment region derived from Habataki of the resulting chromosome-substituted line was regulated to design a genome. Specifically, a DNA marker SP-4009 in a Sd1 region was let to be a DNA marker M1 (Sd1), a DNA marker G2003 in a Sd1 region was let to be a DNA marker M2 (Sd1), a DNA marker G2002 in a Sd1 region was let to be a DNA marker M3 (Sd1), a DNA marker SP-462 in a Sd1 region was let to be a DNA marker M4 (Sd1), and a DNA marker SP-1259 in a Sd1 region was let to be a DNA marker M5 (Sd1). These DNA markers are shown in FIG. 15 and Table 1. A distance d1 between the DNA markers M1 (Sd1) and M2 (Sd1) is about 1.6 kbp, a distance d2 between the DNA markers M2 (Sd1) and M4 (Sd1) is about 90 kbp, and a distance d3 between the DNA makers M4 (Sd1) and M5 (Sd1) is about 750 kbp. Thereby, in a chromosome of Koshihikari, a length of a Habataki derived chromosome fragment $L_1$ is 90 kbp<$L_1$<842 kbp.

TABLE 1

| | Markere | Type | Position | Sequence (SEQ ID NOS 1-13, respectively, in order of appearance) |
|---|---|---|---|---|
| M1 (Sd1) | SP-4009 | SNP | 38,107,956 | Upper Sequence: ccgttcatgtgcctgtatgg (SEQ ID NO: 1)<br>Lower Sequence: tgttgcaggaaggtgacaca (SEQ ID NO: 2)<br>SP-4009Gc: ttggaaggaacatctagcagg (SEQ ID NO: 3) |
| M2 (Sd1) | G2003 | PCR | 38,109,578 | TG2003U: cacagcgctcacttctca (SEQ ID NO: 4)<br>TG2003L: tgcaatgtcgtccaccatcg (SEQ ID NO: 5) |
| M3 (Sd1) | G2002 | PCR | 38,109,641 | TG2002U: cacagcgctcacttctca (SEQ ID NO: 6)<br>TG2002L: atgatcgtcagcgacagct (SEQ ID NO: 7) |
| M4 (Sd1) | SP-462 | SNP | 38,199,633 | Upper Sequence: aactccagcgtgctaagc (SEQ ID NO: 8)<br>Lower Sequence: gcattgcatgcaggatcg (SEQ ID NO: 9)<br>SP-462Gt: agagcccttcactttcagc (SEQ ID NO: 10) |
| M5 (Sd1) | SP-1259 | SNP | 38,949,811 | Upper Sequence: aaggctgatgagcactgc (SEQ ID NO: 11)<br>Lower Sequence: ggcattgtggaagctcttc (SEQ ID NO: 12)<br>SP-1259Tc: tctcctttcggagtccc (SEQ ID NO: 13) |

Then, the resulting chromosome fragment-substituted line and Koshihikari were mated to harvest 10 progeny individuals (seeds) in which the DNA marker M3 (Sd1) is a hetero-chromosome region of an allele derived from Koshihikari and an allele derived from Habataki. All of the resulting seeds were cultivated, and self-fertilized (self-mated) to harvest a seed which is a progeny individual.

This harvested seed was cultivated. After a seedling was grown to such an extent that the seedling could be transplanted to an agricultural field, a DNA was extracted from a leaf of each cultivated individual, and a cultivated individual in which the DNA marker M1 (Sd1) is a homo-chromosome region of an allele derived from Koshihikari, and DNA markers M2 (Sd1) and M3 (Sd1) are a hetero-chromosome region of an allele derived from Koshihikari and an allele derived from Habataki, was selected.

This selected cultivated individual was self-fertilized (self-mated) to harvest a seed which is a progeny individual. This harvested seed was further cultivated, and a seedling was grown to such an extent that the seedling could be transplanted to an agricultural field, a DNA was extracted from a leaf of each cultivated individual, and one cultivated individual in which DNA markers M1 (Sd1) and M5 (Sd1) are a homo-chromosome region of an allele derived from Koshihikari, and the DNA markers M2 (Sd1), M3 (Sd1) and M4 (Sd1) are a homo-chromosome region of an allele derived from Habataki was selected. This selected cultivated individual is a new cultivar in which a region between the DNA marker M1 (Sd1) and the DNA marker M5 (Sd1) of a Sd1 region of Koshihikari is substituted with a chromosome fragment derived from Habataki. Thus in Table 1, DNA markers M1 (Sd1) and M5 (Sd1) are a homo-chromosome region of an allele derived from Koshihikari, and the DNA markers M2 (Sd1), M3 (Sd1) and M4 (Sd1) are a homo-chromosome region of an allele derived from Habataki. The present inventors named this new cultivar as "Koshihikari eichi 4go".

Figure 16:
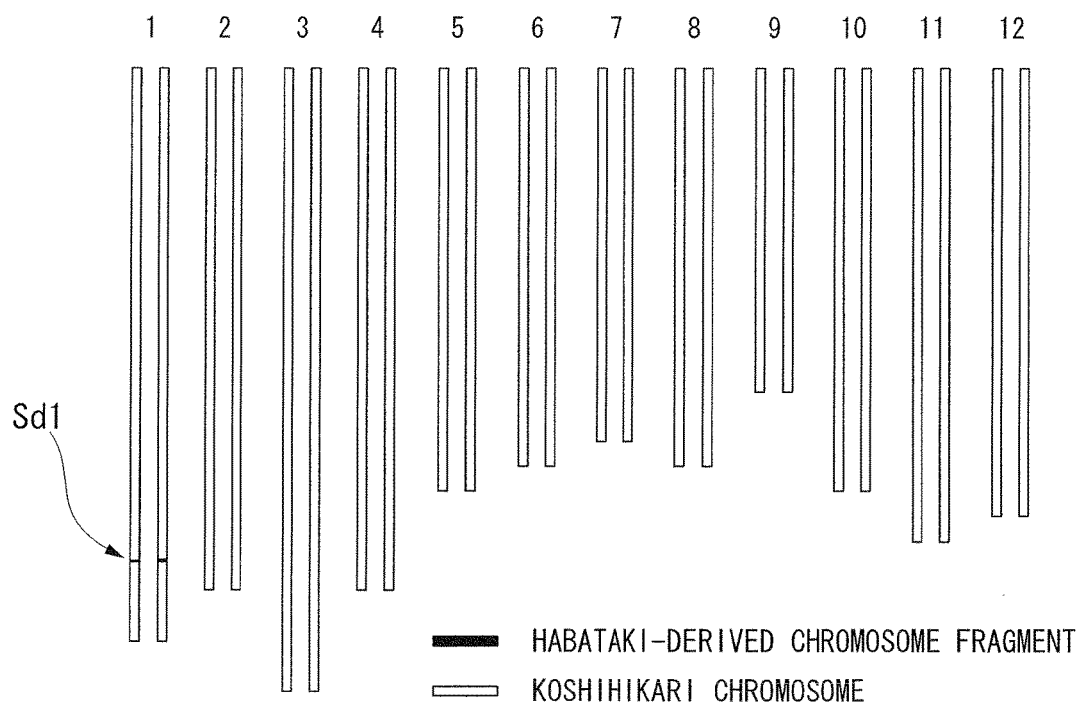
FIG. 16 is a view schematically showing a genome of Koshihikari eichi 4go.

FIG. 16 is a view schematically showing a genome of Koshihikari eichi 4go.

Figure 17:
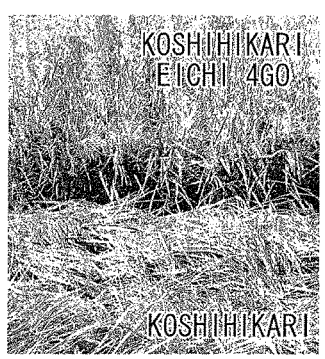
FIG. 17 is a view comparing lodging resistance of Koshihikari eichi 4go and Koshihikari. A front agricultural field is the field of Koshihikari, and back agricultural field is the field of Koshihikari eichi 4go.

Characters between Koshihikari eichi 4go, Koshihikari and Nihonbare were compared, and studied (implemented in Aichi Prefecture in 2005 to 2006). Study of characters was performed according to Property Examination for filing Cultivar Registration based on Plant Cultivar Protection and Seed Act (Year Heisei 10, Law No. 83), Article 5, Section 1. The results are shown in Tables 2 to 4. A rod length of Koshihikari and Nihonbare which are a control cultivar was 99.0 cm and 86.8 cm, respectively, while a rod length of Koshihikari eichi 4go was as short as 83.3 cm. On the other hand, Koshihikari eichi 4go was fundamentally the same as Koshihikari except that a rod length was short, and had a good character of pre-harvest sprouting difficulty of Koshihikari. Further, as shown in FIG. 17, by a rod length being reduced, lodging resistance was also enhanced.

Therefore, from these results, it is clear that, by designing a genome using the method of plant genome design of the present invention, and creating a new cultivar using the method of creating a new cultivar of the present invention, a new cultivar having a character of a target can be created without changing a preferable character possessed by the original cultivar.

TABLE 2

| Stage | Character | Property value of cultivar (comparison with standard cultivar) | | | | | | | | | Remark Value measured in Aichi Prefecture (2005-2006) | Property value of control cultivar | |
|---|---|---|---|---|---|---|---|---|---|---|---|---|---|
| | | 1 | 2 | 3 | 4 | 5 | 6 | 7 | 8 | 9 | | Koshihikari (Aichi Prefecture, 2005-2006) | Nihonbare (Aichi Prefecture, 2006) |
| 40 | Leaf: Anthocyanine coloring | Absence | | | | | | | | Presence | 1 | 1 | 1 |
| | Leaf: Distribution of anthocyanine color | Only tip | Only edge | Spot-like | Whole leaf | | | | | | 1 | 1 | 1 |
| | Leaf: Anthocyanine color of auricle | Absence | | | | | | | | Presence | 1 | 1 | 1 |
| 60 | Flag leaf: Posture of leaf blade (Initial observation) | Stand | | Hemi-stand | | Horizontal | | Recurved | | | 3 | 3 | 3 |
| 90 | Flag leaf: Posture of leaf blade (Late observation) | Stand | | Hemi-stand | | Horizontal | | Recurved | | | 3 | 4 | 4 |
| 55 | Heading time (50% ear emergence) | Extremely early | | Early | | Intermediate | | Late | | | 3 August 7 | 3 August 7 | 4 August 17 |
| 65 | Lemma: Anthocyanine coloring of top part (initial observation) | Absence or extremely pale | | Pale | | Intermediate | | Strong | | Extremely strong | 1 | 1 | 1 |

TABLE 3

| Stage | Character | Property value of cultivar (comparison with standard cultivar) | | | | | | | | | Remark Value measured in Aichi Prefecture (2005-2006) | Property value of control cultivar | |
|---|---|---|---|---|---|---|---|---|---|---|---|---|---|
| | | 1 | 2 | 3 | 4 | 5 | 6 | 7 | 8 | 9 | | Koshihikari (Aichi Prefecture, 2005-2006) | Nihonbare (Aichi Prefecture, 2006) |
| 70 | Rod: Length (expect for ear, expect for floating rice) | Extremely short | | Short | | Intermediate | | Long | | Extremely long | 4 83.3 cm | 6 99.0 cm | 5 86.8 cm |

TABLE 3-continued

| | | Property value of cultivar (comparison with standard cultivar) | | | | | | | | Remark Value measured in Aichi Prefecture (2005-2006) | Property value of control cultivar | |
|---|---|---|---|---|---|---|---|---|---|---|---|---|
| | | | | | | | | | | | Koshihikari (Aichi Prefecture, 2005-2006) | Nihonbare (Aichi Prefecture, 2006) |
| Stage | Character | 1 | 2 | 3 | 4 | 5 | 6 | 7 | 8 | 9 | | | |
| | Rod: Anthocyanine coloring of knot | Absence | | | | | | | | Presence | 1 | 1 | 1 |
| 72-90 | Ear: Length of main axis | | | Short | | Intermediate | | Long | | | 4 16.5 cm | 4 16.8 cm | 4 16.4 cm |
| 70 | Ear: Ear number | | | Small | | Intermediate | | Much | | | 5 15.3 ears | 5 15.3 ears | 5 12.0 ears |
| 70-80 | Ear: distribution of arista | Only tip | | Only Upper half | | Whole | | | | | 1 | 1 | 1 |
| 60-80 | Small ear: Much or less of trichome of lemma | Absence or extremely small | | Small | | Intermediate | | Much | | Extremely much | Equivalent to Koshihikari | | |
| 80-90 | Small ear: Color of lemma tip (apiculus color) | White | Yellow | Brown | Red | Purple | Black | | | | 1 | 1 | 1 |
| 90 | Ear: Curvature extent of main axis | Stand | | Tilt | | Hanging | | Bending | | | 5 | 5 | 5 |
| | Ear: Ear type | Lanceolate | Spindle-like | Bat-like | Bloom-like | Umbellar | | | | | 2 | 2 | 2 |
| | Maturing stage | Extremely early | | Early | | Intermediate | | Late | | Extremely late | 5 September 16 | 5 September 16 | 6 September 28 (2007) |
| | Glume color | Yellowish white | Gold color | Brown | Reddish pale purple | Purple | Black | | | | 1 | 1 | 1 |
| | Glume color: Pattern | Absence | Golden groove | Brown groove | Purple spot | Purple groove | | | | | 1 | 1 | 1 |

TABLE 4

| | | Property value of cultivar (comparison with standard cultivar) | | | | | | | | Remark Value measured in Aichi Prefecture (2005-2006) | Property value of control cultivar | |
|---|---|---|---|---|---|---|---|---|---|---|---|---|
| | | | | | | | | | | | Koshihikari (Aichi Prefecture, 2005-2006) | Nihonbare (Aichi Prefecture, 2006) |
| Stage | Character | 1 | 2 | 3 | 4 | 5 | 6 | 7 | 8 | 9 | | | |
| 92 | Lemma: Anthocyanine coloring of top part | Absence or extremely pale | | Pale | | Intermediate | | Deep | | Extremely deep | 1 | 1 | 1 |
| | Lemma: length | | | Short | | Intermediate | | Long | | | 2 1.90 mm | 2 1.68 mm | 2 2.01 mm |
| | Lemma: Color | Yellowish white | Gold color | Red | Purple | | | | | | 1 | 1 | 1 |
| | Paddy: 1,000 particles weight (mature) | | | Light | | Intermediate | | Heavy | | | 5 24.74 g | 5 24.43 g | 5 26.1 g |
| | Paddy: Phenol reaction of palea | Absence | | Pale | | Intermediate | | Deep | | Presence | 1 | 1 | 1 |
| | Brown rice: Length | | | Short | | Intermediate | | Long | | | 5 5.03 mm | 5 5.02 mm | 5 5.26 mm |
| | Brown rice: Width | | | Thin | | Intermediate | | Thick | | | 5 2.90 mm | 5 2.91 mm | 5 2.88 mm |
| | Brown rice: | Circular | Half | Half | Spindle- | Long | | | | | 2 | 2 | 2 |

TABLE 4-continued

| Stage | Character | Property value of cultivar (comparison with standard cultivar) | | | | | | | | | Remark Value measured in Aichi Prefecture (2005-2006) | Property value of control cultivar | |
|---|---|---|---|---|---|---|---|---|---|---|---|---|---|
| | | 1 | 2 | 3 | 4 | 5 | 6 | 7 | 8 | 9 | | Koshihikari (Aichi Prefecture, 2005-2006) | Nihonbare (Aichi Prefecture, 2006) |
| | Shape (seen from side) | | circular | spindle-shape | shape | spindle-shape | | | | | 1.85 mm | 1.86 mm | 2.01 mm |
| | Brown rice: Color | White | Pale brown | Brown spot | Dark brown | Pale red | Red | Purple spot | Purple | Dark purple/black | 2 | 2 | 2 |
| | Brown rice: Fragrances | Absence or extremely weak | Faint | Strong | | | | | | | 1 | 1 | 1 |

Example 2

Using the present invention, a new cultivar in which seeds setting density of a rice cultivar Koshihikari was enhanced was created.

First, a rice cultivar Habataki and a rice cultivar Koshihikari were mated, and QTL analysis was performed in a segregated population. As a result, it became clear that QTL having a higher seeds setting density than that of Koshihikari was present in an about 5 Mp region of a first chromosome. That is, it became clear that a Gn1 gene present in the region is a causal gene of controlling seeds setting density. Then, it was predicted that when a Gn1 gene of Koshihikari is substituted with a gene region derived from Habataki, seeds setting density of Koshihikari is increased. Then, Habataki was backcrossed with Koshihikari to create a chromosome fragment-substituted line in which a region containing a Gn1 gene of Koshihikari is substituted with a gene fragment derived from Habataki.

Figure 18:
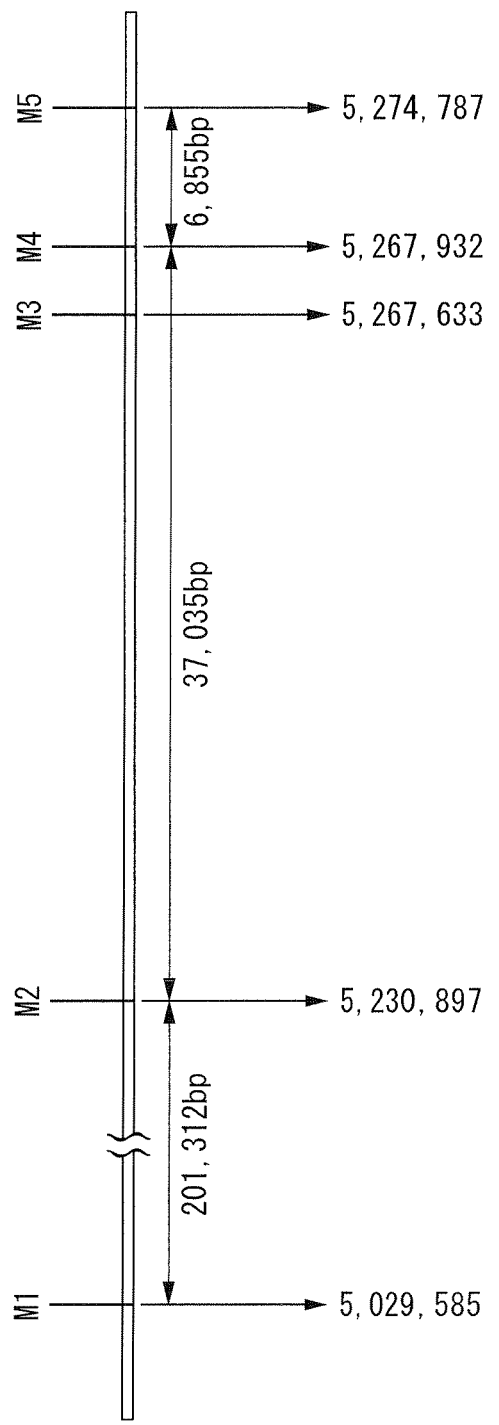
FIG. 18 is a view showing a DNA marker used in creating Koshihikari eichi 2go.

Then, according to the method of plant genome design of the present invention, a length of a chromosome fragment region derived from Habataki of the resulting chromosome fragment-substituted line was regulated to design a genome. Specifically, a DNA marker SP-2032 in a Gn1 gene region was let to be a DNA marker M1 (Gn1), a DNA marker SP-170 in a Gn1 gene region was let to be a DNA marker M2 (Gn1), a DNA marker SP-4028 in a Gn1 gene region was let to be a DNA marker M3 (Gn1), a DNA marker SP-4038 in a Gn1 gene region was let to be a DNA marker M4 (Gn1), and a DNA marker SP-4030 in a Gn1 gene region was let to be a DNA marker M5 (Gn1). These DNA markers are shown in FIG. 18 and Table 5. A distance d1 between DNA markers M1 (Gn1) and M2 (Gn1) is about 201 kbp, a distance d2 between DNA markers M2 (Gn1) and M4 (Gn1) is about 37 kbp, and a distance d3 between DNA markers M4 (Gn1) and M5 (Gn1) is about 7 kbp. Thereby, in a chromosome of Koshihikari, a length of a chromosome fragment $L_2$ derived from Habataki becomes 37 kbp<$L_2$<246 kbp.

TABLE 5

| | Marker | Type | Position | Sequence (SEQ ID NOS 14-28, respectively, in order of appearance) |
|---|---|---|---|---|
| M1 (Gn1) (Also referred to as "M6") | SP-2032 | SNP | 5,029,585 | Upper Sequence: cattgagtccatttcctctgc_ (SEQ ID NO: 14)<br>Lower Sequence: gcagctccaagaatgactac (SEQ ID NO: 15)<br>SP-2032Tg: attggtgctagagcaactac (SEQ ID NO: 16) |
| M2 (Gn1) (Also referred to as "M7") | SP-170 | SNP | 5,230,897 | Upper Sequence: gtgagacatagactatccac (SEQ ID NO: 17)<br>Lower Sequence: acgcgtacgccacatagac (SEQ ID NO: 18)<br>SP-170Ta: agggtgaggaatgtccggt (SEQ ID NO: 19) |
| M3 (Gn1) (Also referred to as "M8") | SP-4028 | SNP | 5,267,633 | Upper Sequence: gcagtacctgccttactacg (SEQ ID NO: 20)<br>Lower Sequence: catttcatgcgagtggtgac (SEQ ID NO: 21)<br>SP-4028Ac: tgcacgaatcttggccagag (SEQ ID NO: 22) |
| M4 (Gn1) (Also referred to as "M9") | SP-4038 | SNP | 5,267,932 | Upper Sequence: cttaaactcaacttgcacaagtag (SEQ ID NO: 23)<br>Lower Sequence: actgccgacatgttactgtc (SEQ ID NO: 24)<br>SP-4038Gc: gtccacctgaaacatatcca (SEQ ID NO: 25) |

TABLE 5-continued

| Marker | Type | Position | Sequence (SEQ ID NOS 14-28, respectively, in order of appearance) |
|---|---|---|---|
| M5 (Gn1) (Also referred to as "M10") | SP-4030 SNP | 5,274,787 | Upper Sequence: tctttgattctttggtcgatcg (SEQ ID NO: 26)<br>Lower Sequence: gcgtacgagagctatagagc (SEQ ID NO: 27)<br>SP-4030At: atggatccgtggatcgatcg (SEQ ID NO: 28) |

Figure 19:
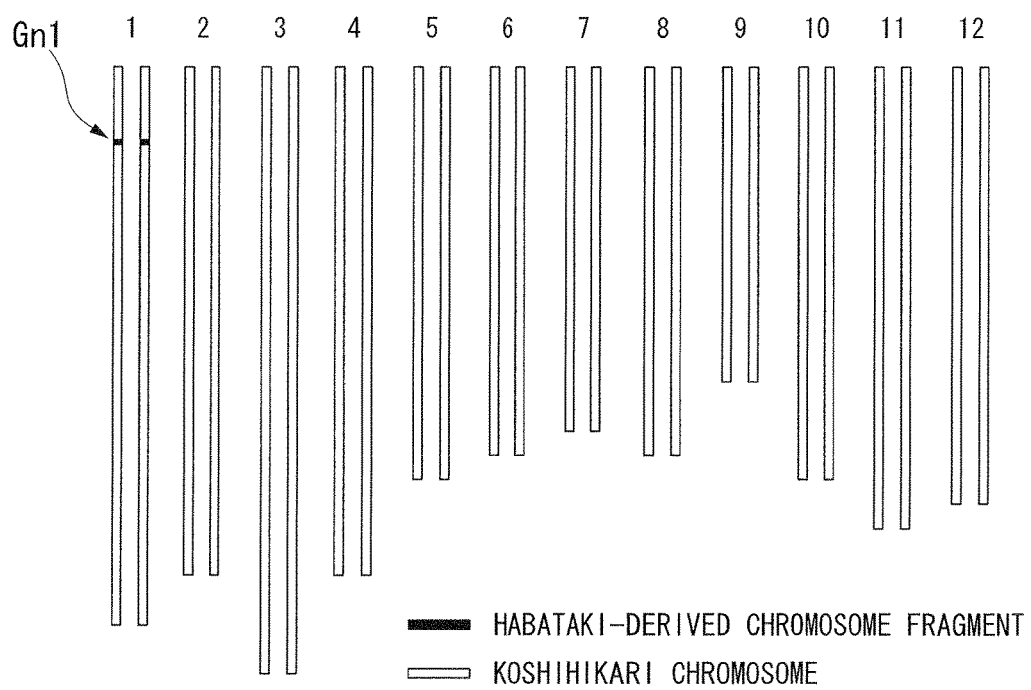
FIG. 19 is a view schematically showing a genome of Koshihikari eichi 2go.

Then, the resulting chromosome fragment-substituted line and Koshihikari was mated, and mating and selection were repeated as in Example 1 to select an individual of a new cultivar in which a region between a DNA marker M1 (Gn1) and a DNA marker M5 (Gn1) of a Gn1 gene region of Koshihikari is substituted with a chromosome fragment derived from Habataki. The present inventors named this new cultivar as "Koshihikari eichi 2go". FIG. 19 is a view schematically showing a genome of Koshihikari eichi 2go.

Characters between Koshihikari eichi 2go, Koshihikari and Nihonbare were compared and studied as in Example 1 (implemented in Aichi Prefecture in 2005 to 2006). The results are shown in Tables 6 to 8. In Tables, "(2005)" indicates a value measured in 2005, and "(2006)" indicates a value measured in 2006, respectively. Seeds setting density of Koshihikari which was a control cultivar was 7.01 grains/cm² in 2005, and 8.89 grains/cm² in 2006. Seeds setting density in 2006 of Nihonbare which was similarly a control cultivar was 5.99 grains/cm². To the contrary, Seeds setting density of Koshihikari eichi 2go was 10.7 grains/cm² in 2005, and 10.0 grains/cm² in 2006. Like this, Seeds setting density of Koshihikari eichi 2go was very higher and better than those of Koshihikari and Nihonbare. On the other hand, no significant difference was detected between Koshihikari eichi 2go and Koshihikari except for high seeds setting density. In addition, also in the case where an experiment was implemented in Niigata Prefecture in 2005 using Koshihikari and Dontokoi as a control cultivar, the approximately same results as those of Tables 6 to 8 were obtained.

Therefore, also from these results, it is clear that, by designing a genome using the method of plant genome design of the present invention, and creating a cultivar using the method of creating a new cultivar of the present invention, a new cultivar having a target character can be created without changing a preferable character possessed by the original cultivar.

TABLE 6

| Stage | Character | Property value of cultivar (comparison with standard cultivar) | | | | | | | | | Remark Value measured in Aichi Prefecture (2005-2006) | Property value of control cultivar | |
|---|---|---|---|---|---|---|---|---|---|---|---|---|---|
| | | 1 | 2 | 3 | 4 | 5 | 6 | 7 | 8 | 9 | | Koshihikari (Aichi Prefecture, 2005-2006) | Nihonbare (Aichi Prefecture, 2006) |
| 40 | Leaf: Anthocyanine coloring | Absence | | | | | | | | Presence | 1 | 1 | 1 |
| | Leaf: Distribution of anthocyanine color | Only tip | Only edge | Spot-like | Whole leaf | | | | | | 1 | 1 | 1 |
| | Leaf: Anthocyanine color of auricle | Absence | | | | | | | | Presence | 1 | 1 | 1 |
| 60 | Flag leaf: Posture of leaf blade (Initial observation) | Stand | | Hemi-stand | | Horizontal | | Recurved | | | 3 | 3 | 2 |
| 90 | Flag leaf: Posture of leaf blade (Late observation) | Stand | | Hemi-stand | | Horizontal | | Recurved | | | 4 | 4 | 4 |
| 55 | Heading time (50% ear emergence) | Extremely early | | Early | | Intermediate | | Late | | | 3<br>August 5 (2005)<br>August 8 (2006) | 3<br>August 5 (2005)<br>August 9 (2006) | 4<br>August 17 |
| 65 | Lemma: Anthocyanine coloring of top part (initial observation) | Absence or extremely pale | | Pale | | Intermediate | | Strong | | Extremely strong | 1 | 1 | 1 |

TABLE 7

| Stage | Character | Property value of cultivar (comparison with standard cultivar) | | | | | | | | | Remark Value measured in Aichi Prefecture (2005-2006) | Property value of control cultivar Koshihikari (Aichi Prefecture, 2005-2006) | Nihonbare (Aichi Prefecture, 2006) |
|---|---|---|---|---|---|---|---|---|---|---|---|---|---|
| | | 1 | 2 | 3 | 4 | 5 | 6 | 7 | 8 | 9 | | | |
| 70 | Rod: Length (expect for ear, expect for floating rice) | Extremely short | | Short | | Intermediate | | Long | | Extremely long | 6 105.0 cm (2005) 95.5 cm (2006) | 6 108.9 cm (2005) 101.0 cm (2006) | 5 86.8 cm |
| | Rod: Anthocyanine coloring of knot | Absence | | | | | | | | Presence | 1 | 1 | 1 |
| 72-90 | Ear: Length of main axis | | | Short | | Intermediate | | Long | | | 4 18.0 cm (2005) 15.7 cm (2006) | 4 18.8 cm (2005) 15.1 cm (2006) | 4 16.4 cm |
| 70 | Ear: Ear number | | | Small | | Intermediate | | Much | | | 5 17.0 ears (2005) 11.2 ears (2006) | 5 16.8 ears (2005) 13.4 ears (2006) | 5 12.0 ears |
| 70-80 | Ear: distribution of arista | Only tip | | Only Upper half | | Whole | | | | | 1 | 1 | 1 |
| 60-80 | Small ear: Much or less of trichome of lemma | Absence or extremely small | | Small | | Intermediate | | Much | | Extremely much | Equivalent to Koshihikari | | |
| 80-90 | Small ear: Color of lemma tip (apiculus color) | White | Yellow | Brown | Red | Purple | Black | | | | 1 | 1 | 1 |
| 90 | Ear: Curvature extent of main axis | Stand | | Tilt | | Hanging | | Bending | | | 5 | 5 | 5 |
| | Ear: Ear type | Lanceolate | Spindle-like | Bat-like | Bloom-like | Umbellar | | | | | 2 | 2 | 2 |
| | Maturing stage | Extremely early | | Early | | Intermediate | | Late | | Extremely late | 5 September 15 (2005) September 18 (2006) | 5 September 18 (2005) September 19 (2006) | 6 September 28 (2007) |
| | Glume color | Yellowish white | Gold color | Brown | Reddish pale purple | Purple | Black | | | | 1 | 1 | 1 |
| | Glume color: Pattern | Absence | Golden groove | Brown groove | Purple spot | Purple groove | | | | | 1 | 1 | 1 |

TABLE 8

| Stage | Character | Property value of cultivar (comparison with standard cultivar) | | | | | |
|---|---|---|---|---|---|---|---|
| | | 1 | 2 | 3 | 4 | 5 | 6 |
| 92 | Lemma: Anthocyanine coloring of top part | Absence or extremely pale | | Pale | | Intermediate | |
| | Lemma: length | | | Short | | Intermediate | |
| | Lemma: Color | Yellowish white | Gold color | Red | Purple | | |
| | Paddy: 1,000 particles weight (mature) | | | Light | | Intermediate | |
| | Paddy: Phenol reaction of palea | Absence | | Pale | | Intermediate | |

TABLE 8-continued

| Stage | Character | Property value of cultivar (comparison with standard cultivar) | | | | | | Remark Value measured in Aichi Prefecture (2005-2006) | Property value of control cultivar | |
|---|---|---|---|---|---|---|---|---|---|---|
| | | | | | | | | | Koshihikari (Aichi Prefecture, 2005-2006) | Nihonbare (Aichi Prefecture, 2006) |
| | Brown rice: Length | | | | Short | | Intermediate | | | |
| | Brown rice: Width | | | | Thin | | Intermediate | | | |
| | Brown rice: Shape (seen from side) | Circular | | Half circular | Half spindle-shape | Spindle-shape | Long spindle-shape | | | |
| | Brown rice: Color | White | | Pale brown | Brown spot | Dark brown | Pale red | Red | | |
| | Brown rice: Fragrances | Absence or extremely weak | | Faint | Strong | | | | | |
| GII | Seeds setting density | | | Very sparse | Sparse | Slightly sparse | Intermediate | Slightly dense | | |

| Stage | Character | 7 | 8 | 9 | Remark Value measured in Aichi Prefecture (2005-2006) | Koshihikari (Aichi Prefecture, 2005-2006) | Nihonbare (Aichi Prefecture, 2006) |
|---|---|---|---|---|---|---|---|
| 92 | Lemma: Anthocyanine coloring of top part | Deep | | Extremely deep | 1 | 1 | 1 |
| | Lemma: length | Long | | | 2<br>1.83 mm (2005)<br>2.22 mm (2006) | 2<br>1.70 mm (2005)<br>1.64 mm (2006) | 2<br>2.01 mm |
| | Lemma: Color | | | | 1 | 1 | 1 |
| | Paddy: 1,000 particles weight (mature) | Heavy | | | 5<br>24.4 g (2005)<br>25.4 g (2006) | 5<br>24.3 g (2005)<br>24.6 g (2006) | 5<br>26.1 g |
| | Paddy: Phenol reaction of palea | Deep | | Presence | 1 | 1 | 1 |
| | Brown rice: Length | Long | | | 5<br>4.95 mm (2005)<br>5.06 mm (2006) | 5<br>5.03 mm (2005)<br>4.98 mm (2006) | 5<br>5.26 mm |
| | Brown rice: Width | Thick | | | 5<br>3.01 mm (2005)<br>2.89 mm (2006) | 5<br>2.96 mm (2005)<br>2.86 mm (2006) | 5<br>2.88 mm |
| | Brown rice: Shape (seen from side) | | | | 2<br>1.98 mm (2005)<br>2.02 mm (2006) | 2<br>1.70 mm (2005)<br>2.03 mm (2006) | 2<br>2.01 mm |
| | Brown rice: Color | Purple spot | Purple | Dark purple/black | 2 | 2 | 2 |
| | Brown rice: Fragrances | | | | 1 | 1 | 1 |
| GII | Seeds setting density | Dense | Very dense | | 7<br>10.7 grains/cm² (2005)<br>10.0 grains/cm² (2006) | 6<br>7.01 grains/cm² (2005)<br>8.89 grains/cm² (2006) | 5<br>5.99 grains/cm² |

Example 3

When Koshihikari is cultivated in Hokkaido, a term from seeding to ear emergence is about 144 days and this is too long. That is, when a seed is planted mid-May, ear emergence does not occur until mid-September. However, after mid-September, an air temperature becomes lower in Hokkaido, and thereby Koshihikari cannot be normally matured. For this reason, in order to cultivate Koshihikari in a north district such as Hokkaido and the like, conversion into early growth of Koshihikari is necessary. Then, using the present invention, a new cultivar of a rice cultivar Koshihikari which had been converted into early growth was created.

First, a rice cultivar Habataki and a rice cultivar Koshihikari were mated, and QTL analysis was performed in a segregated population. As a result, QTL which converts Koshihikari into early growth in a tropical region was revealed. That is, it was indicated that there was a high possibility that a Hd1 gene present in the region was a causal gene of controlling conversion into early growth. Then, Habataki was backcrossed with Koshihikari to create a chromosome fragment-substituted line in which a region containing a Hd1 gene of Koshihikari was substituted with a gene fragment derived from Habataki.

Figure 20:
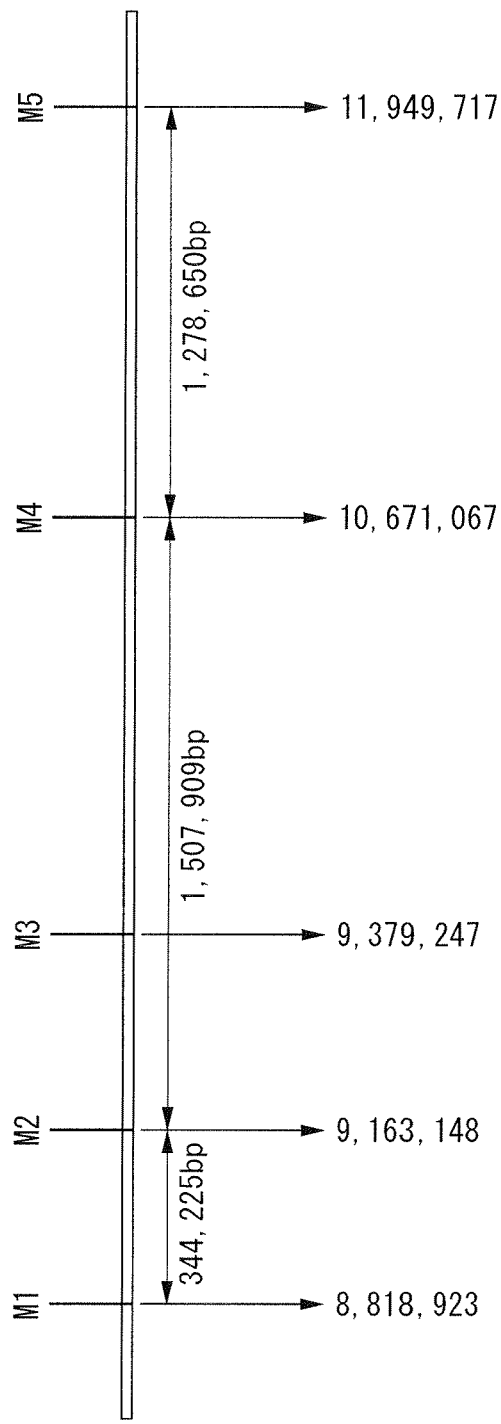
FIG. 20 is a view showing a DNA marker used in creating Koshihikari eichi 3go.

Then, according to the method of plant genome design of the present invention, a length of a chromosome fragment region derived from Habataki of the resulting chromosome fragment-substituted line was regulated to design a genome. Specifically, a DNA marker SP-2513 in the Hd1 gene region was let to be a DNA marker M1 (Hd1), a DNA marker SP-586 in the Hd1 gene region was let to be a DNA marker M2 (Hd1), a DNA marker SP-2254 in the Hd1 gene region was let to be a DNA marker M3 (Hd1), a DNA marker SP-1603 in the Hd1 gene region was let to be a DNA marker M4 (Hd1), and a DNA marker SP-604 in the Hd1 gene region was let to be a DNA marker M5 (Hd1). These DNA markers are shown in FIG. 20 and Table 9. A distance d1 between the DNA markers M1 (Hd1) and M2 (Hd1) is about 344 kbp, a distance d2 between the DNA markers M2 (Hd1) and M4 (Hd1) is about 1,508 kbp, and a distance d3 between the DNA markers M4 (Hd1) and M5 (Hd1) is about 1,279 kbp. Thereby, a length of a chromosome fragment $L_2$ derived from Habataki in a chromosome of Koshihikari becomes 1,507 kbp<$L_2$<3,131 kbp.

be transplanted to an agricultural field, a DNA was extracted from a leaf of each cultivated individual, and a cultivated individual in which the DNA marker M1 (Hd1) is a homo-chromosome region of an allele derived from Koshihikari, and the DNA markers M2 (d1) and M3 (Hd1) are a hetero-chromosome region of an allele derived from Koshihikari and an allele derived from Habataki was selected.

This selected cultivated individual was self-fertilized (self-mated), and seeds which are a further progeny individual were harvested. The harvested seeds were further cultivated, a seedling was grown to such an extent that it could be transplanted to an agricultural field, a DNA was extracted from a leaf of each cultivated individual, and one cultivated individual in which the DNA markers M1 (Hd1) and M5 (Hd1) are a homo-chromosome region of an allele derived from Koshihikari, and the DNA markers M2 (Hd1), M3 (Hd1) and M4 (Hd1) are a homo-chromosome region of an allele derived from Habataki was selected. This selected cultivated individual is a new cultivar in which a region between the DNA marker M1 (Hd1) and the DNA marker M5 (Hd1) of the Hd1 region of Koshihikari is substituted with a chromosome fragment derived from Habataki. Thus in Table 9, the DNA markers M6 (Hd1) and M10 (Hd1) are a homo-chromosome region of an allele derived from Koshihikari, and the DNA markers M7 (Hd1), M8 (Hd1) and M9 (Hd1) are a homo-chromosome region of an allele derived

TABLE 9

| Marker | Type | Position | Sequence (SEQ ID NOS 29-43, respectively, in order of appearance) |
|---|---|---|---|
| M1 (Hd1) (Also referred to as "M11") | SP-2513 | SNP | 8,818,923 | Upper Sequence: gcgaaaagatgaggatgtacac (SEQ ID NO: 29)<br>Lower Sequence: ccgtaggcctttgtcaagtg (SEQ ID NO: 30)<br>SP-2513Ct: ctttaatggtggcttatgtc (SEQ ID NO: 31) |
| M2 (Hd1) (Also referred to as "M12") | SP-586 | SNP | 9,163,148 | Upper Sequence: gctaggacaagcttatttcagc (SEQ ID NO: 32)<br>Lower Sequence: tcacgccgatcaagaacg (SEQ ID NO: 33)<br>SP-586Ca: cataatttatcgccattttcgcat (SEQ ID NO: 34) |
| M3 (Hd1) (Also referred to as "M13") | SP-2254 | SNP | 9,379,247 | Upper Sequence: aggcccttgtactggtac (SEQ ID NO: 35)<br>Lower Sequence: gtacacaatagttggtgcacc (SEQ ID NO: 36)<br>SP-2254Cg: catgataaggtactcctgg (SEQ ID NO: 37) |
| M4 (Hd1) (Also referred to as "M14") | SP-1603 | SNP | 10,671,067 | Upper Sequence: cctagtccctaaagatctcatg (SEQ ID NO: 38)<br>Lower Sequence: gatagacatgacggagaagtg (SEQ ID NO: 39)<br>SP-1603Tc: gggtggtgttatctctagt (SEQ ID NO: 40) |
| M5 (Hd1) (Also referred to as "M15") | SP-604 | SNP | 11,949,717 | Upper Sequence: gcgcaaattccttcagtcac (SEQ ID NO: 41)<br>Lower Sequence: cagtttcaggtggaagacc (SEQ ID NO: 42)<br>SP-604Tc: caagtttcttcctctcattttc (SEQ ID NO: 43) |

Then, the resulting chromosome fragment-substituted line and Koshihikari were mated to harvest three progeny individuals (seed) in which the DNA marker M3 is a hetero-chromosome region of an allele derived from Koshihikari and an allele derived from Habataki. All of the resulting seeds were cultivated, self-fertilized (self-mated), and seeds which are a further progeny individual were harvested.

The harvested seeds were further cultivated. After a seedling was grown to such an extent that the seedling could from Habataki. The present inventors named this new cultivar as "Koshihikari eichi 3go".

Figure 21:
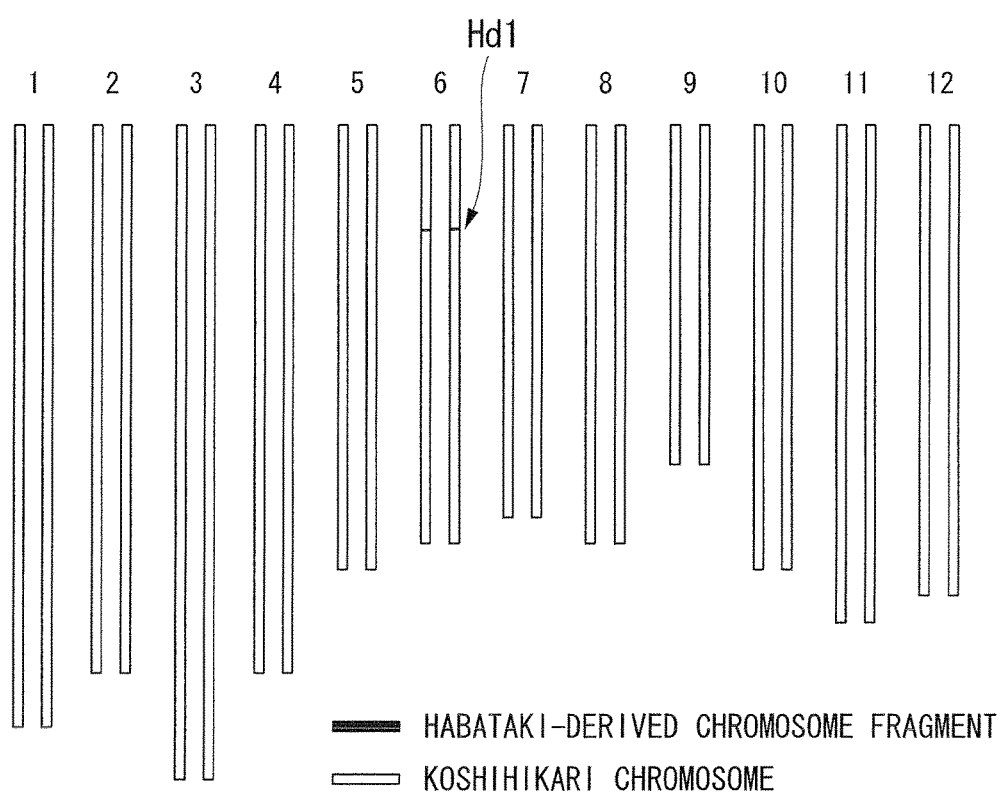
FIG. 21 is a view schematically showing a genome of Koshihikari eichi 3go.

FIG. 21 is a view schematically showing a genome of Koshihikari eichi 3go.

Characters between Koshihikari eichi 3go Koshihikari and Nihonbare were compared and studied as in Example 1 (implemented in Aichi Prefecture in 2005 to 2006). Study results are shown in Tables 10 to 12. In Tables "(2005)" indicates a value measured in 2005, and "(2006)" indicates a value measured in 2006, respectively. A heading time of Koshihikari and Nihonbare which were a control cultivar was August 7 and August 17, respectively, while a heading time of Koshihikari eichi 3go was July 27, being 10 days earlier than those of the control cultivars. In addition, a maturing term of Koshihikari and Nihonbare was September 18 and September 28, respectively, while the maturing term of Koshihikari eichi 3go was September 7, and it was seen that as a heading time becomes earlier, a maturing term becomes earlier. In addition, due to an earlier heading time, a rod length of Koshihikari eichi 3go was reduced. On the other hand, other characters of Koshihikari eichi 3go were fundamentally the same as those of Koshihikari, and Koshihikari eichi 3go also had a good character of pre-harvest sprouting difficulty possessed by Koshihikari.

TABLE 10

| Stage | Character | Property value of cultivar (comparison with standard cultivar) | | | | | | | | | Remark Value measured in Aichi Prefecture (2005-2006) | Property value of control cultivar Koshihikari (Aichi Prefecture, 2005-2006) | Nihonbare (Aichi Prefecture, 2006) |
|---|---|---|---|---|---|---|---|---|---|---|---|---|---|
| | | 1 | 2 | 3 | 4 | 5 | 6 | 7 | 8 | 9 | | | |
| 40 | Leaf: Anthocyanine coloring | Absence | | | | | | | | Presence | 1 | 1 | 1 |
| | Leaf: Distribution of anthocyanine color | Only tip | Only edge | Spot-like | Whole leaf | | | | | | 1 | 1 | 1 |
| | Leaf: Anthocyanine color of auricle | Absence | | | | | | | | Presence | 1 | 1 | 1 |
| 60 | Flag leaf: Posture of leaf blade (Initial observation) | Stand | | Hemi-stand | | Horizontal | | Recurved | | | 3 | 3 | 3 |
| 90 | Flag leaf: Posture of leaf blade (Late observation) | Stand | | Hemi-stand | | Horizontal | | Recurved | | | 4 | 4 | 4 |
| 55 | Heading time (50% ear emergence) | Extremely early | | Early | | Intermediate | | Late | | | 2 July 27 | 3 August 7 | 4 August 17 |
| 65 | Lemma: Anthocyanine coloring of top part (initial observation) | Absence or extremely pale | | Pale | | Intermediate | | Strong | | Extremely strong | 1 | 1 | 1 |

TABLE 11

| Stage | Character | Property value of cultivar (comparison with standard cultivar) | | | | | | | | | Remark Value measured in Aichi Prefecture (2005-2006) | Property value of control cultivar Koshihikari (Aichi Prefecture, 2005-2006) | Nihonbare (Aichi Prefecture, 2006) |
|---|---|---|---|---|---|---|---|---|---|---|---|---|---|
| | | 1 | 2 | 3 | 4 | 5 | 6 | 7 | 8 | 9 | | | |
| 70 | Rod: Length (expect for ear, expect for floating rice) | Extremely short | | Short | | Intermediate | | Long | | Extremely long | 4 83.7 cm | 6 105.0 cm | 5 86.8 cm |
| | Rod: Anthocyanine coloring of knot | Absence | | | | | | | | Presence | 1 | 1 | 1 |
| 72-90 | Ear: Length of main axis | | | Short | | Intermediate | | Long | | | 4 18.0 cm | 4 17.0 cm | 4 16.4 cm |
| 70 | Ear: Ear number | | | Small | | Intermediate | | Much | | | 5 18.0 ears | 5 15.1 ears | 5 12.0 ears |
| 70-80 | Ear: distribution of arista | Only tip | | Only Upper half | | Whole | | | | | 1 | 1 | 1 |

TABLE 11-continued

| | | Property value of cultivar (comparison with standard cultivar) | | | | | | | | Remark Value measured in Aichi Prefecture | Property value of control cultivar | |
|---|---|---|---|---|---|---|---|---|---|---|---|---|
| | | | | | | | | | | | Koshihikari (Aichi Prefecture, | Nihonbare (Aichi Prefecture, |
| Stage | Character | 1 | 2 | 3 | 4 | 5 | 6 | 7 | 8 | 9 | (2005-2006) | 2005-2006) | 2006) |
| 60-80 | Small ear: Much or less of trichome of lemma | Absence or extremely small | | Small | | Intermediate | | Much | | Extremely much | Equivalent to Koshihikari | | |
| 80-90 | Small ear: Color of lemma tip (apiculus color) | White | Yellow | Brown | Red | Purple | | Black | | | 1 | 1 | 1 |
| 90 | Ear: Curvature extent of main axis | Stand | | Tilt | | Hanging | | Bending | | | 5 | 5 | 5 |
| | Ear: Ear type | Lanceolate | Spindle-like | Bat-like | Bloom-like | Umbellar | | | | | 2 | 2 | 2 |
| | Maturing stage | Extremely early | | Early | | Intermediate | | Late | | Extremely late | 4 September 7 | 5 September 18 | 6 September 28 |
| | Glume color | Yellowish white | Gold color | Brown | Reddish pale purple | Purple | | Black | | | 1 | 1 | 1 |
| | Glume color: Pattern | Absence | Golden groove | Brown groove | Purple spot | Purple groove | | | | | 1 | 1 | 1 |

TABLE 12

| | | Property value of cultivar (comparison with standard cultivar) | | | | | | | | Remark Value measured in Aichi Prefecture | Property value of control cultivar | |
|---|---|---|---|---|---|---|---|---|---|---|---|---|
| | | | | | | | | | | | Koshihikari (Aichi Prefecture, | Nihonbare (Aichi Prefecture, |
| Stage | Character | 1 | 2 | 3 | 4 | 5 | 6 | 7 | 8 | 9 | (2005-2006) | 2005-2006) | 2006) |
| 92 | Lemma: Anthocyanine coloring of top part | Absence or extremely pale | | Pale | | Intermediate | | Deep | | Extremely deep | 1 | 1 | 1 |
| | Lemma: length | | | Short | | Intermediate | | Long | | | 2 1.9 mm | 2 1.67 mm | 2 2.01 mm |
| | Lemma: Color | Yellowish white | Gold color | Red | Purple | | | | | | 1 | 1 | 1 |
| | Paddy: 1,000 particles weight (mature) | | | Light | | Intermediate | | Heavy | | | 5 26.0 g | 5 24.3 g | 5 26.1 g |
| | Paddy: Phenol reaction of palea | Absence | | Pale | | Intermediate | | Deep | | Presence | 1 | 1 | 1 |
| | Brown rice: Length | | | Short | | Intermediate | | Long | | | 5 5.05 mm | 5 5.00 mm | 5 5.26 mm |
| | Brown rice: Width | | | Thin | | Intermediate | | Thick | | | 5 2.96 mm | 5 2.91 mm | 5 2.88 mm |
| | Brown rice: Shape (seen from side) | Circular | Half circular | Half spindle-shape | Spindle-shape | Long spindle-shape | | | | | 2 2.05 mm | 2 1.87 mm | 2 2.01 mm |
| | Brown rice: Color | White | Pale brown | Brown spot | Dark brown | Pale red | Red | Purple spot | Purple | Dark purple/black | 2 | 2 | 2 |
| | Brown rice: Fragrances | Absence or extremely weak | Faint | Strong | | | | | | | 1 | 1 | 1 |

Actually, Koshihikari eichi 3go was cultivated in Hokkaido and, as a result, the growth of Koshihikari eichi 3go was earlier than that of Koshihikari by 24 days. In addition, Koshihikari eichi 3go was approximately normally matured unlike Koshihikari. Also from these results, it is clear that a new cultivar having a target character can be created without changing a preferable character possessed by the original cultivar, by designing a genome using the method of plant genome design of the present invention, and creating a cultivar using the method of creating a new cultivar of the present invention.

Thereafter, it was seen that a region containing the Hd1 gene of Habataki has interesting regulating function on Koshihikari. That is, a region containing the Hd1 gene of Habataki has the function of converting Koshihikari into early growth in a region northerner than Nagoya, but had the function of converting Koshihikari into late growth in a region Southerner than Okinawa. For example, when Koshihikari eichi 3go was cultivated in Nagoya, a growth of Koshihikari eichi 3go was converted into earlier growth than that of Koshihikari by about 10 days.

On the other hand, Koshihikari eichi 3go was cultivated in South Lawnsen of Ho chi minh in Vietnam having tropical weather and, as a result, the growth of Koshihikari eichi 3go was converted into later growth than that of Koshihikari by 11 days. That is, it was revealed that Koshihikari eichi 3go can be cultivated better in both of a north region and a south region.

Koshihikari is an excellent cultivar good in a taste, but in a north district, a term from seeding to ear emergence is too long, and Koshihikari cannot be safely ear-emerged and matured. Conversely, in a south district, since Koshihikari has a too short heading time, and cannot take a yield, a cultivating region thereof is limited. For example, when Koshihikari is cultivated in a tropical district, ear emergence occurs in only about 35 days, and a sufficient yield is not obtained in many cases. To the contrary, Koshihikari eichi 3go created using the method of creating a new cultivar of the present invention has excellent growth property of a very wide cultivatable region, while a good character of Koshihikari such as a taste and the like is retained.

Example 4

In order to improve yield property and lodging resistance of Koshihikari eichi 3go created in Example 3, a new cultivar Koshihikari kazusa 4go having all Habataki-derived chromosome regions possessed by Koshihikari eichi 2go, Koshihikari eichi 3go, and Koshihikari eichi 4go, respectively, was created using the fourth method of the present invention.

Specifically, Koshihikari eichi 3go and Koshihikari eichi 2go were mated, two of the resulting progeny individuals (seeds) were cultivated, and these were self-fertilized (self-mated). From progeny individuals obtained by this self-fertilizing, 100 seeds which were a further progeny individual were obtained. All of the 100 seeds were cultivated, DNA markers of respective progeny individuals were investigated, and one cultivated individual in which both of the DNA marker M3 (Hd1) and the DNA marker M3 (Gn1) are a homo-chromosome region of an allele derived from Habataki was selected. This individual was defined as P2 (HG).

According to the DNA markers of respective progeny individuals, respective individuals were grown, a DNA was extracted from a leaf sampled from a seedling, and analysis was performed using this DNA.

On the other hand, Koshihikari eichi 4go and Koshihikari eichi 2go were mated, five of the resulting progeny individuals (seeds) were cultivated, and these were self-fertilized (self-mated). From progeny individuals obtained by this self-fertilizing, 150 seeds which were a further progeny individual were obtained. All of the 150 seeds were cultivated, and DNA markers of respective progeny individuals were investigated, and one individual in which both of the DNA marker M3 (Sd1) and the DNA marker M3 (Gn1) are a homo-chromosome region of an allele derived from Habataki was selected. This individual was defined as P2 (SG).

Figure 22:
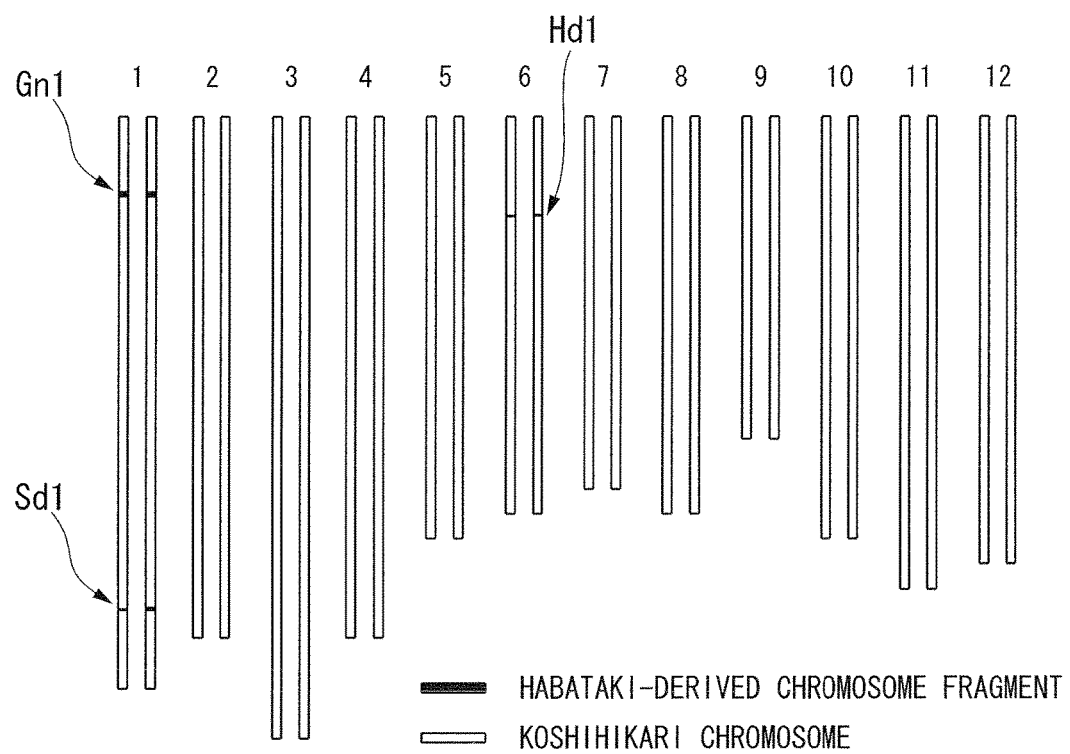
FIG. 22 is a view schematically showing a genome of Koshihikari kazusa 4go.

Then, P2 (HG) and P2 (SG) were mated, and two of the resulting progeny individuals (seeds) were cultivated, and these were self-fertilized (self-mated). From progeny individuals obtained this self-fertilizing, 100 seeds which are a further progeny individual were obtained. All of the 100 seeds were cultivated, DNA markers of respective progeny individuals were investigated, and one individual of a cultivated individual in which both of the DNA marker M3 (Hd1) and the DNA marker M3 (Sd1) were a homo-chromosome region of an allele derived from Habataki was selected. The present inventors named this new cultivar as "Koshihikari kazusa 4go". FIG. 22 is a view schematically showing a genome of Koshihikari kazusa 4go. In a chromosome of Koshihikari kazusa 4go, all of the Hd1 gene region, the Sd1 region and the Gn1 gene region are substituted with a homo-chromosome fragment derived from Habataki.

Characters between Koshihikari kazusa 4go Koshihikari and Nihonbare were compared and studied as in Example 1. The results are shown in Tables 13 to 16. Koshihikari kazusa 4go had a shorter rod length and higher lodging resistance as compared with Koshihikari and Nihonbare which are a control cultivar, like Koshihikari eichi 4go. In addition, like Koshihikari eichi 3go, a heading time of Koshihikari kazusa 4go was earlier by 9 days, and a maturing term of Koshihikari kazusa 4go was earlier than those of Koshihikari and Nihonbare. Further, like Koshihikari eichi 2go, seeds setting density of Koshihikari kazusa 4go was higher, and the number of main stem grains of Koshihikari kazusa 4go was greater than those of Koshihikari and Nihonbare. That is, in Koshihikari kazusa 4go, seeds setting density was higher relative to a length of an ear thereof. In addition, a weight per 1,000 paddies (mature) of Koshihikari kazusa 4go became higher than that of Koshihikari which was the original cultivar. Particularly, Koshihikari kazusa 4go had a very higher ear harvest coefficient than those of Koshihikari and Nihonbare, and it was seen that harvesting property of Koshihikari kazusa 4go was extremely good. On the other hand, Koshihikari kazusa 4go had fundamentally the same other characters as those of Koshihikari.

TABLE 13

| Stage | Character | Property value of cultivar (comparison with standard cultivar) | | | | | | | | | Remark Value measured | Property value of control cultivar | |
|---|---|---|---|---|---|---|---|---|---|---|---|---|---|
| | | 1 | 2 | 3 | 4 | 5 | 6 | 7 | 8 | 9 | | Koshihikari | Nihonbare |
| 40 | Leaf: Anthocyanine coloring | Absence | | | | | | | | Presence | 1 | 1 | 1 |
| | Leaf: Distribution of anthocyanine color | Only tip | Only edge | Spot-like | Whole leaf | | | | | | 1 | 1 | 1 |
| | Leaf: Anthocyanine color of auricle | Absence | | | | | | | | Presence | 1 | 1 | 1 |
| 60 | Flag leaf: Posture of leaf blade (Initial observation) | Stand | | Hemi-stand | | Horizontal | | Recurved | | | 3 | 3 | 3 |
| 90 | Flag leaf: Posture of leaf blade (Late observation) | Stand | | Hemi-stand | | Horizontal | | Recurved | | | 4 | 4 | 4 |
| 55 | Heading time (50% ear emergence) | Extremely early | | Early | | Intermediate | | Late | | | 2 July 30 | 3 August 8 | 4 August 19 |
| 65 | Lemma: Anthocyanine coloring of top part (initial observation) | Absence or extremely pale | | Pale | | Intermediate | | Strong | | Extremely strong | 1 | 1 | 1 |

TABLE 14

| Stage | Character | Property value of cultivar (comparison with standard cultivar) | | | | | | | | | Remark Value measured | Property value of control cultivar | |
|---|---|---|---|---|---|---|---|---|---|---|---|---|---|
| | | 1 | 2 | 3 | 4 | 5 | 6 | 7 | 8 | 9 | | Koshihikari | Nihonbare |
| 70 | Rod: Length (expect for ear, expect for floating rice) | Extremely short | | Short | | Intermediate | | Long | | Extremely long | 3 72.0 cm | 6 105.2 cm | 4 80.2 cm |
| | Rod: Anthocyanine coloring of knot | Absence | | | | | | | | Presence | 1 | 1 | 1 |
| 72-90 | Ear: Length of main axis | | | Short | | Intermediate | | Long | | | 4 15.1 cm | 4 14.7 cm | 4 14.6 cm |
| 70 | Ear: Ear number | | | Small | | Intermediate | | Much | | | 5 13.4 ears | 5 12.4 ears | 5 14 ears |
| 70-80 | Ear: distribution of arista | Only tip | | Only Upper half | | Whole | | | | | 1 | 1 | 1 |
| 60-80 | Small ear: Much or less of trichome of lemma | Absence or extremely small | | Small | | Intermediate | | Much | | Extremely much | Equivalent to Koshihikari | | |
| 80-90 | Small ear: Color of lemma tip (apiculus color) | White | Yellow | Brown | Red | Purple | Black | | | | 1 | 1 | 1 |
| 90 | Ear: Curvature extent of main axis | Stand | | Tilt | | Hanging | | Bending | | | 5 | 5 | 5 |
| | Ear: Ear type | Lanceolate | Spindle-like | Bat-like | Bloom-like | Umbellar | | | | | 2 | 2 | 2 |
| | Maturing stage | Extremely early | | Early | | Intermediate | | Late | | Extremely late | 4 September 9 | 5 September 17 | 6 September 29 |
| | Glume color | Yellowish white | Gold color | Brown | Reddish pale purple | Purple | Black | | | | 1 | 1 | 1 |
| | Glume color: Pattern | Absence | Golden groove | Brown groove | Purple spot | Purple groove | | | | | 1 | 1 | 1 |

TABLE 15

| Stage | Character | Property value of cultivar (comparison with standard cultivar) | | | | | |
|---|---|---|---|---|---|---|---|
| | | 1 | 2 | 3 | 4 | 5 | 6 |
| 92 | Lemma: Anthocyanine coloring of top part | Absence or extremely pale | | Pale | | Intermediate | |
| | Lemma: length | | | Short | | Intermediate | |
| | Lemma: Color | Yellowish white | Gold color | Red | Purple | | |
| | Paddy: 1,000 particles weight (mature) | | | Light | | Intermediate | |
| | Paddy: Phenol reaction of palea | Absence | | Pale | | Intermediate | |
| | Brown rice: Length | | | Short | | Intermediate | |
| | Brown rice: Width | | | Thin | | Intermediate | |
| | Brown rice: Shape (seen from side) | Circular | Half circular | Half spindle-shape | Spindle-shape | Long spindle-shape | |
| | Brown rice: Color | White | Pale brown | Brown spot | Dark brown | Pale red | Red |
| | Brown rice: Fragrances | Absence or extremely weak | Faint | Strong | | | |
| GII | Seeds setting density | | Very sparse | Sparse | Slightly sparse | Intermediate | Slightly dense |

| Stage | Character | Property value of cultivar (comparison with standard cultivar) | | | Remark Value measured | Property value of control cultivar | |
|---|---|---|---|---|---|---|---|
| | | 7 | 8 | 9 | | Koshihikari | Nihonbare |
| 92 | Lemma: Anthocyanine coloring of top part | Deep | Extremely deep | | 1 | 1 | 1 |
| | Lemma: length | Long | | | 2 2.0 mm | 2 1.92 mm | 2 1.90 mm |
| | Lemma: Color | | | | 1 | 1 | 1 |
| | Paddy: 1,000 particles weight (mature) | Heavy | | | 6 23.6 g | 5 22.9 g | 6 23.7 g |
| | Paddy: Phenol reaction of palea | Deep | Presence | | 1 | 1 | 1 |
| | Brown rice: Length | Long | | | 5 5.10 mm | 5 5.09 mm | 6 5.26 mm |
| | Brown rice: Width | Thick | | | 5 2.85 mm | 5 2.81 mm | 5 2.85 mm |
| | Brown rice: Shape (seen from side) | | | | 2 1.96 mm | 2 1.98 mm | 2 2.03 mm |
| | Brown rice: Color | Purple spot | Purple | Dark purple/black | 2 | 2 | 2 |
| | Brown rice: Fragrances | | | | 1 | 1 | 1 |
| GII | Seeds setting density | Dense | Very dense | | 7 10.5 grains/cm$^2$ | 6 9.7 grains/cm$^2$ | 5 7.8 grains/cm$^2$ |

TABLE 16

| Stage | Character | Property value of cultivar (comparison with standard cultivar) | | | | | | | | | Remark Value measured | Property value of control cultivar | |
|---|---|---|---|---|---|---|---|---|---|---|---|---|---|
| | | 1 | 2 | 3 | 4 | 5 | 6 | 7 | 8 | 9 | | Koshihikari | Nihonbare |
| GIII | Main stem grain number | Extremely small | | Small | | Intermediate | | Large | | Extremely large | 6 157 grains | 5 143 grains | 4 113 grains |
| | Main stem first internode length | Extremely short | | Short | | Intermediate | | Long | | Extremely long | 8 33.3 cm | 8 36.54 cm | 8 34.7 cm |
| | Main stem second internode length | Extremely short | | Short | | Intermediate | | Long | | Extremely long | 5 18.8 cm | 7 21.42 cm | 5 17.35 cm |
| | Main stem third | Extremely | | Short | | Intermediate | | Long | | Extremely | 4 | 7 | 5 |

TABLE 16-continued

| Stage | Character | Property value of cultivar (comparison with standard cultivar) | | | | | | | | Remark Value measured | Property value of control cultivar | |
|---|---|---|---|---|---|---|---|---|---|---|---|---|
| | | 1 | 2 | 3 | 4 | 5 | 6 | 7 | 8 | 9 | | Koshihikari | Nihonbare |
| | internode length | short | | | | | | | | long | 12.22 cm | 18.74 cm | 14.35 cm |
| | Main stem forth internode length | Extremely short | | Short | | Intermediate | | Long | | Extremely long | 3 7.26 cm | 7 14.9 cm | 5 8.375 cm |
| | Main stem fifth internode length | Extremely short | | Short | | Intermediate | | Long | | Extremely long | 3 1.72 cm | 7 8.24 cm | 5 3.85 cm |
| | Main stem sixth internode length | Extremely short | | Short | | Intermediate | | Long | | Extremely long | 1 0 cm | 5 2.9 cm | 2 1 cm |
| | Thick of main stem paddy | Extremely thin | | Thin | | Intermediate | | Thick | | Extremely thick | 5 2.17 mm | 5 2.17 mm | 5 2.21 mm |
| | Length of main stem paddy | Extremely short | | Short | | Intermediate | | Long | | Extremely long | 3 7.4 mm | 3 7.13 mm | 3 7.53 mm |
| | Width of main stem paddy | Extremely narrow | | Narrow | | Intermediate | | Wide | | Extremely wide | 5 3.36 mm | 5 3.26 mm | 5 3.27 mm |
| | Ear harvest coefficient | Extremely low | | Low | | Intermediate | | High | | Extremely high | 8 56.8 | 5 44.6 | 2 36.9 |

That is, by comparison of characters between Koshihikari kazusa 4go, Koshihikari and Nihonbare, it was confirmed that Koshihikari kazusa 4go has a character which was expected at genome design that the Sd1 gene, the Hd1 gene and the Gn1 gene are substituted with Habataki-derived genes without influencing on other characters of Koshihikari as the original cultivar.

Therefore, from these results, it is clear that, by mating new cultivars created by using the method of creating a new cultivar of the present invention, a progeny individual in which all of homo-chromosome fragments derived from the foreign cultivar possessed by the seed parent and the pollen parent, respectively, are accumulated can be obtained, and is also clear that a new cultivar having plural kinds of target characters can be created without changing a preferable character possessed by the original cultivar.

Then, a Koshihikari genome substitution rate (ratio of Koshihikari genome as original cultivar occupied in entire genome) regarding each cultivar of Koshihikari kazusa 4go and Koshihikari eiichi 2 to 4go created in Examples is shown.

Lengths of chromosome fragments derived from Habataki in Koshihikari eiichi 2 to 4go created in Examples 1 to 3 are shown in Table 17. A possible minimum length of a Habataki-derived chromosome fragment is d2 and a maximum length thereof is d1+d2+d3.

TABLE 17

| | Distance between markers (kbp) | | | Minimum (kbp) | Maximum (kbp) |
|---|---|---|---|---|---|
| | d1 | d2 | d3 | d2 | d1 + d2 + d3 |
| Koshihikari eiichi 2go | 201.3 | 37.0 | 6.9 | 37.0 | 245.2 |
| Koshihikari eiichi 3go | 344.2 | 1507.9 | 1278.7 | 1507.9 | 3130.8 |
| Koshihikari eiichi 4go | 1.6 | 90.4 | 750.2 | 90.4 | 841.9 |

From a length of Habataki-derived chromosome fragments in Table 17, a foreign genome substitution rate [Habataki-derived chromosome fragment length/entire genome length×100(%)] and a Koshihikari genome substitution rate [100%−foreign genome substitution rate] were calculated. Results are shown in Table 18. A full genome length was let to be 430 Mbp.

TABLE 18

| | Foreign genome substitution rate (%) | | Koshihikari genome substitution rate (%) | |
|---|---|---|---|---|
| | Maximum | Minimum | Maximum | Minimum |
| Koshihikari eiichi 2go | 0.0570 | 0.0086 | 99.9914 | 99.9430 |
| Koshihikari eiichi 3go | 0.7281 | 0.3507 | 99.6493 | 99.2719 |
| Koshihikari eiichi 4go | 0.1958 | 0.0210 | 99.9790 | 99.8042 |
| Koshihikari kazusa 4go | 0.9809 | 0.3803 | 99.6197 | 99.0191 |

As shown in Table 18, since all of new cultivars created by the method of the present invention have a sufficiently high Koshihikari genome substitution rate (due to sufficiently small rate of substitution with foreign gene), characters other than a character due to a recombined objective gene are equivalent to those of Koshihikari (original cultivar), and it can be said that the new cultivars are an isogenic line of Koshihikari.

Koshihikari kazusa 4go is a new cultivar created by using the method of creating a new cultivar of the present invention, and is a very excellent new cultivar which is excellent in lodging resistance, and has a great yield and a wide cultivation region while a good character such as a taste possessed by Koshihikari is maintained. Then, the applicant deposited (accepted date: Jul. 1, 2008) Koshihikari kazusa 4go as a novel plant in International Patent Organism Depositary, National Institute of Advanced Industrial Science and Technology (Tsukuba Center Chuou $6^{th}$, Higashi 1-1-1, Tsukuba-shi, Ibaragi-ken, Japan (Post code 305-8566)), and this was transferred to International Deposition in the same Institute (acceptance date: Jun. 30, 2009). An accession number of International Deposition is FERM BP-11140.

INDUSTRIAL APPLICABILITY

Since by using the method of creating a new cultivar of the present invention, a region of a chromosome fragment derived from the foreign cultivar to be introduced can be controlled, and a new cultivar having one or plural kinds of target characters can be made without changing a preferable character possessed by the original cultivar, the method can be utilized, particularly, in the field of plant breeding.

The invention claimed is:

1. A rice cultivar created by using the method of creating a new cultivar using a chromosome fragment-substituted line in which only a part of a chromosome of an original cultivar substituted with a chromosome fragment derived from a foreign cultivar, the rice cultivar comprising:

a first region containing base number 38,109,578 to base number 38,199,633 in a first chromosome of the rice cultivar Koshihikari is homo-replaced with a chromosome fragment composed of a first region containing base number 38,109,578 to base number 38,199,633 in a first chromosome of rice cultivar Habataki in the first chromosome of the rice cultivar Koshihikari, the first region of the rice cultivar Koshihikari being defined by DNA markers M2 and M4, and an upstream end of the chromosome fragment composed of the first region of the rice cultivar Habataki is present in a second region containing base number 38,107,956 to base number 38,109,578 of the first chromosome of rice cultivar Koshihikari, the second region being defined by a DNA marker M1 and the DNA marker M2, and a downstream end of the chromosome fragment composed of the first region of the rice cultivar Habataki is present in a third region containing base number 38,199,633 to base number 38,949,811 of the first chromosome of rice cultivar Koshihikari, the third region being defined by the DNA marker M4 and a DNA marker M5, the first region of the rice cultivar Koshihikari comprising sd-1 gene which is a rice semidwarf gene;

a fourth region containing base number 5,230,897 to base number 5,267,932 in the first chromosome of rice cultivar Koshihikari is homo-replaced with a chromosome fragment composed of a fourth region containing base number 5,230,897 to base number 5,267,932 in the first chromosome of rice cultivar Habataki in the first chromosome of the rice cultivar Koshihikari, the fourth region of the rice cultivar Koshihikari being defined by DNA markers M7 and M9, and an upstream end of the chromosome fragment of the fourth region of the rice cultivar Habataki is present in a fifth region containing base number 5,029,585 to base number 5,230,897 of the first chromosome of rice cultivar Koshihikari, the fifth region being defined by a DNA marker M6 and the DNA marker M7, and a downstream end of the chromosome fragment of the fourth region of the rice cultivar Habataki is present in a sixth region containing base number 5,267,932 to base number 5,724,787 of the first chromosome of rice cultivar Koshihikari, the sixth region being defined by the DNA marker M9 and a DNA marker M10, the fourth region of the rice cultivar Koshihikari being a Gn1 gene controlling seeds setting density; and a seventh region containing base number 9,163,148 to base number 10,671,067 in a third chromosome of rice cultivar Koshihikari is homo-replaced with a chromosome fragment composed of a seventh region containing base number 9,163,148 to base number 10,671,067 in a third chromosome of rice cultivar Habataki in the third chromosome of the rice cultivar Koshihikari, the seventh region of the rice cultivar Koshihikari being defied by DNA markers M12 and M14, and an upstream end of the chromosome fragment of the seventh region of the rice cultivar Habataki is present in an eighth region containing base number 8,818, 923 to base number 9,163,148 of the sixth chromosome of rice cultivar Koshihikari, the eighth region being defined by a DNA marker M11 and the DNA marker M12, and a downstream end of the seventh region of the chromosome fragment of the rice cultivar Habataki is present in a ninth region containing base number 10,671,067 to base number 11,949,717 of the sixth chromosome of rice cultivar Koshihikari, the ninth region being defined by the DNA marker M14 and a DNA marker M15, the seventh region being Hd1gene controlling conversion into early growth;

wherein the DNA marker M1 is an SNP represented by the SP-4009 (SEQ ID NO: 3), wherein a base pair is the 38,107,956th SNP of the first chromosome of rice cultivar Koshihikari, guanine ("G") in rice cultivar Koshihikari and cytosine ("C") in rice cultivar Habataki, the DNA marker M2 is a polymorphism dependent on the 38,109,578th base sequence of the first chromosome of a rice cultivar Koshihikari, and amplification product is obtained in the rice cultivar Nipponbare, the amplification product is not obtained in the rice cultivar Habataki when PCR was performed using a primer TG2003U as in SEQ ID NO: 4 and a primer TG2003L as in SEQ ID NO: 5, a DNA marker M3 is a polymorphism dependent on the 38,109,641th base sequence of the first chromosome of the rice cultivar Nipponbare, and amplification product is obtained in the rice cultivar Koshihikari, the amplification product is not obtained in the rice cultivar Habataki when PCR was performed using a primer TG2002U as in SEQ ID NO: 6 and a primer TG2002L as in SEQ ID NO: 7, the DNA marker M4 is an SNP represented by the SP-462 (SEQ ID NO: 10), wherein a base pair is the 38,199, 633th SNP of the first chromosome of the rice cultivar Koshihikari, guanine ("G") in the rice cultivar Koshihikari and thymine ("T") in the rice cultivar Habataki, the DNA marker M5 is an SNP represented by the SP-1259 (SEQ ID NO: 13), wherein a base pair is the 8,949,811th SNP of the first chromosome of the rice cultivar Koshihikari, thymine ("T") in rice cultivar Koshihikari and cytosine ("C") in the rice cultivar Habataki;

the DNA marker M6 is an SNP represented by the SP-2032 (SEQ ID NO: 16), wherein a base pair is the 5,029,585th SNP of the first chromosome of the rice cultivar Koshihikari, thymine ("T") in the rice cultivar Koshihikari and guanine ("G") in the rice cultivar Habataki, the DNA marker M7 is an SNP represented by the SP-170 (SEQ ID NO: 19), wherein a base pair is the 5,230, 897th SNP of the first chromosome of the rice cultivar Koshihikari, thymine ("T") in the rice cultivar Koshihikari and adenine ("A") in the rice cultivar Habataki, a DNA marker M8 is an SNP represented by the SP-4028 (SEQ ID NO: 22), wherein a base pair is the 5,267, 633th SNP of the first chromosome of the rice cultivar Koshihikari, adenine ("A") in the rice cultivar Koshihikari and cytosine ("C") in the rice cultivar Habataki, the DNA marker M9 is an SNP represented by the SP-4038 (SEQ ID NO: 25), wherein a base pair is the 5,267,932th SNP of the first chromosome of the rice cultivar Koshihikari, guanine ("G") in the rice cultivar Koshihikari and cytosine ("C") in the rice cultivar Habataki, the DNA marker M10 is an SNP represented by the SP-4030 (SEQ ID NO: 28), wherein a base pair is the 5,724,787th SNP of the first chromosome of the rice cultivar Koshihikari, adenine ("A") in the rice cultivar Koshihikari and thymine ("T") in the rice cultivar Habataki;

the DNA marker M11 is an SNP represented by the SP-2513 (SEQ ID NO: 31), wherein a base pair is the 8,818,923th SNP of the sixth chromosome of the rice cultivar Koshihikari, cytosine ("C") in the rice cultivar Koshihikari and thymine ("T") in the rice cultivar Habataki, the DNA marker M12 is an SNP represented by the SP-586 (SEQ ID NO: 34), wherein a base pair is the 9,163,148th SNP of the sixth chromosome of the rice cultivar Koshihikari, cytosine ("C") in the rice cultivar Koshihikari and adenine ("A") in the rice cultivar Habataki, a DNA marker M13 is an SNP represented by the SP-2254 (SEQ ID NO: 37), wherein a base pair is the 9,379, 247th SNP of the sixth chromosome of the rice cultivar Koshihikari, cytosine ("C") in the rice cultivar Koshihikari and guanine ("G") in the rice cultivar Habataki, the DNA marker M14 is an SNP represented by the SP-1603 (SEQ ID NO: 40), wherein a base pair is the 10,671,067th SNP of the sixth chromosome of the rice cultivar Koshihikari, thymine ("T") in the rice cultivar Koshihikari and cytosine ("C") in the rice cultivar Habataki, the DNA marker M15 is an SNP represented by the SP-604 (SEQ ID NO: 43), wherein a base pair is the 11,949,717th SNP of the sixth chromosome of the rice cultivar Koshihikari, thymine ("T") in the rice cultivar Koshihikari and cytosine ("C") in the rice cultivar Habataki;

the DNA markers M1 to M15 are typed by genome analysis of the rice cultivar; and the rice cultivar is *Oryza sativa* L. cultivar Koshihikari kazusa 4go, representative seed of said cultivar having been deposited under FERM BP-11140.

2. A method for producing progeny, said method comprising the step of mating the cultivar of claim 1 with another plant.

* * * * *